(12) United States Patent
Morgan et al.

(10) Patent No.: US 12,336,844 B2
(45) Date of Patent: Jun. 24, 2025

(54) MONITORING PHYSIOLOGICAL PARAMETERS

(71) Applicant: THE UNIVERSITY OF NOTTINGHAM, Nottingham (GB)

(72) Inventors: Stephen Morgan, Nottingham (GB); Barrie Hayes-Gill, Nottingham (GB); Serhiy Korposh, Nottingham (GB); Ricardo Correia, Nottingham (GB)

(73) Assignee: The University of Nottingham, Nottingham (GB)

( * ) Notice: Subject to any disclaimer, the term of this patent is extended or adjusted under 35 U.S.C. 154(b) by 982 days.

(21) Appl. No.: 17/250,821

(22) PCT Filed: Sep. 3, 2019

(86) PCT No.: PCT/GB2019/052454
§ 371 (c)(1),
(2) Date: Mar. 5, 2021

(87) PCT Pub. No.: WO2020/049291
PCT Pub. Date: Mar. 12, 2020

(65) Prior Publication Data
US 2021/0251571 A1    Aug. 19, 2021

(30) Foreign Application Priority Data
Sep. 5, 2018    (GB) .................................... 1814465

(51) Int. Cl.
*A61B 5/00*    (2006.01)
*A61B 5/1455*    (2006.01)
(Continued)

(52) U.S. Cl.
CPC ........ *A61B 5/6804* (2013.01); *A61B 5/14552* (2013.01); *A61B 5/6843* (2013.01);
(Continued)

(58) Field of Classification Search
CPC . A61B 5/0205; A61B 5/1455; A61B 5/14551; A61B 5/14552; A61B 5/68;
(Continued)

(56) References Cited

U.S. PATENT DOCUMENTS

| | | | |
|---|---|---|---|
| 6,278,811 B1 * | 8/2001 | Hay | G01L 11/025 385/13 |
| 8,352,004 B2 * | 1/2013 | Mannheimer | A61B 5/6843 600/310 |

(Continued)

FOREIGN PATENT DOCUMENTS

| | | |
|---|---|---|
| GB | 2562719 A | 11/2018 |
| WO | 2009136311 A1 | 11/2009 |

(Continued)

OTHER PUBLICATIONS

L L Blaxter et al., An automated quasi-continuous capillary refill timing device, Physiological Measurement, 2016, vol. 37, Issue 83, IOP Publishing, doi: 10.1088/0967-3334/37/83.
(Continued)

*Primary Examiner* — Chu Chuan Liu
(74) *Attorney, Agent, or Firm* — Grossman, Tucker, Perreault & Pfleger, PLLC; Paul J. Kroon

(57) ABSTRACT

The present invention relates to a system (100) for monitoring one or more physiological parameters of an individual. The system (100) comprises an optical fibre assembly (110) configured to measure one or more physiological parameters of an individual, and a pressure sensor (120) configured to measure a contact pressure of the optical fibre assembly (110) on the individual. The pressure sensor (120) comprises an optical fibre (122) comprising a transducer fibre Bragg grating (127) embedded in a matrix (121). The matrix (121) is configured to cause longitudinal strain in the transducer fibre Bragg grating (127) in response to the matrix (121) being subject to a transverse load. The one or
(Continued)

more physiological parameters that the system (100) is for monitoring may include blood oxygen saturation (Sp O2), capillary refill time (CRT), heart rate, blood flow and CO2 emissions from skin.

19 Claims, 36 Drawing Sheets

(51) Int. Cl.
  *D03D 15/547* (2021.01)
  *D04B 1/16* (2006.01)
  *D05C 17/00* (2006.01)
  *G02B 6/02* (2006.01)

(52) U.S. Cl.
  CPC ............ *D03D 15/547* (2021.01); *D04B 1/16* (2013.01); *D05C 17/00* (2013.01); *G02B 6/02176* (2013.01); *A61B 2562/0238* (2013.01); *D10B 2401/20* (2013.01)

(58) Field of Classification Search
  CPC ... A61B 5/6801; A61B 5/6802; A61B 5/6803; A61B 5/6804; A61B 5/6805; A61B 5/6806; A61B 5/6813; A61B 5/6822; A61B 5/6823; A61B 5/6825; A61B 5/6828; A61B 5/683; A61B 5/6831; A61B 5/6843; A61B 5/02416; A61B 2562/0238
  See application file for complete search history.

(56) References Cited

U.S. PATENT DOCUMENTS

| 2004/0074307 | A1  | 4/2004  | Tjin |
|---|---|---|---|
| 2010/0249557 | A1* | 9/2010  | Besko ................. A61B 5/6814 600/340 |
| 2013/0218025 | A1* | 8/2013  | Tverskoy ........... A61B 5/14552 600/476 |
| 2014/0268099 | A1  | 9/2014  | Moslehi |
| 2017/0119293 | A1  | 5/2017  | Matsui |
| 2017/0340216 | A1  | 11/2017 | Morgan et al. |

FOREIGN PATENT DOCUMENTS

| WO | 2016036314 A1 | 3/2016 |
|---|---|---|
| WO | 2016110781 A1 | 7/2016 |
| WO | 2017/037479   | 3/2017 |

OTHER PUBLICATIONS

Search Report under Section 17(5) of Great Britain application No. GB1814465.9, Dated Mar. 6, 2019, 4 pages.

Peyman Mirtaheri et al., A Review of the Role of the Partial Pressure of Carbon Dioxide in Mechanically Loaded Tissues: The Canary in the Cage Singing in Tune with the Pressure Ulcer Mantra, Annals of Biomedical Engineering, Dec. 2014, doi: 10.1007/s10439-014-1233-z.

International Search Report from corresponding PCT Application No. PCT/GB2019/052454 dated Nov. 14, 2019.

Written Opinion of the International Searching Authority from corresponding PCT Application No. PCT/GB2019/052454 dated Nov. 14, 2019.

* cited by examiner

- Post-Occlusive reactive Hyperaemia
Sean M. Lanting et. al papers (2017)

MONITORING PHYSIOLOGICAL PARAMETERS

FIELD OF THE INVENTION

The present invention relates to a system for monitoring one or more physiological parameters of an individual.

BACKGROUND

Optical sensors are widely used as part of non-invasive techniques for measuring physiological parameters, and are commonly found in medical devices. Examples of physiological parameters that can be measured using optical techniques include the measurement of blood oxygen saturation level ($S_pO_2$), capillary refill time, heart rate, blood flow, and $CO_2$ emission from skin (which can be an indication of tissue breakdown).

However, such optical sensors typically require an optimal contact pressure to obtain accurate, reliable measurements of physiological parameters. The use of non-invasive optical sensors typically relies on the acquired experience of skilled medical staff to apply an optimal contact pressure. If the contact pressure is not optimal, the medical staff must then be able to identify obtained measurements which, as a result of non-optimal contact pressure during data collection, are not accurate or reliable.

As the use of wearable technology and smart textiles increases, integration of such optical sensors into textiles (such as those used in compression bandages) may enable improved medical care.

A smart textile would also be useful in the context of other compression garments, such as those used in recovery from sports (e.g. shirts, shorts, leggings etc).

SUMMARY

According to a first aspect of the invention, there is provided a system comprising an optical fibre assembly configured to measure one or more physiological parameters of an individual, and a pressure sensor configured to measure a contact pressure of the optical fibre assembly on the individual.

The one or more physiological parameters may be selected from: blood oxygen saturation ($S_pO_2$), capillary refill time, heart rate, blood flow and $CO_2$ emissions from skin.

Accuracy and reliability of measurements of physiological parameters obtained using optical systems are typically sensitive to contact pressure between the optical system and the individual (e.g., skin of the individual). Too low a contact pressure can result in the optical sensor not detecting a high enough light intensity to accurately measure or determine a physiological parameter. Low contact pressure can also result in motion artefacts if the sensor moves relative to the skin. Conversely, too high a contact pressure can negatively affect the reliability of obtained results by artificially affecting (e.g., inhibiting or exacerbating) the measured physiological parameter. For example, if the optical system is used to measure blood oxygen saturation, too high a contact pressure can occlude blood flow to the region of skin being measured. An optimal pressure range for collecting reliable, accurate measurements of physiological parameters using optical fibre assemblies generally exists.

Providing the system of the first aspect of the invention may improve the accuracy and/or the reliability of physiological measurements obtained using an optical fibre assembly. A further advantage may be that the skill element of a user in correctly placing the system, or manually applying an optimal pressure based on acquired experience to obtain measurements, may be reduced or removed. Correlation of physiological parameter data measured by the optical fibre assembly with pressure data measured by the pressure sensor may make it easy to identify which results can be identified as reliable and accurate.

The pressure sensor may comprise an optical fibre comprising a transducer fibre Bragg grating. The transducer fibre Bragg grating may be embedded in a matrix. The Matrix may be configured to cause longitudinal strain in the transducer fibre Bragg grating in response to the matrix being subject to a transverse load.

The optical fibre of the pressure sensor may further comprise a temperature compensation fibre Bragg grating. The temperature compensation fibre Bragg grating may be received in a clearance fit in a cavity of a rigid support member isolating the temperature compensation fibre Bragg grating from a transverse load. The temperature compensation fibre Bragg grating may be free to expand and contract independently of the rigid support member.

The optical fibre of the pressure sensor may further comprise a strain compensation fibre Bragg grating.

The matrix containing the transducer fibre Bragg grating may comprise an elongated longitudinal section relative to a length of the transducer fibre Bragg grating. The elongated longitudinal section may isolate the transducer fibre Bragg grating from strain caused by longitudinal extension of the optical fibre.

The optical fibre may comprise a plurality of transducer fibre Bragg gratings. Each of the plurality of fibre Bragg gratings may be embedded in a respective matrix.

One or more of the plurality of transducer fibre Bragg gratings may have a corresponding strain compensation fibre Bragg grating. Alternatively, the matrix of one or more of the plurality of transducer fibre Bragg gratings may comprise an elongated longitudinal section relative to a length of the transducer fibre Bragg grating.

One or more optical fibres of the optical fibre assembly may be embedded in a matrix (or patch) such that the ends of the optical fibres of the optical fibre assembly are able to transmit light to or receive light from the individual when an outer surface of the matrix is in contact with the individual. In some embodiments at least some of the ends of the optical fibre assembly may not transmit light to or receive light from the individual. For example, at least one of the optical fibres in the fibre assembly may comprise a coating (e.g dye) on the tip that is responsive to a gas (e.g. $CO_2$). Alternatively or additionally, a small void may be disposed in matrix (or patch) close to the tip, wherein the small void is configured to collect the gas.

The one or more optical fibres of the optical fibre assembly may be embedded in the same matrix as the matrix in which a transducer fibre Bragg grating of the optical fibre of the pressure sensor. Alternatively, the matrix in which the one or more optical fibres of the optical fibre assembly are embedded may be connected to a matrix in which a transducer fibre Bragg grating of the optical fibre of the pressure sensor is embedded.

The matrix in which the one or more optical fibres of the optical fibre assembly are embedded may comprise scattering elements configured to diffusely scatter light from the optical fibres.

The system may comprise a scattering layer disposable between the matrix in which the one or more optical fibres of the optical fibre assembly are embedded and the individual, wherein the scattering layer is configured to diffusely scatter light from the optical fibres. In some embodiments, the scattering layer is disposed within the matrix itself. In other embodiments, scattering particles are disposed within the matrix, wherein the scattering particles are configured to diffusely scatter light from the optical fibres.

The optical fibre assembly may be configured to measure blood oxygen saturation of an individual when in contact with the individual. The optical fibre assembly may comprise: a first optical fibre configured to deliver light to the individual at a first wavelength; a second optical fibre configured to deliver light to the individual at a second wavelength; and a third optical fibre configured to receive light reflected from the individual at both the first and second wavelength.

According to a second aspect of the invention, there is provided a handheld probe comprising the system of the first aspect.

According to a third aspect of the invention, there is provided a textile comprising the system of the first aspect. The optical fibres of the optical fibre assembly may be integrated with the textile by knitting, weaving, embroidering or threading the optical fibres into the textile.

The optical fibre of the pressure sensor may be integrated with the textile by knitting, weaving, embroidering or threading the optical fibre into the textile.

According to a fourth aspect of the invention, there is provided a compression bandage or garment (e.g. compression garment) comprising the textile of the third aspect. The garment may comprise a sock or stocking.

According to a fifth aspect of the invention, there is provided a loose fitting garment comprising the textile of the third aspect. The optical fibre assembly may be configured to measure the one or more physiological parameters only when an appropriate pressure is applied.

The appropriate pressure may be between from 5 kPa to 15 kPa.

According to a sixth aspect of the invention, there is provided a method of monitoring a physiological parameter of an individual. The method comprises: applying an optical fibre assembly to an individual; measuring the physiological parameter using the optical fibre assembly; and measuring the contact pressure of the optical fibre assembly on the individual using a pressure sensor.

The optical fibre assembly may be configured to measure the physiological parameter only when contact pressure of the optical fibre assembly measured by the pressure sensor is determined to be within an optimal range.

The optimal range of contact pressure of the optical fibre assembly may be between from 5 kPa to 15 kPa.

The optical fibre assembly and the pressure sensor may be integrated with a textile. The method may further comprise applying the textile to the individual to measure the physiological parameter and the contact pressure.

Applying the textile to the individual may comprise at least one of the individual i) wearing the textile, ii) lying on the textile, iii) sitting on the textile, iv) resting part of their body on the textile, and/or v) performing an activity whilst at least part of the body is in contact with the textile.

The optical fibre assembly and the pressure sensor may be incorporated into a handheld probe.

The pressure sensor may comprise an optical fibre comprising a transducer fibre Bragg grating. The transducer fibre Bragg grating may be embedded in a matrix. The matrix may be configured to cause longitudinal strain in the transducer fibre Bragg grating in response to the matrix being subject to a transverse load.

The features of any aspect may be combined with those of any other aspect. For example, the method of the sixth aspect may be performed using the system of any preceding aspect.

BRIEF DESCRIPTION OF DRAWINGS

The invention will now be described by way of example with reference to the accompanying drawings in which.

Features which are described in the context of separate aspects and embodiments of the invention may be used together and/or be interchangeable wherever possible. Similarly, where features are, for brevity, described in the context of a single embodiment, these may also be provided separately or in any suitable sub-combination. Features described in connection with the system may have corresponding features definable with respect to the method, and these embodiments are specifically envisaged.

DETAILED DESCRIPTION

Figure 1:
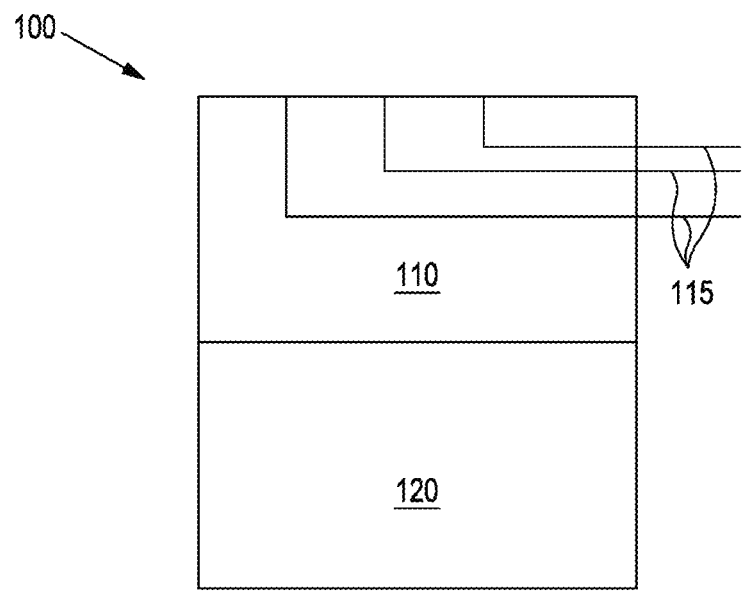
FIG. 1 is a schematic drawing of a monitoring system comprising an optical fibre assembly and a pressure sensor according to an embodiment.

FIG. 1 shows a schematic of a system 100 comprising an optical fibre assembly 110 and a pressure sensor 120. The optical fibre assembly 110 may comprise one or more optical fibres 115 for measuring one or more physiological parameters of an individual by providing light via one or more of the optical fibres 115 and measuring, for example, transmission of that light through, or reflectance of that light from skin of the individual using one or more of the optical fibres 115. Transmission or reflectance of light from skin of the individual may be used to determine a wide range of physiological parameters of the individual, including but not limited to blood oxygen saturation ($S_pO_2$), capillary refill time, heart rate, blood flow, and $CO_2$ emission from skin (which can indicate tissue breakdown).

The pressure sensor 120 is configured to measure contact pressure applied to the individual by the optical fibre assembly. The pressure sensor 120 may be any suitable pressure sensor, for example the pressure sensor 120 may be a piezoelectric, capacitive or electromagnetic pressure sensor.

Figure 2:
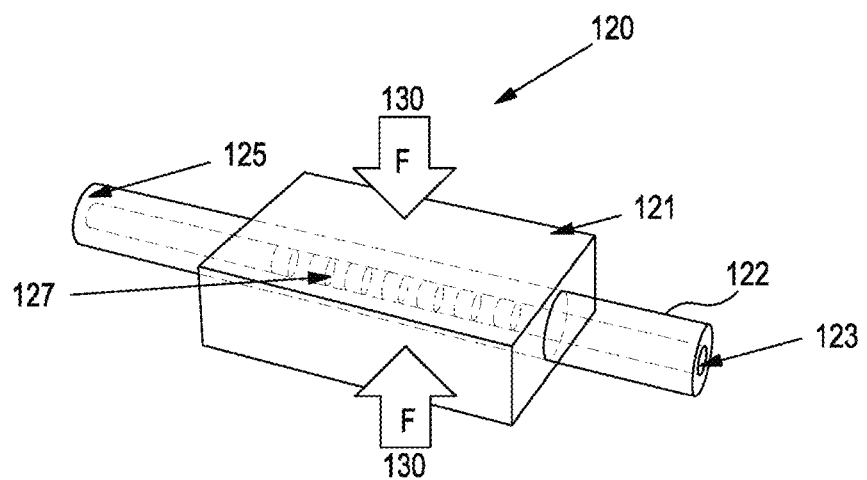
FIG. 2 is a schematic drawing of an FBG patch sensor according to an embodiment.

Alternatively, the pressure sensor 120 may be or comprise an optical fibre 122 embedded in a matrix or patch 121, as shown in FIG. 2.

The fibre 122 comprises a fibre Bragg grating (FBG) 127, in which the refractive index of the fibre has a periodic variation (e.g., written by masking or interference of a UV laser). A FBG has a characteristic spectral response, defined by the periodic variation in refractive index or grating period. FBGs typically have a very narrow spectral peak in reflectance corresponding with the grating period. Longitudinal strain in the fibre will change the grating period and effective refractive index of the core mode, resulting in a change in the wavelength of the spectral peak, which can be detected with a high degree of precision. When the FBG is illuminated with a broadband optical source, a narrow-band spectral component will be reflected from the FBG, while other wavelengths outside this band will be transmitted. The wavelength of this reflectance peak may be termed the Bragg wavelength. The Bragg wavelength is linearly dependent on the grating period and effective refractive index. The change in Bragg wavelength can be used to infer the pressure load exerted on the patch. The FBG may be between 1 mm and 4 mm long.

The matrix 121 may be formed of any suitable material, such as a polymer, or more specifically an epoxy resin. The matrix 121 may be or comprise a clear, transparent or translucent material. The matrix may have a length and breadth that is substantially similar (for example 3 mm to 10 mm, or 4 mm to 6 mm), and a thickness that is smaller than the length (for example 0.5 mm to 3 mm). In other embodiments the length of the patch may be different (e.g. at least double or triple, or less than half or a quarter) the width of the patch.

The optical fibre 122 is normal to the thickness dimension of the patch, and substantially parallel to the two opposing largest faces of the patch. The optical fibre is preferably embedded in the centre of the patch (i.e. approximately equidistant from the two opposing largest faces). The patch 121 comprises a material with a Poisson's ratio greater than zero, so that extension in length and breadth occurs when the patch 121 is subject to strain in the thickness dimension as a result of a transverse load 130. A reduction in thickness of the patch 121 due to a pressure load on the opposing largest faces of the patch 121 results in an increase in the length and width of the patch 121, as a result of the well-known Poisson effect. For epoxy resins, Poisson's ratio may typically be in the range of 0.35 to 0.42. Since the fibre 122 is embedded in the patch 121, the patch 121 transfers longitudinal strain to the fibre 122 within the patch 121 in response to the transverse pressure load.

The patch 121 may be between 1.2 and 2.5 times the length of the FBG that is embedded therein.

The Young's modulus of the patch material may be varied to provide a different dynamic range and pressure sensitivity of the sensor. The relationship between the Young's modulus of the patch 121 and the coupling of transverse load (or pressure) to extension of the optical fibre 122 may be determined by finite element analysis of the patch and optical fibre. A more flexible patch material will deform more under a specific pressure load, but the reduced stiffness of the patch material may mean that the patch struggles to deform the relatively stiff optical fibre. The patch 121 may be any shape—circular and square patches have been shown to produce good results, but any 3D shape including cylindrical shapes may be used.

The fibre 122 comprises a core 123 and cladding 125. A difference in refractive index between the core 123 and cladding 125 means that light is confined within the core 123 by total internal reflection at the interface between core and cladding.

The patch 121 is configured to provide reduced responsiveness of the embedded FBG to bending (e.g. when the patch is integrated with a textile), primarily by use of a small patch, so that the patch is relatively stiff in bending. The patch 121 therefore prevents bending of the FBG 122.

Figure 3:
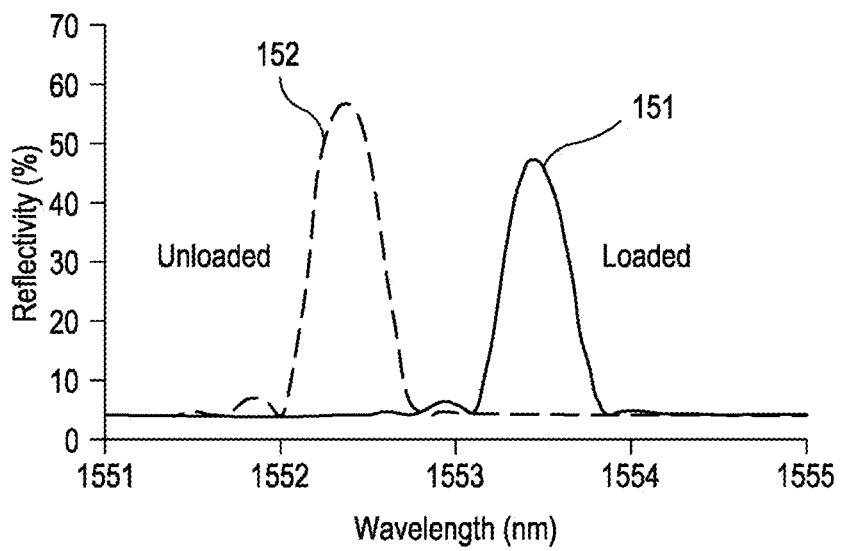
FIG. 3 is a graph illustrating the response of the patch sensor to a transverse load.

FIG. 3 illustrates the spectral response of an FBG when unloaded 152 and when subject to a longitudinal (or axial) load 151. The Bragg wavelength has increased in response to the axial load on the fibre, which has increased the grating period by extending the fibre.

Figure 4:
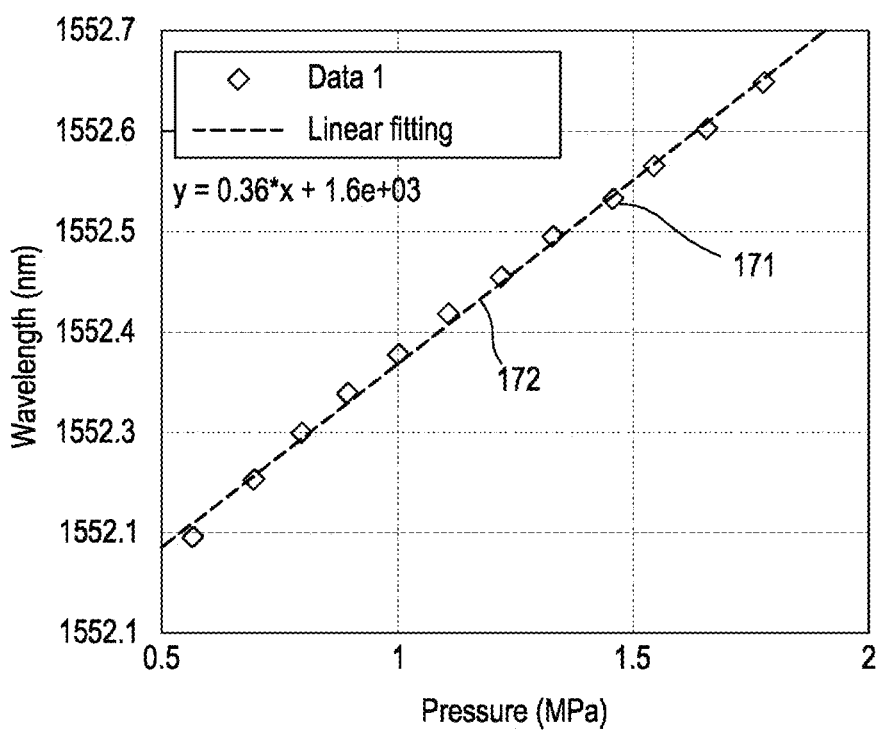
FIG. 4 is a further graph illustrating the linearity of the response of a patch sensor according to an embodiment.

FIG. 4 illustrates the relationship between the Bragg wavelength and an applied transverse pressure load on the patch 121. Data points 171 are shown indicating each measurement of the Bragg wavelength at different pressures. A linear fit 172 is also shown, which is a very good match for the data: the response is very linear.

An optical fibre may be formed with a plurality of Bragg gratings. Patches (as described above) may be formed around at least some of these gratings to form pressure transducers (e.g. a one dimensional array of pressure transducers along the fibre). A grating that is embedded in a patch and which is thereby made responsive to pressure may be termed a transducer FBG, and a patch for rendering an FBG sensitive to pressure may be termed a transducer patch.

Others of the Bragg gratings may be used as temperature and strain reference gratings. An FBG will also respond to temperature—thermal expansion can change the grating period and the refractive index of the materials comprising the FBG. In order to compensate for changes in Bragg wavelength in response to temperature variation, an FBG of the optical fibre can be used as a temperature reference. The temperature reference FBG should preferably be insensitive to strain, so should ideally be protected from extension and bending within a stiff support structure.

A further FBG can be used to compensate for tension within the optical fibre, for example resulting from extension of the fibre due to stretching of a textile within which the optical fibre is integrated. As the Young's modulus of the optical fibre 122 is likely to be higher than that of the patch material, any longitudinal force applied to the optical fibre 122 in the vicinity of the patch 121 will result in strain along the transducer FBG within the transducer patch. A strain compensation FBG may be used to compensate for this effect.

Figure 5:
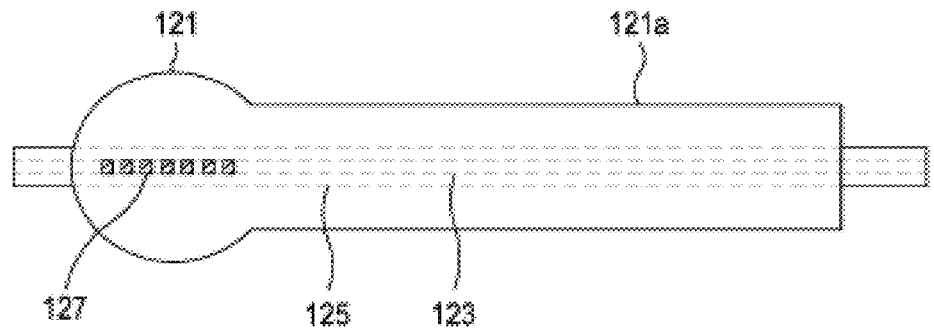
FIG. 5 is a schematic of an optical fibre based pressure sensor comprising an elongated portion according to an embodiment.

Alternatively, the matrix or patch 121 may be shaped or configured to isolate the transducer FBG 127 from strain along the longitudinal axis of the optical fibre 122 resulting from extension of the fibre. For example, the patch 121 may comprise an extended or elongated portion or region 121a along the longitudinal axis of the optical fibre 122, as shown in FIG. 5. FIG. 5 shows a plan view of the pressure sensor 120, with the core 123 and the cladding 125 of the optical fibre 122 shown in dashed lines to indicate those components are contained or embedded within other components where relevant. The length of the elongated portion may be at least 2, 3, 4 or 5 times the width of the transducer patch (at the FBG 127).

By incorporating an elongated portion 121a in the patch 121, the transducer FBG 127 may experience longitudinal axial strain resulting from a transverse pressure load without experiencing longitudinal axial strain resulting from extension of the fibre itself (i.e. the elongated portion 121a may provide strain relief for the fibre within the patch 121). This is because longitudinal axial strain resulting from extension of the fibre 122 is substantially concentrated in the elongated portion 121a rather than in the transducer FBG 127. In this way, a strain compensation FBG may not be required for each transducer FBG 127 of the optical fibre 122. The number of 'active' transducer FBGs 127 in the optical fibre 122 (i.e., FBGs used for pressure measurement, rather than for compensation to correct pressure measurements made by other FBGs) may therefore be increased, increasing the density of pressure measurement locations within a single optical fibre 122.

Alternatively, the patch or matrix 121 may comprise a plurality of elongated portions 121a. For example, the transducer FBG 127 may be located centrally in the matrix 121, with a first elongated portion 121a extending in a first direction along the longitudinal length of the optical fibre 122, and a second elongated portion 121a extending in a second direction along the longitudinal length of the optical fibre 122, the first direction being antiparallel to the second direction.

Figure 6:
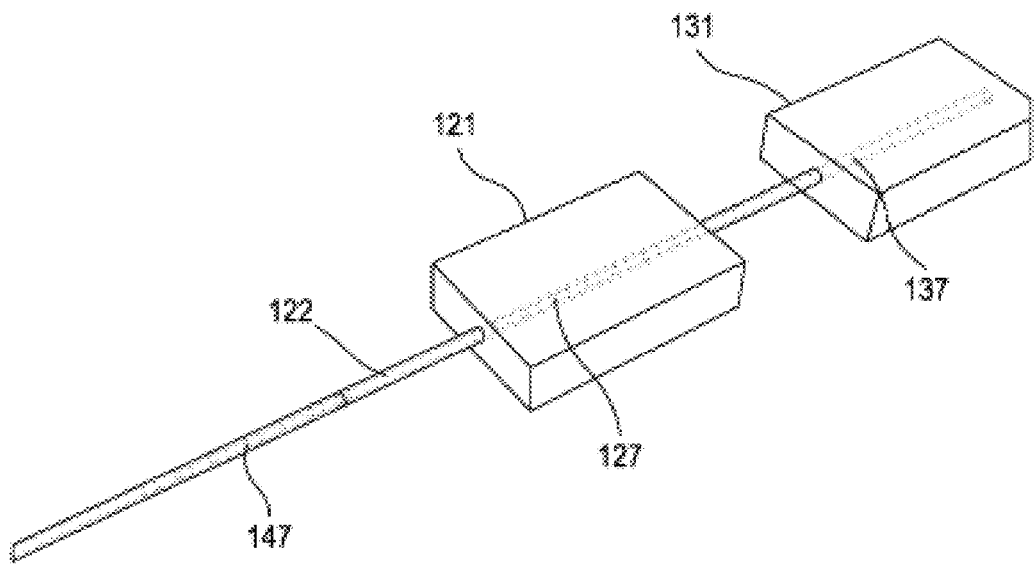
FIG. 6 is a schematic of an optical fibre based pressure sensor according to an embodiment comprising an FBG pressure transducer patch, a strain reference grating and a temperature reference grating.

FIG. 6 illustrates an example embodiment in which the optical fibre 122 includes a temperature compensation FBG 137, a transducer FBG 127 and a strain compensation FBG 147.

The transducer FBG 127 is integrated within a transducer patch 121, which couples transverse pressure loads into extensional strain in the transducer FBG 127 (as already described).

The temperature compensation FBG 137 is near to (e.g. within 2 cm, 1 cm, or 0.5 mm) the end of the optical fibre 122 and surrounded by a rigid sleeve. The sleeve may be any stiff material such as a metal (e.g. steel). A hypodermic needle or similar may be used as a sleeve. The sleeve is retained over the optical fibre 122 by a patch or matrix 131. There is clearance between the sleeve and optical fibre 122, so that the optical fibre remains free to extend and contract due to thermal expansion within the sleeve. The sleeve therefore prevents loading and bending of the end of the fibre 122, while allowing it to respond naturally to temperature changes (as if it were uncoupled from any structure). The patch 131 may have the same properties as the transducer patch 121 around the (or each) transducer FBG 127, so that thermal conductivity and insulation for the temperature compensation FBG 137 is as representative as possible of conditions at the transducer FBG(s) 127.

The strain compensation FBG 117 is not supported by a patch, so is not rendered sensitive to pressure. The strain compensation FBG 147 is responsive to extension of the fibre 122 as a result of tension forces (and may also be subject to changes in grating period arising from bending of the optical fibre 122) and to temperature.

The change in Bragg wavelength for the temperature compensation FBG 137 can be attributed entirely to temperature response. The change in Bragg wavelength for the strain compensation FBG 147 will be due to a combination of temperature response and strain response. The reading from the temperature compensation FBG 137 can be used to remove the temperature response from the strain compensation FBG 147, to leave the strain response only. The strain and temperature response can be used to compensate the response of the transducer FBG 127. One way to do this is to simply subtract the change in wavelength resulting from strain and temperature from the observed change in wavelength at the transducer FBG 127. More complex compensation schemes may also be used, in which a model of the strain and temperature response of the transducer FBG 127 is used to derive a correction from the temperature and strain inferred from the compensation FBGs 137, 147. In some embodiments, the compensation for both temperature and strain can be determined from the corresponding strain compensation FBG only.

In alternative embodiments, the optical fibre 122 may comprise a transducer FBG 127 in a matrix or patch 121 having one or more elongated portions 121a, and a temperature compensation FBG 137 in a matrix or patch 131. In such embodiments, a strain compensation FBG for the transducer FBG 127 may not be necessary.

The optical fibre 122 may comprise 'n' transducer FBGs, and a corresponding plurality of 'n' strain compensation FBGs. Each strain compensation FBG 147 may be positioned near to the corresponding transducer FBG 127 (e.g. within less than 1 cm or within less than 2 cm), so that the strain compensation FBG 147 can provide a strain correction that is more closely matched to the strain conditions at the corresponding transducer FBG 127.

Figure 7:
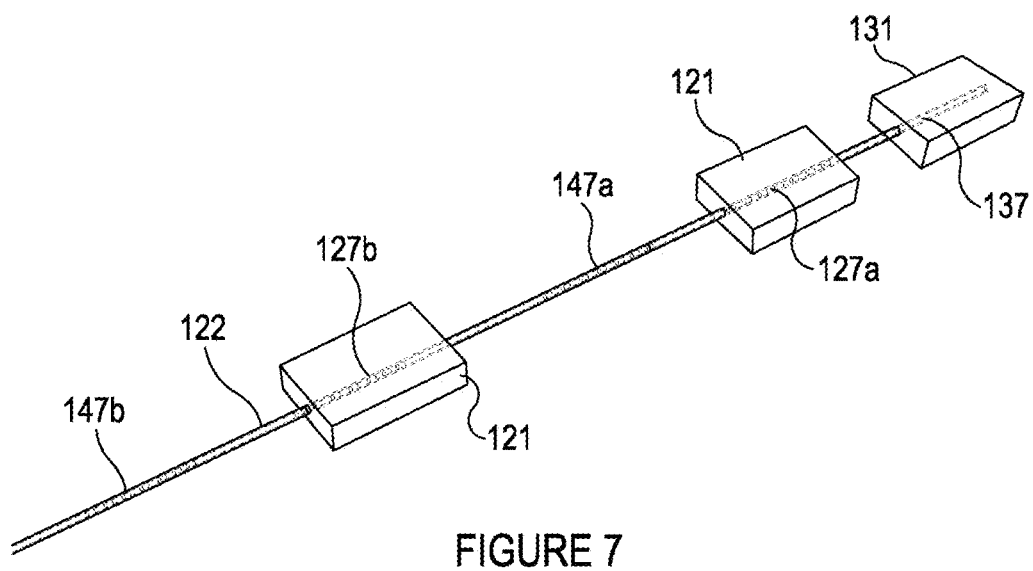
FIG. 7 is a schematic of an optical fibre based pressure sensor according to an embodiment comprising a first and second pressure transducer patch, a first and second strain reference grating, and a temperature reference grating.

FIG. 7 illustrates an example embodiment in which there are two transducer FBGs 127a, 127b, each embedded within a respective patch 121. A single temperature compensation FBG 137 is provided at the end of the optical fibre 122 (as previously described with reference to FIG. 4). Strain compensation FBGs 147a, 147b are provided adjacent to each transducer FBG 127a, 127b. Although an example with only two transducer FBGs is shown, it will be understood that a larger number of transducer FBGs 127 may be used on a single optical fibre (e.g. at least 5, at least 10, at least 20 or at least 50). In alternative embodiments, wherein the matrix 121 surrounding each transducer FBG 127 comprises an elongated portion 121a, a strain compensation FBG may not be required for each transducer FBG 127. In such embodiments, the number of transducer FBGs 127 used on a single optical fibre may be up to twice the number used in embodiments where a strain compensation FBG is required for each transducer FBG 127.

Each FBG in an optical fibre may have a slightly different Bragg frequency, so that the response of each FBG in a fibre may be simultaneously determine from the spectral response of the fibre. Provided each FBG has a sufficiently distinct Bragg wavelength it will be straightforward to identify which reflectance peak corresponds with which FBG in the optical fibre 122.

In some embodiments the optical fibre 122 may comprise a high birefringent ('HiBi') optical fibre, having two Bragg reflection peaks: one corresponding with horizontally polarized light, and the other corresponding with vertically polarised light. When a transverse load is applied to a HiBi transducer FBG 127 (embedded in a transducer patch 121) the Bragg reflection peaks will separate (or their degree of separation will change)—the response of the peak corresponding with horizontally polarised light will be different to the response of the peak corresponding with vertically polarised light. When a shear stress is applied to the transducer patch 121, the wavelength of both peaks will be affected equally. This is depicted in FIGS. 8 and 9, which respectively illustrate the response of a HiBi transducer FBG 127 in response to a transverse load and a shear stress.

Figure 8:
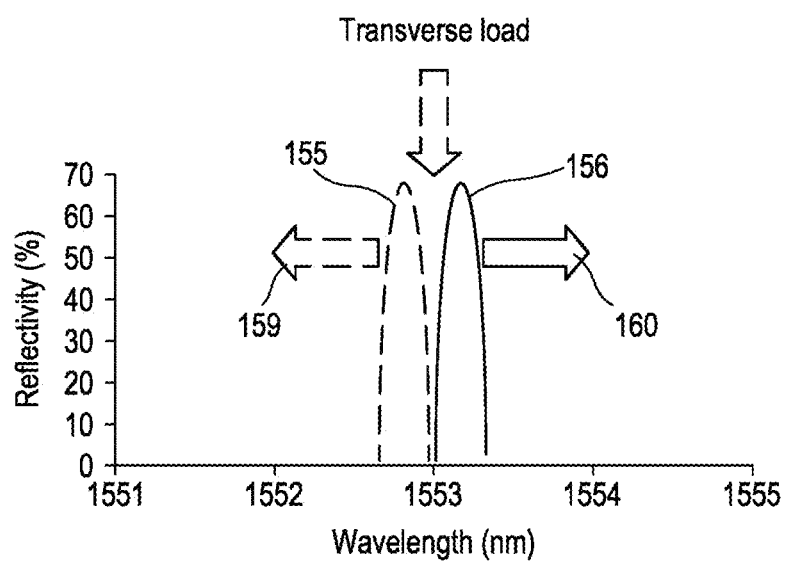
FIGS. 8 and 9 are graphs illustrating the response of an FBG sensor comprising a high birefringent fibre to a transverse load and shear load respectively, illustrating that such a sensor can distinguish between pressure and shear loading.
Figure 9:
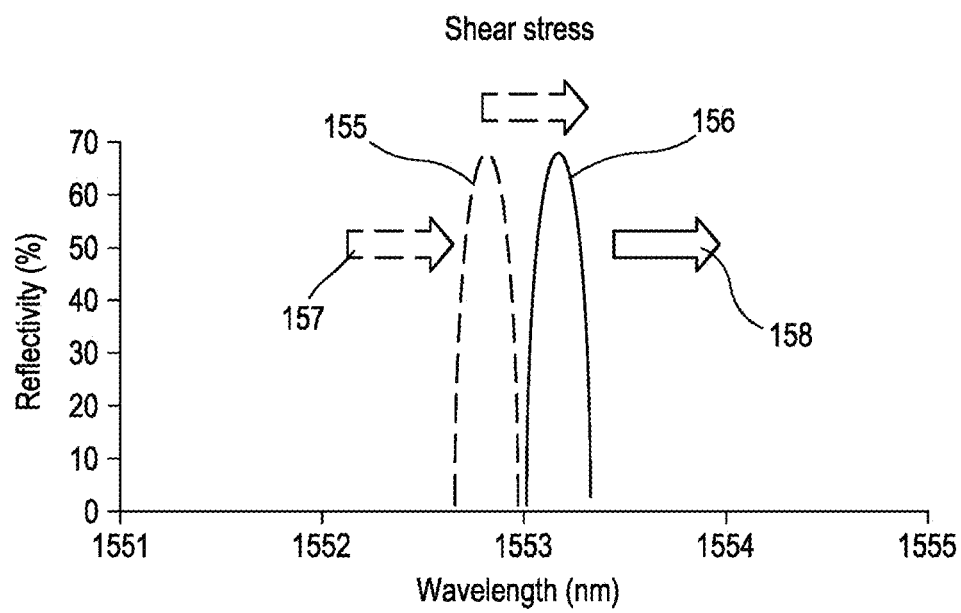

FIGS. 8 and 9 show a reflectance peak corresponding with horizontally polarised light 155 and a reflectance peak 156 corresponding with vertically polarised light. As indicated by arrows 159, 160 (in FIG. 8) the effect of a transverse load is to increase the wavelength separation between the reflectance peaks 155, 156. The effect of a shear stress is to increase the wavelength separation between the reflectance peaks 155, 156, as shown by the arrows 157, 158 (in FIG. 9) which illustrate both wavelengths peaks increasing in wavelength in response to a shear load.

Figure 10:
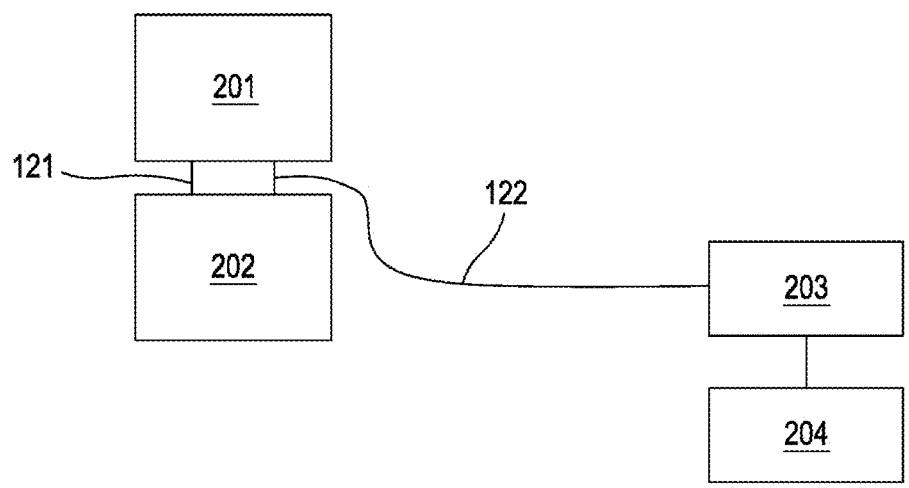
FIG. 10 is a schematic of a test arrangement for characterising the response of a patch device to transverse loading.

FIG. 10 illustrates a characterisation arrangement that has been used to determine the response of transducer FBGs 107 to transverse loading. The patch 121 in which the transducer FBG 127 is embedded is placed between a support 202 and a load 201 (e.g. a weight). The optical fibre 122 is connected to an interrogator 203, which determines the spectral response of the fibre (and FBG in the patch 121). The interrogator outputs data derived from the spectral response to a computer, which is configured to use the data to determine a relationship between the applied load and the response of the transducer FBG in the patch 121.

The one or more optical fibres 115 of the optical fibre assembly 110 may also be embedded in a patch or matrix.

The optical fibres 115 may be embedded in the same patch or matrix 121 in which the optical fibre 122 of the pressure sensor 120 is embedded, forming a single patch or system comprising an optical fibre assembly 110 for measuring one or more physiological parameters, and a pressure sensor 120 (which may comprise part of the optical fibre assembly 110). The optical fibres 115 may be embedded in the matrix 121 at or proximate one of the opposing largest faces of the matrix or patch 121 (i.e., near an outer surface). This enables delivery of light to and/or reflection of light from skin of an individual by placing the said largest face of the matrix 121 near to or in contact with skin of the individual to measure a physiological parameter using the optical fibres 115 of the optical fibre assembly 110.

Alternatively, the optical fibres 115 may be embedded in a separate patch or matrix. The patch or matrix may be or comprise the same material as the patch 121 of the pressure sensor 120, or may comprise a different material. The material of the separate patch may be or comprise a clear, transparent or translucent material. The optical fibres 115 may be embedded near or at an outer surface of the separate patch or matrix to enable delivery of light to and/or reflection of light from skin of an individual to measure a physiological parameter using the optical fibres 115 of the optical fibre assembly 110. The separate patch or matrix may be connected or adhered (e.g., using adhesive) to the matrix 121 of the pressure sensor 120 to form a single 'patch' or system comprising an optical fibre assembly 110 for measuring one or more physiological parameters, and a pressure sensor 120. The outer surface of the separate patch or matrix is configured to be placed near to or in contact with skin of an individual to measure a physiological parameter using the optical fibres 115 of the optical fibre assembly 110.

The matrix or patch may protect and support the optical fibres 115 of the optical fibre assembly 110. The matrix may also serve to reduce motion artefacts (by inhibiting movement of the optical fibres 115) typically introduced by movement of optical fibres during measurement of physiological parameters.

The end of one or more of the optical fibres 115 embedded in the matrix may comprise a cleaved end. The cleaved end may be oriented at an angle of between from 30° to 60° relative to the longitudinal axis of the optical fibre 115, and preferably may comprise a cleaved face oriented at an angle of 45°. The cleaved end may increase optical coupling efficiency of the optical fibres 115 to skin of the individual, and may also enable sensing of reflected or transmitted light away from the longitudinal axis of the optical fibre 115.

The matrix material or patch in which the optical fibres 115 of the optical fibre assembly 110 are embedded may comprise or contain scattering elements. The scattering elements may be configured to diffusely scatter light delivered by one or more of the optical fibres 115 before the light reaches skin of an individual. By diffusely scattering the light from one or more of the optical fibres 115, the scattering elements may provide a greater tolerance for non-ideal positioning of the matrix (and as a result, the optical fibres 115) relative to skin of the individual during measurement of physiological parameters. Light from the optical fibres 115 may be scattered over a larger area of skin of the individual than by direct illumination from an optical fibre 115, making the optical fibre assembly 110 more sensitive to light reflected from skin of the individual in a non-specular direction. In this way, the sensitivity of measurement quality to relative positioning of optical fibres 115 collecting light from skin of the individual may be reduced (e.g., direct contact of the matrix material with skin of the individual may not be necessary to achieve accurate, reliable results). This may reduce or remove any skill element in applying the optical fibre assembly 110 correctly to skin in order to obtain reliable measurements.

The scattering elements may be or comprise particles (e.g., micro or nano-sized particles) embedded in the matrix material. The scattering elements may additionally or alternatively be or comprise gaseous bubbles (e.g., air) trapped in the matrix material. The gaseous bubbles may be introduced into the matrix or patch material during manufacture, for example by stirring an epoxy matrix material prior to curing.

Alternatively or additionally, a separate scattering layer may be provided to diffusely scatter light from one or more optical fibres 115 before the light reaches skin of an individual. The scattering layer may, in use, be disposed between an outer surface of the matrix in which the optical fibres 115 are embedded and skin of the individual. The scattering layer may be or comprise a thin layer of material (e.g., polymer or epoxy material similar to the matrix or patch material, comprising or containing scattering elements) or a thin layer of fabric (e.g., a translucent white fabric layer). In this way, the optical fibre assembly 110 is in indirect contact with skin of the individual, rather than direct contact with skin of the individual.

By providing a single system 100 comprising an optical fibre assembly 110 for measuring one or more physiological parameters in conjunction with a pressure sensor 120, reliability of measurements for the physiological parameters can be improved. As discussed previously, an optimal pressure range may exist for obtaining physiological measurements using optical sensors. If the pressure sensor 120 determines that the pressure applied to skin of an individual via the optical fibre assembly 110 is not within the optimal range (e.g., the pressure is too high or too low), the optical fibre assembly 110 may be configured not to collect measurements of a physiological parameter until the pressure returns to the optimal range.

Alternatively, the optical fibre assembly 110 may be configured to collect data at all applied pressures measured by the pressure sensor 120, but post-processing of the collected data may indicate to a user which data may be considered reliable and/or accurate (e.g., which physiological parameter data was collected by the optical fibre assembly 110 at times when pressure measured by the pressure sensor 120 was within the optimal range). The data collected when the applied pressure was not within the optimal range may be discarded, or weighted less heavily.

The system 100 may be implemented in a handheld probe to be used, for example, in a clinical setting. The system 100 may enable medical staff to rapidly obtain accurate, reliable readings of physiological parameters measurable using optical sensors. Medical staff may not need to rely solely on experience to manually apply an optimal pressure for data collection using the system 100. This may be because the optical fibre assembly 110 is configured to collect data only when the pressure measured by the pressure sensor is optimal for measuring physiological parameters (as discussed above). Alternatively, the handheld probe may further comprise an indicator (e.g., a light or sound alert) which indicates to the user that a magnitude of pressure applied to the optical fibre assembly 110 is within an optimal range for data collection. A handheld probe comprising the system 100 may be used to quickly and accurately measure, for example, capillary refill time in the foot of a diabetic patient to as a screening method to prevent diabetic foot ulcers.

The system 100 as described above may be integrated with a textile, for example by knitting, weaving, embroidering or threading the optical fibres 115 of the optical fibre assembly 110 through the textile, or more simply by attaching the optical fibres 115 to the textile, for example using adhesive, stitching (e.g. tacking stitches with a further yarn), or fixing with heat fusible yarn. Additionally or alternatively, in embodiments comprising an optical fibre pressure sensor, the optical fibre 122 of the pressure sensor 120 may be integrated with a textile in a similar manner. The system 100 may be integrated into a textile by embroidering a channel onto the surface of the textile, and then fixing the optical fibres 115, 122 in the channel, for instance with adhesive and/or heat fusible yarn. At least one transducer FBG 127 (and optional strain compensation FBG 147) may be positioned between each two points of attachment with the fabric.

One configuration of textile and pressure sensing optical fibre 122 is a textile formed into a tube, into which the pressure sensing optical fibre 122 is inserted. If the textile comprises heat fusible yarn, the pressure sensing optical fibre 122 may be fixed in place by fusing the yarn at a number of locations along the optical fibre 122 to form points of attachment with the optical fibre 122. The optical fibres 115 of the optical fibre assembly 110 may be fixed in place in a similar manner.

In some embodiments the patch or matrix may be formed from a heat fusible yarn. For example, the optical fibres 115, 122 may be woven or knitted into a textile comprising heat fusible yarns (or regions of heat fusible material). The patch structure may be formed around the optical fibres 115, 122 after the fibres 115, 122 have been woven or knitted into the textile by fusing the fibres 115, 122 in the region of a transducer FBG 107. In some embodiments the patch may be formed by impregnating a curable material into a textile in the region of an optical fibre 115, 122 that is woven or knitted (or otherwise integrated) with the textile.

A number of applications exist for a textile comprising the system 100. One example application is in compression bandages. The system 100 may be integrated with a textile bandage to provide a plurality of pressure measurement and physiological parameter measurement locations along the length of the bandage. The integration of the system 100 into the compression bandage enables fitting of the compression bandage to be optimised. Optimisation of fitting the compression bandage is required to make sure that the compression bandage is fitted tightly (to apply the correct pressure) without being fitted too tightly (and applying too much pressure). Correlating readings from the pressure sensor 120 with readings from the optical fibre assembly 110 may be utilised to identify whether the applied pressure is optimal or not. For example, in the case of a compression bandage applied to aid wound healing, correlating readings from the pressure sensor 120 with readings from an optical fibre assembly 110 configured to measure $S_PO_2$ may quickly indicate whether the applied pressure is high enough to reduce or occlude blood flow to the wound area (which would reduce the rate of wound healing). If the correlated readings indicate that the applied pressure is reducing or occluding blood flow to the wound area, the compression bandage can be refitted to ensure an optimal application of pressure.

Significantly, optical fibre pressure sensors as described above are relatively insensitive to bending, and may include compensation for both temperature and longitudinal strain, which may arise from stretching of the fabric of the bandage. Embodiments in which the transducer FBG 127 is a HiBi FBG can additionally measure shear stress at the patch 121, which is also likely to have a role in optimal healing.

A textile comprising the system 100 comprising an optical fibre assembly 110 configured to measure $CO_2$ emission from skin may be used to identify either a likelihood of developing, or early onset of, pressure ulcers in bedbound patients, prior to full development of bedsores by the patient. An optimal contact pressure may be required to obtain reliable, accurate readings of $CO_2$ emission from skin using an optical fibre assembly 110 in the textile. The contact pressure may be measured by the pressure sensor 120 in the textile. In some embodiments the measurement of $CO_2$ emission may be similar to the measurement of a capillary refill. The system may automatically detect pressure events that may be suitable for measurement of $CO_2$ emission that is characteristic of increased risk of bedsores. A suitable pressure event may be a contact pressure exceeding a predetermined threshold (e.g. at least 10 kPa, 15 kPa or 20 kPa) for a predetermined period (such as 100 s, 200 s, 300 s 400 s etc). A rise in $CO_2$ emission in response to this sort of pressure event may be a biomarker for bedsores (Mirtaheri, Peyman, et al. "A review of the role of the partial pressure of carbon dioxide in mechanically loaded tissues: the canary in the cage singing in tune with the pressure ulcer mantra." Annals of biomedical engineering 43.2 (2015): 336-347). In some embodiments the rate of increase in CO2 emission when the tissue is loaded may be used as a biomarker.

The system 100 may be configured to measure a physiological parameter indicative of circulatory health (e.g. capillary refill or similar). The system may be configured to perform a capillary refill measurement. The capillary refill may be detected by optical fibre based PPG (Photoplethysmography), examples of which are described below.

The system 100 may also be incorporated into other compression garments to improve user adherence. Monitoring compression applied by a compression garment enables the fit to be adjusted to apply a more optimal amount of pressure, which may result in improved healing rates and better patient outcomes. Often compression garments are tightly fitting and some wearers may find this uncomfortable. By correlating readings from the pressure sensor 120 and the optical fibre assembly 110, the compression garment can be fitted or altered to apply optimal pressure (that the wearer considers comfortable) whilst still providing one or more physiological or medical benefits.

The system 100 may also be used in other applications. For example, the system 100 may be incorporated into compression garments such as those used in recovery from sports, such as T-shirts, shorts, leggings, socks etc.

The system 100 may also be incorporated into a loose fitting garment in which measurements of physiological parameters measured by the optical fibre assembly 110 are only recorded when an appropriate pressure is applied, as measured by the pressure sensor 120. The appropriate pressure may be applied by the wearer manually applying pressure to a portion of the loose fitting garment with one or both hands, or by pressing the garment against a surface (e.g., leaning back in a chair to apply pressure to a part or whole of the wearer's back).

An example embodiment of the system 100 is described below in relation to measuring blood oxygen saturation ($S_pO_2$).

Blood oxygen saturation level indicates the percentage of oxygenated haemoglobin molecules in the arterial blood. This metric has been identified as an indicator of risk in chronic disease of the circulatory and respiratory system and is required to be continuously monitored during, for example, anaesthesia. Pulse oximetry is a non-invasive method to detect the blood oxygen saturation level ($S_pO_2$) which was first introduced in 1983 and accepted as a standard procedure in administrating general anaesthetic in the US in 1987.

The $S_pO_2$ measured by pulse oximetry is defined as the ratio between the oxygenated haemoglobin ($HbO_2$) over the total haemoglobin ($HbO_2$+Hb)

$$S_pO_2 = \frac{HbO_2}{HbO_2 + Hb} \times 100\%$$

Since the absorption spectra of $HbO_2$ and Hb are different, pulse oximetry uses photoplethysmography (PPG) at two different wavelengths (usually red and near-infrared) to obtain the $S_pO_2$ value. The PPG signal is the intensity of the light penetrating or reflected by body tissues, which consists of a small pulsatile component (AC) and a large static component (DC). The light absorption of arterial blood causes the pulsatile component in PPG signals whilst the light absorption of steady component (due to venous blood, bone, skin, hair and tissue) gives rise to the DC component. Pulse oximetry calculates $S_pO_2$ from the absorbance ratio (R) which is derived from the ratios of pulsatile components of PPG signals ($I_{AC}$) to static components of PPG signals ($I_{DC}$)

$$R = \frac{I_{AC,red}/I_{DC,red}}{I_{AC,infrared}/I_{DC,infrared}}$$

Pulse oximetry can be performed in transmission and reflectance geometries. Transmission mode is limited to extremities such as the finger, toe or earlobe whereas reflectance mode provides greater flexibility of body site.

However, there are challenges in using typical optical fibre sensors for pulse oximetry. Such challenges include inefficient light coupling at the tissue interface, and motion artefacts occurring when the optical fibres move relative to the tissue surface. To counteract motion artefacts, typical optical fibre sensors need to be in contact with the skin which requires tight fitting garments or straps, making them impractical for long term use. It is also known that the contact force between tissue and sensor can affect the accuracy of $S_pO_2$ values in both transmission and reflectance modes. Insufficient contact pressure can cause a weak PPG signal whilst too high a pressure will block the blood circulation and deform the PPG. A range of contact force exists to generate optimal PPG signals with salient pulsatile components.

Figure 11A:
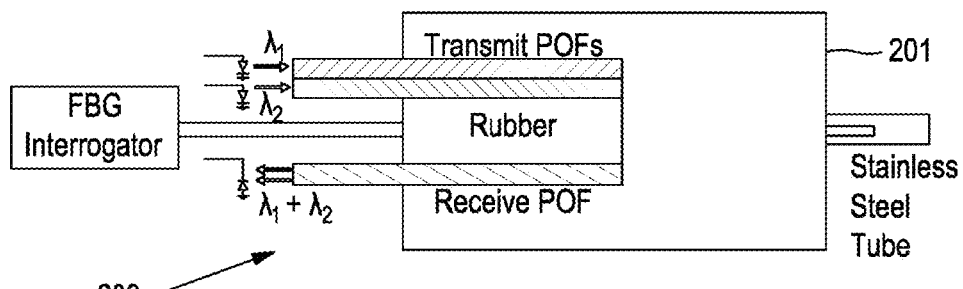
FIGS. 11A and 11B are schematics illustrating a patch sensor comprising an optical fibre assembly and an optical fibre pressure sensor according to an embodiment.
Figure 11B:
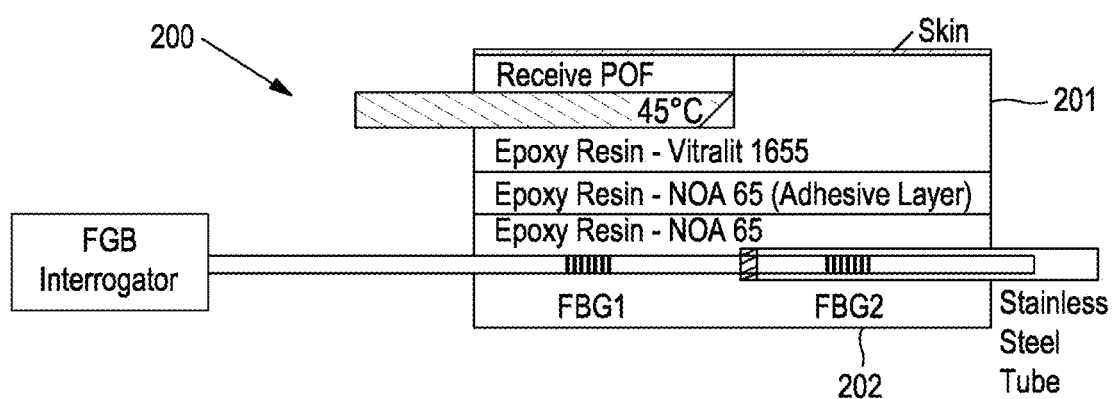

FIGS. 11A and 11B show an embodiment of the system 100 as a probe 200 configured to measure blood oxygen saturation. The probe 200 is a patch comprising two patches, a first patch 201 comprising a pulse oximeter and a second patch 202 comprising a FBG pressure sensor. The two patches 201, 202 are glued together using epoxy resin (NOA-65). The pulse oximeter comprises three 500 μm diameter plastic optical fibres or POFs (Asahi Kasei DB-500), two of which are configured to deliver light to skin (each fibre delivering light at a different wavelength) and one of which is configured to receive light reflected from skin. The end of each POF embedded in the epoxy patch 201 is 45° cleaved to increase the light reflecting from the side of the angled optical fibre, which allows for sensing away from the axis of the POF.

The material of the pulse oximeter patch 201 is epoxy resin (Vitralit 1655) which is a bio-compatible material. Exposed to UV light, the epoxy resin is cured in a mould into a 20×10×2 mm cuboid. There is one 3.5×10×1 mm slot on the top surface of the epoxy cuboid generated by polishing. Three POFs with 45° cleaved ends are set into this slot, and then fixed by filling and curing the epoxy resin (Vitralit 1655). Black rubber (2 mm thick) may be placed on the surface of the epoxy patch 201 between the transmit and receive POFs (as shown in FIG. 11A) to prevent light passing directly from the source to the detector, as this would affect $I_DC$ and therefore the $S_pO_2$ value.

For contact pressure sensing, two FBGs separated by 6 mm are written into a 125 μm diameter photosensitive silica optical fibre (PS1250 from Fibercore) using a UV inscription method. Encasing an FBG (FBG1) in epoxy transduces a transverse load into an axial strain. However, temperature changes cause shifts to the Bragg wavelength and therefore a temperature reference FBG (FBG2) is included to compensate. The temperature reference FBG is shielded in a stainless steel tube (outer diameter 0.56 mm, inner diameter 0.305 mm, Coppers Needle Works LTD, UK) to make it sensitive to only temperature. FIG. 11B details the FBG pressure sensor patch 202. FBG1 is covered by the epoxy rectangular cuboid to measure the pressure, whilst FBG2 is protected by the stainless steel tube to compensate for the temperature. The patch 202 is made of epoxy resin (NOA-65) which has a lower Young's Modulus (137.9 MPa) than Vitralit 1655. The epoxy resin of the patch 202 is cured in the same mould as the pulse oximeter patch 201 into a 20×10×2 mm cuboid after exposure to UV light. As can be seen in FIGS. 11A and 11B, the optical fibre of the pressure sensor patch 202 is connected to an FBG interrogator (discussed below).

Figure 12:
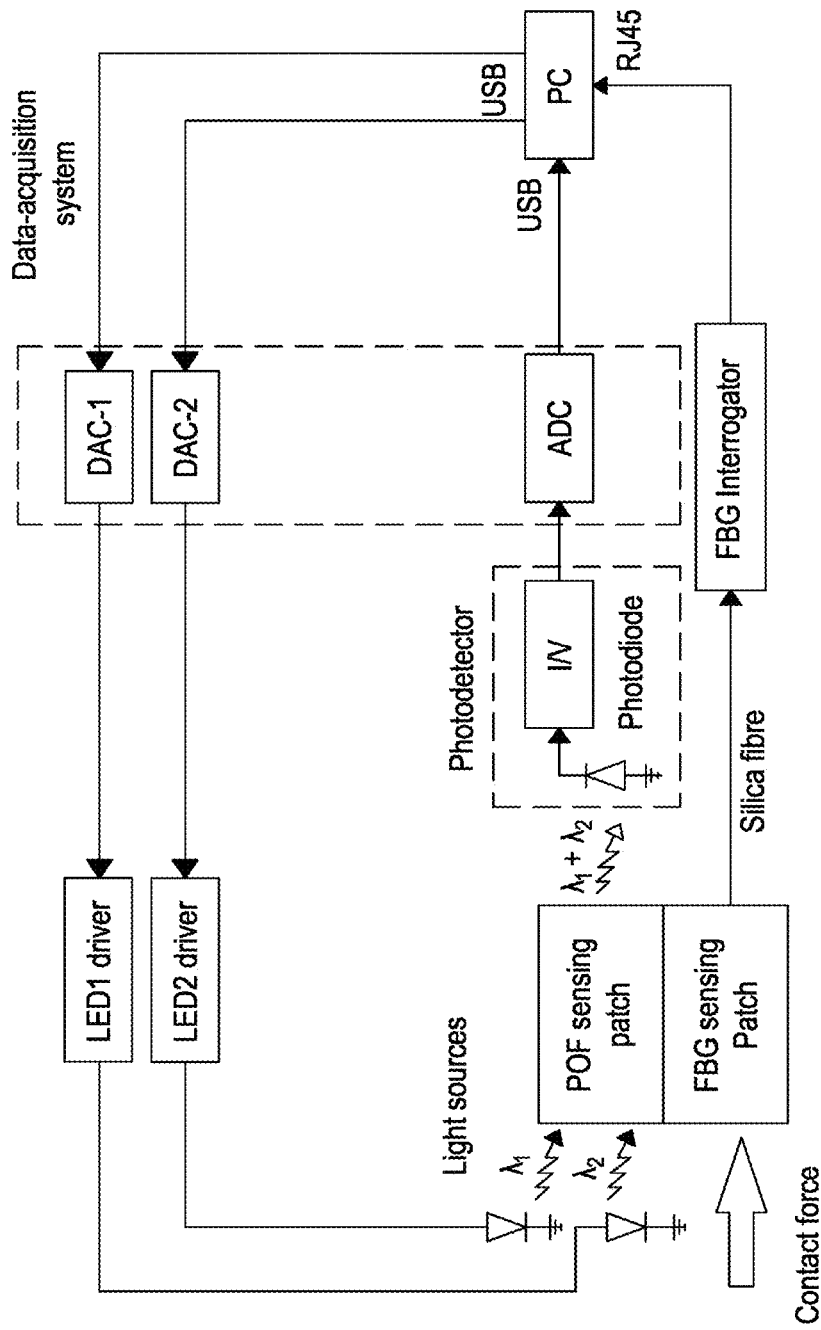
FIG. 12 is a schematic illustrating an optoelectronic system configured for use with the patch sensor of FIGS. 11A and 11B.

FIG. 12 shows a block diagram of an example opto-electronics system used in conjunction with the probe 200. The reflectance pulse oximetry sensor part consists of two LEDs operating at different wavelengths: one at λ=660 nm (e.g. a Thorlabs fibre-coupled LED M00408143); and the other at λ=850 nm (e.g. a Thorlabs fibre-coupled LED M00290109). Two LED drivers (e.g. Thorlabs LEDD1B) control the light level and modulation. A photodetector (e.g. Thorlabs PDA36A-EC 350-1000 nm) has an amplifier with switchable gain set to 2.38×10⁶ V/A. All components in this example use SMA connectors, but other connectors may be used. A data acquisition system (e.g. National Instruments myDAQ, 16 bits, 20 kHz sampling) has two ADC channels and two DAC channels. One ADC channel is used to read the output of the photodetector whilst two DAC channels are used to control the LEDs. The overall opto-electronics system is computer controlled (e.g. by Labview, version 2015 SP1). Time-division Multiple Access (TDMA) is used to read both PPG signals using the single photodetector. Two 500 Hz square wave (25% duty cycles, 180° phase difference) are used to drive the two LEDs whilst the output of the photodetector is sampled at a sampling frequency of 20 kHz.

The specific features of this system are merely exemplary, and other wavelengths for the LEDs may be used, other gain settings may be used for the photodetector, and other ADC arrangements (e.g. non TDMA, different sampling rates etc) may be used to read the output of the photodetector.

The FBG response in this example embodiment is measured using a SmartScan FBG interrogator (Smartscan, Smartfibres, UK) also shown in FIG. 12. The SmartScan FBG interrogator is a high speed interrogator with 4 channels which is capable of scanning at a scan frequency of 2.5 kHz for the entire wavelength range from 1528 to 1568 nm (i.e., over 40 nm with a resolution of 16 pm). The maximum scan frequency of the FBG interrogator with reduced wavelength range is 25 kHz. In FIG. 12, I/V means current to voltage converter, DAC means digital to analogue converted, ADC means analogue to digital converter, and PC means personal computer. The particular features of the FBG interrogator are merely exemplary, and other scan frequencies and wavelength ranges may be used.

Figure 12A:
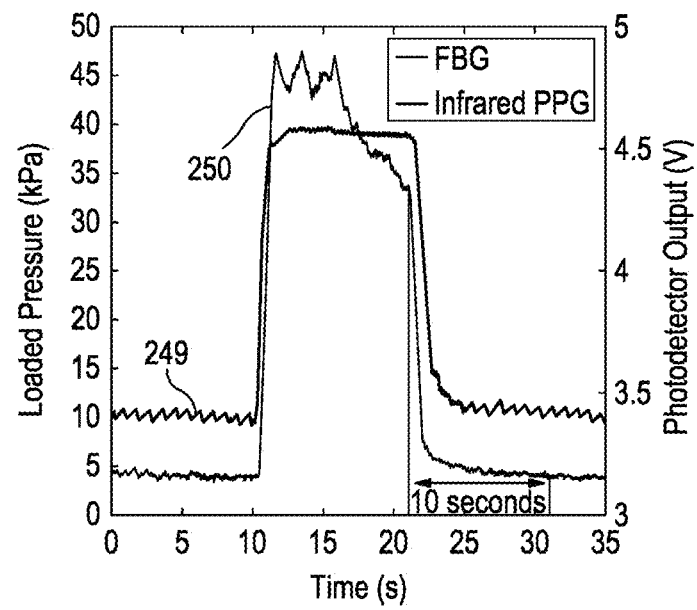

FIG. 12A shows the relationship between the intensity of infrared light (curve 249) reflected from a finger of an individual applying a force on the FBG pressure sensor 202 of FIGS. 11A and 11B, and loaded pressure (curve 250) recorded by the FBG pressure sensor 202. The loaded pressure curve 250 can be used to isolate each capillary refill process during the ten seconds following the point where the loaded pressure is released. As the pressure is manually applied by the individual in the case of FIG. 12A, the pressure signal is not stable between 11.8 to 21.7 seconds. An automated pressure loading system may be utilised to stabilise the pressure signal.

Referring to FIG. 12A, from 0 to 10 seconds there is no external pressure applied on the finger, and both pressure sensor output and the photo-detector output stay constant at a certain DC level (baseline). Then the light intensity rapidly increases in accordance with the pressure change that arises from the applied pressure (from 10.5 to 11.7 second). After the pressure is removed (at approximately 21 seconds), the output pressure sensor rapidly returns to the baseline whilst the reflected light intensity takes a longer time (CRT) to return the baseline. From the results presented in FIG. 12A, it can be observed that the DC component of the reflectance PPG signal is relatively constant after taking off the loaded pressure (apart from the oscillating heart rate signal). Therefore, a horizontal linear fitting line of the reflectance PPG DC component can be used as the baseline in CRT measurements. However, on occasion, motion artefacts, ambient light changes and physiological changes will affect this baseline. In this case, normalisation of the extracted refilling curves is used to eliminate the impact of value changes in the baseline:

$$I_n = \frac{(I_{max} - I_{min})}{(I - I_{min})}$$

$I_n$ is the normalized light intensity of the reflected light signal, $I_{max}$ is the maximum light intensity, Imin is the minimum light intensity and I is the original reflected light intensity.

Figure 12B:
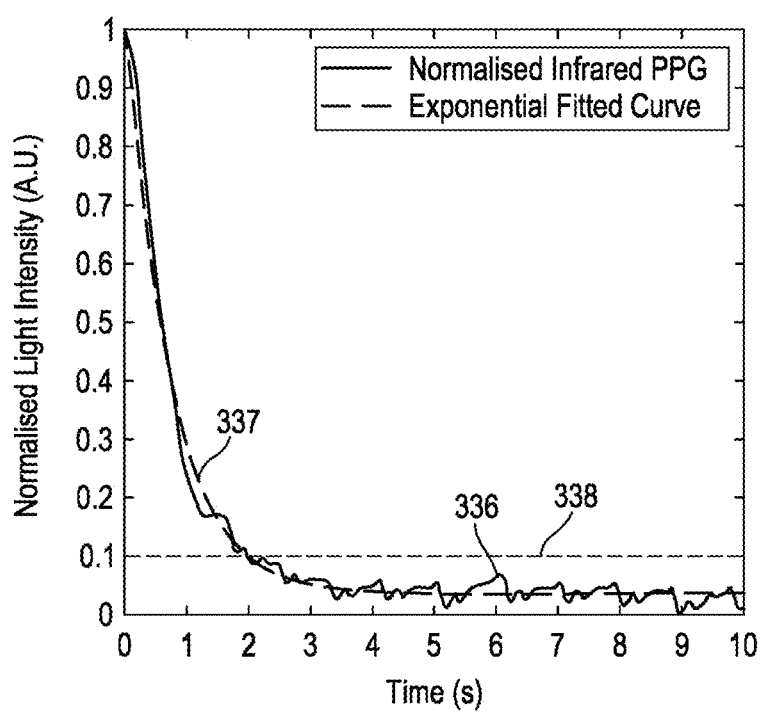

In FIG. 12B, curve 336 is the normalised isolated refilling curve, and curve 337 is the exponential fitting curve created according to the exponential fitting function:

$$y = e^{A*I_n} + B_0$$

x is the normalized light intensity of the reflected light signal, A is the power of the exponential factor and $B_0$ is the baseline of the exponential fitting curve. The time taken for the light intensity to drop to a 10% threshold of the initial value above the baseline is the estimated CRT.

The R square value of the exponential regression system is 0.985, and the root mean square error (RMSE) value between the normalised infrared PPG and the exponential fitting curve is 0.024. Line 338 is the threshold applied for CRT estimation.

In FIG. 12B, the isolated capillary refill process is represented by the high R square value (0.985) exponential regression model. Consequently, the order of the exponential regression curve can reflect the time of capillary refilling. In order to demonstrate the capability of using the order of exponential fitting curves to measure CRT, the orders of exponential regression model were compared to the estimated CRT calculated by using the threshold method.

All PPG signal processing was carried out in MATLAB, version R2016a. The FBG signals were processed using the software SmartScan V3.2.0 (Smart Fibres, UK). The Bragg peaks of two FBGs in the reflection spectrum were detected using the peak detection function of the SmartScan V3.2.0.

For the pulse oximeter, motion artefacts will affect the quality of the PPG signals collected. Thus, before using the obtained PPG signals to calculate the $S_PO_2$, the quality of the obtained PPG signals is obtained. There are several signal quality indices (SQIs) which may be utilised in verifying the quality of PPG signals. Two are considered here: Perfusion Index (PI) and Skewness Index (SI), which is associated with corrupted PPG signals revealing more detailed morphology of the pulse waveform.

PI is the ratio of the pulsatile to non-pulsatile blood volume in peripheral tissue. A small PI indicates a weak pulsatile signal.

$$PI = \left[\frac{Y_{max} - Y_{min}}{\bar{x}}\right] \times 100$$

Y is a low-pass filter PPG signal with a cutoff frequency of 5 Hz. $\bar{x}$ is the absolute statistical mean of the raw PPG signal.

SI is a measure of the symmetry (or lack of symmetry) of a probability distribution. If the pulsatile PPG signal is strong and clear, SI is positive, and vice versa.

$$SI = 1/N \sum_{i=N}^{N} (x_i - \hat{\mu}_x/\sigma)^3$$

N is the number of samples in the PPG signal. $\hat{\mu}_x$ and $\sigma$ are the mean and standard deviation of $x_i$ respectively. If the pulsatile component of the PPG signals is not clear enough to identify systolic and diastolic peaks, the SI value is negative.

For high quality PPG signals, the PI value is high and the SI value is positive. As PPG signal quality decreases, both PI and SI values decrease. Based on empirical experience, an example PT value indicating good quality PPG signals is typically larger than 0.4%. In some embodiments a threshold of PI may be set at 0.4% and a threshold of SI set at 0, the combination distinguishing good quality PPG signals from poor quality PPG signals.

To calculate the $S_pO_2$ value it is necessary to extract the absorbance ratio (R) and then use the following empirical equation.

$$S_pO_2 = 110 - R \times 25$$

Although a more accurate relationship could be obtained by comparison with blood gas analysis, taking blood samples was beyond the scope of the ethical approval.

All PPG signal processing in these example embodiments were carried out in MATLAB, version $^{R2}$016a. The FBG signals are processed using the software SmartScan V3 2.0. The Bragg peaks of two FBGs in the reflection spectrum are detected using the peak detection function of the SmartScan V3 2.0.

In order to test the temperature response of FBG1 and FBG2, and the ability of FBG2 to compensate for temperature, both FBG1 and FBG2 were placed in an oven (Binder ED53, Germany) and tested by heating the oven from room temperature to 49°. Cooling of the oven was achieved by allowing the oven, with the door open, to naturally reduce in temperature back to the laboratory ambient temperature.

Figure 13:
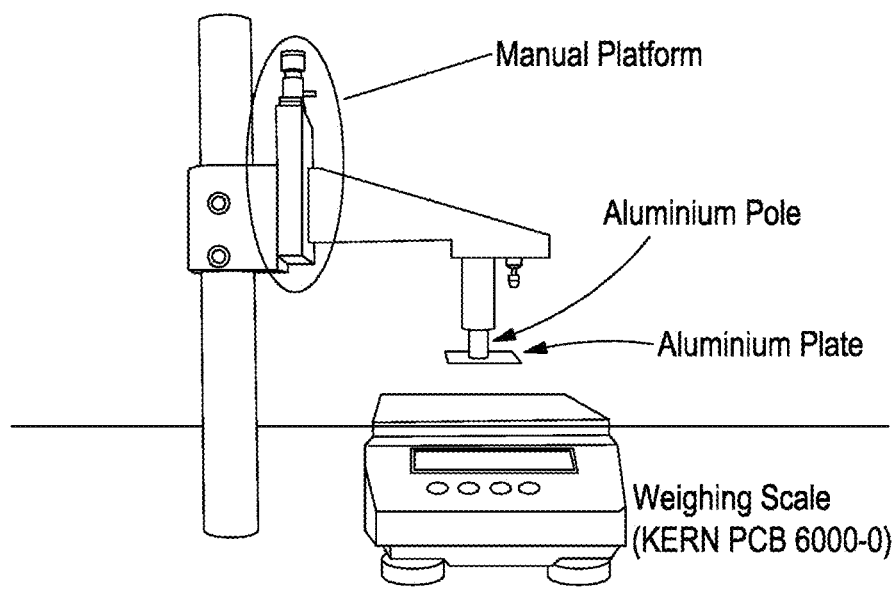
FIG. 13 illustrates an experimental setup used to characterise the patch sensor of FIGS. 11A AND 11B.

The contact pressure response is demonstrated using the setup shown in FIG. 13. By screwing a manual platform to lift or lower an aluminium pole and plate, pressure on the pressure sensor patch 202 can be adjusted. A weighing scale (KERN PCB 6000-0) beneath the pressure sensor patch 202 records the force loaded on the patch 202 and is used for characterising the performance of the FBG sensor.

A comparative test was performed using the probe 200 and a commercial PPG Pulse Oximeter (PO) device (Masimo Radical-7) by simultaneously measuring the $S_pO_2$ level of index fingers and middle fingers of ten volunteers. Preliminary results were obtained from a single volunteer to assess signal return and quality. A desaturation event was generated by a seated volunteer 1) breathing normally to obtain a baseline; 2) then breathing out for 10 to 15 seconds; 3) then holding breath for 20 to 30 seconds and 4) then finally breathing normally again.

Figure 14:
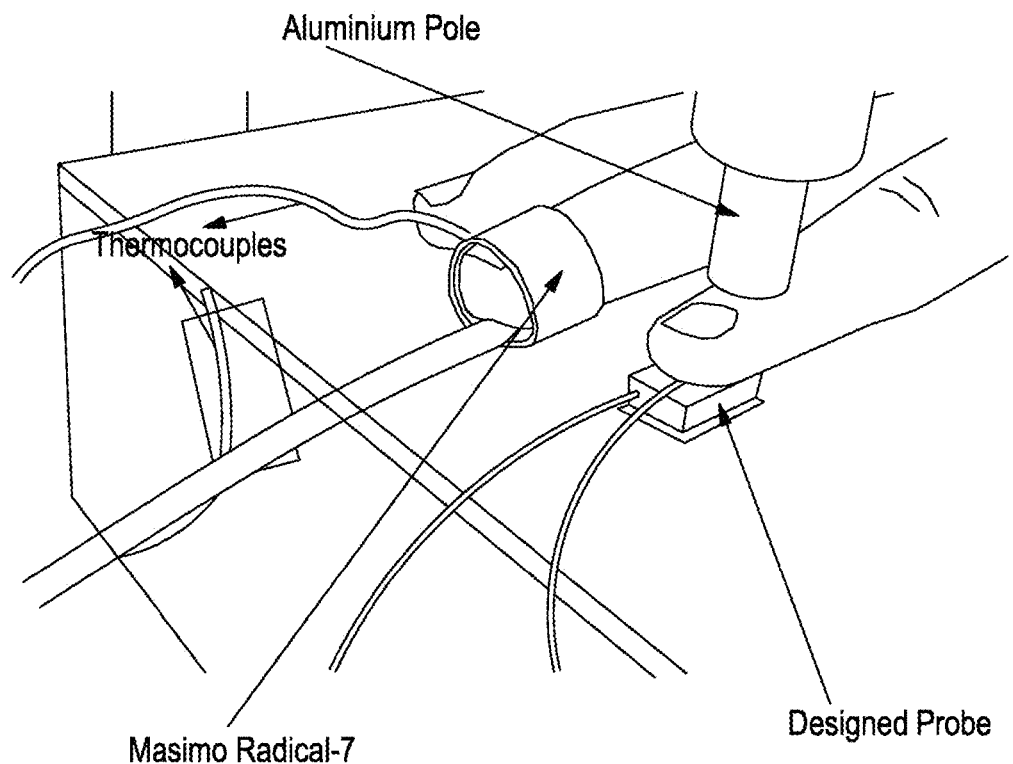
FIG. 14 illustrates further details of an experimental setup used to characterise the patch sensor of FIGS. 11A and 11B.

FIG. 14 shows the setup for the comparative testing. The pulse oximeter patch 201 and the Masimo Radical-7 recorded the $S_pO_2$ value of ten volunteers' index fingers and middle fingers respectively. The pressure sensor patch 202 recorded the contact forces applied to volunteers' index fingers at the same time. Pressure was applied in increments (approximately 7 kPa per increment) to the finger using the aluminium pole shown in FIGS. 3 and 4 using the manual screw plate until the PI was too low and the pulsatile PPG component from the reflected light could no longer be observed. The externally applied pressure exceeded 15 kPa to evacuate blood from the capillary bed as no pulsatile PPG component from the reflected light could be observed. The aluminium pole was then gradually lifted to reduce the pressure exerted on the index finger. Each volunteer repeated the experiment three times. Thermocouple sensors (shown as the mixed green and white wires in FIG. 4) were used to measure the room temperature and the index finger temperatures.

Since the value of the external applied pressure will affect the CRT measurement, an automatic pressure loading device may be incorporated with the probe 200 which can provide a fixed pressure for all subjects.

Apart from the contact pressure, temperature is an important factor in measuring blood oxygen saturation levels. The room temperature measured using the thermocouple sensors was higher than 26° C. during the comparative testing. This resulted in the temperature of the volunteers' index fingers being higher than 30° C. (measured by PICO Technology SE000). Body temperature affects blood circulation, and may cause unwanted grating period variations.

It is possible to compensate for the effects of temperature using a reference grating. In comparative testing, the integrated sensor probe was attached to the optical table tightly in order to prevent manually straining the fibre. An additional FBG sensor may be provided to compensate for any pulling of the fibre optic that could induce some strain interference on the pressure FBG.

Figure 15A:
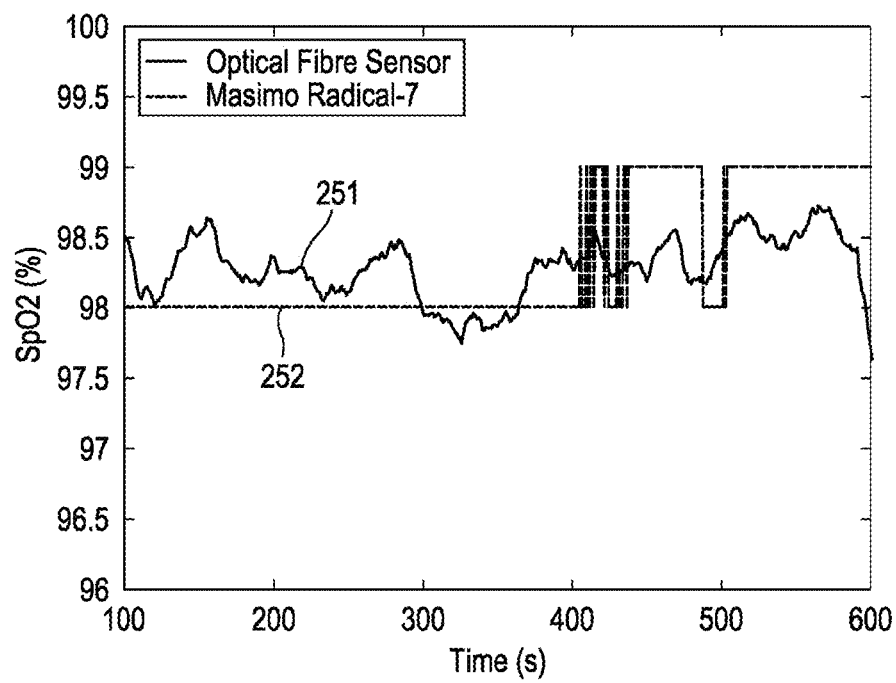
FIGS. 15A and 15B are graphs illustrating $S_PO_2$ measurements obtained using both the patch sensor and a commercial device, for a test period of 500 seconds and for a desaturation event respectively.
Figure 15B:
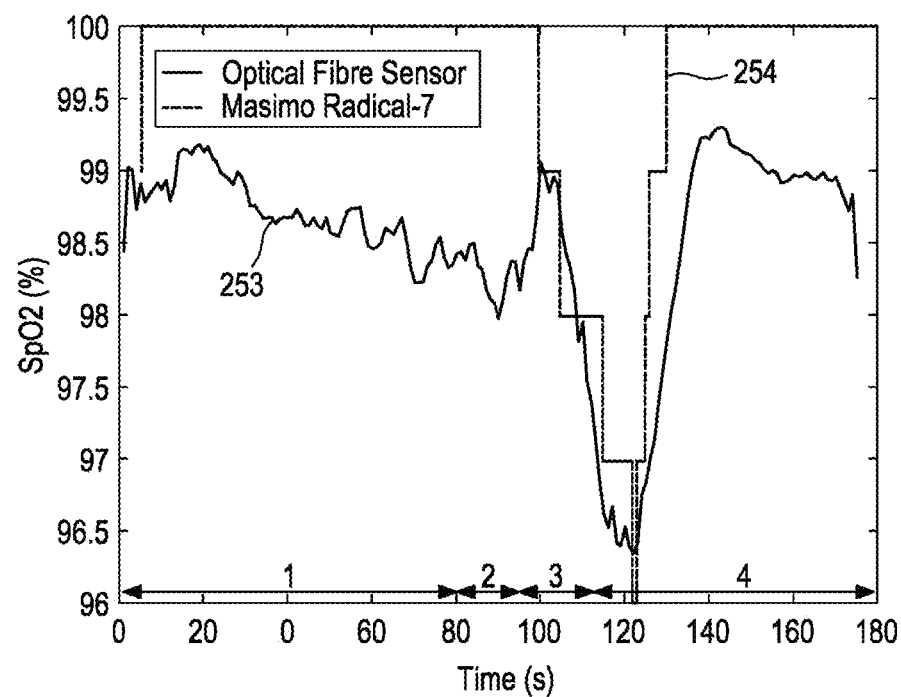

FIG. 15A is a graph showing $S_pO_2$ results obtained using the pulse oximeter patch 201 of the probe 200 from one volunteer's index finger over a test period of 500 seconds. The volunteer stood still and breathed normally for the duration of the test. The measurements 251 obtained by the pulse oximeter patch 201 are very close to the measurements 252 obtained by the commercial device (absolute error 0.443±0.466%). More significantly, as shown in FIG. 15$b$, both the pulse oximeter patch 201 and the commercial device identify a deoxygenation event induced by the desaturation process described above (absolute error 1.16±0.423%), with the curve 253 indicating the response of the pulse oximeter patch 201 and the curve 254 indicating the response of the commercial device. Stages 1 to 4 of the desaturation process are indicated on FIG. 15B. The durations of stages 1, 2, 3 and 4 were 80 s, 14 s, 19 s and 66 s respectively.

For the probe 200, the optical fibre of the pressure sensor patch 202 was fixed on the optical table tight using copper tape to avoid manually straining the fibre.

Figure 16A:
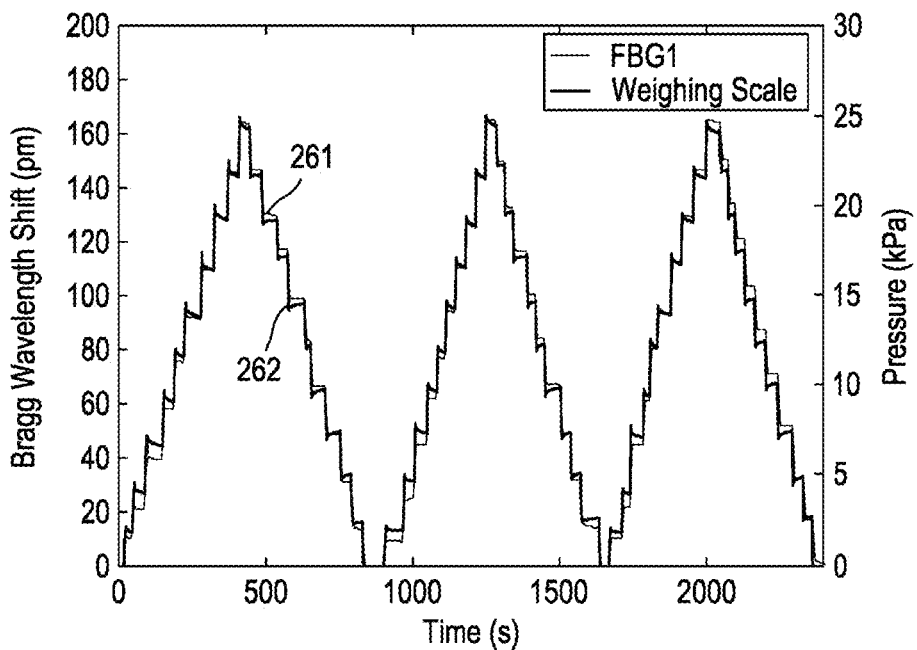
FIGS. 16A and 16B are graphs illustrating Bragg wavelength changes of the patch sensor caused by pressure loading and unloading, and the non-hysteretic linearity of that response respectively.
Figure 16B:
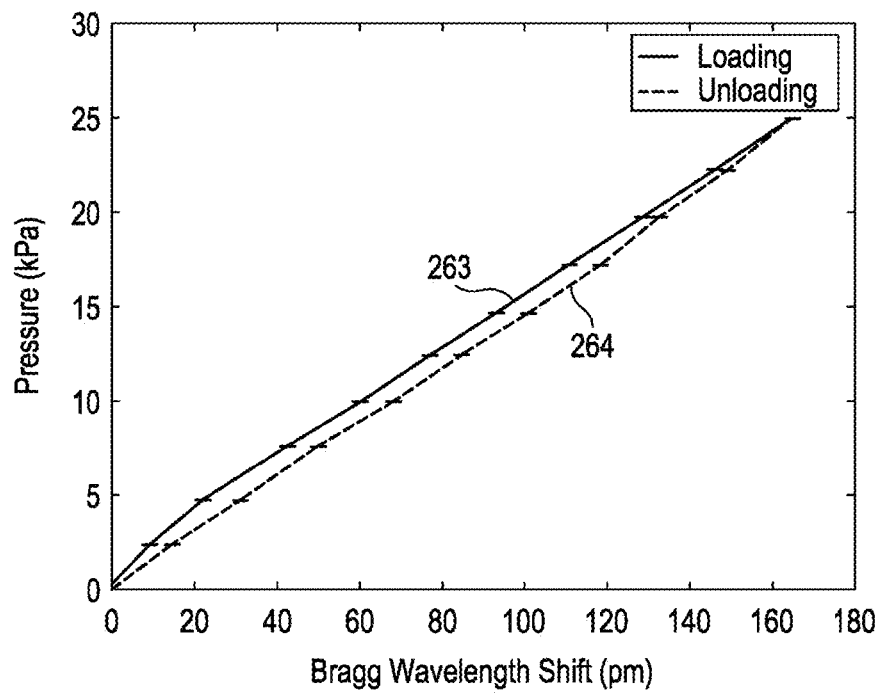

FIG. 16A shows the Bragg wavelength changes ΔFBG1 (indicated by curve 261) in the FBG1 caused by pressure loading and unloading using the system shown in FIG. 13. The pressure was incremented in steps from 0 kPa to 25 kPa, and then decremented to 0 kPa using the same step size, as shown by curve 262. This process was repeated three times. The FBG response follows that of the applied pressure. Using the data in FIG. 16A, the relationship between applied pressure and Bragg wavelength can be obtained by plotting a calibration curve as shown in FIG. 16B. This indicates that the pressure sensor patch 202 is both reliable and repeatable for pressure monitoring with negligible hysteresis, as shown by the loading curve 263 and the unloading curve 264. Based on FIG. 16B, an empirical equation of pressure calculation can be deduced.

$$\text{Pressure (kPa)} = 0.1466 \times \Delta \text{FBG1} + 0.7334$$

Figure 16C:
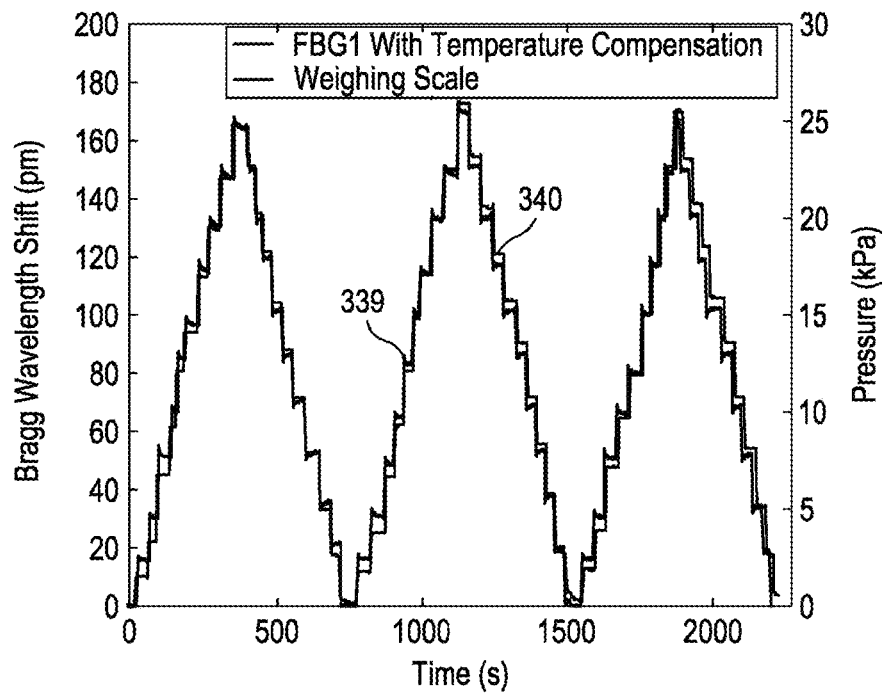
Figure 16D:
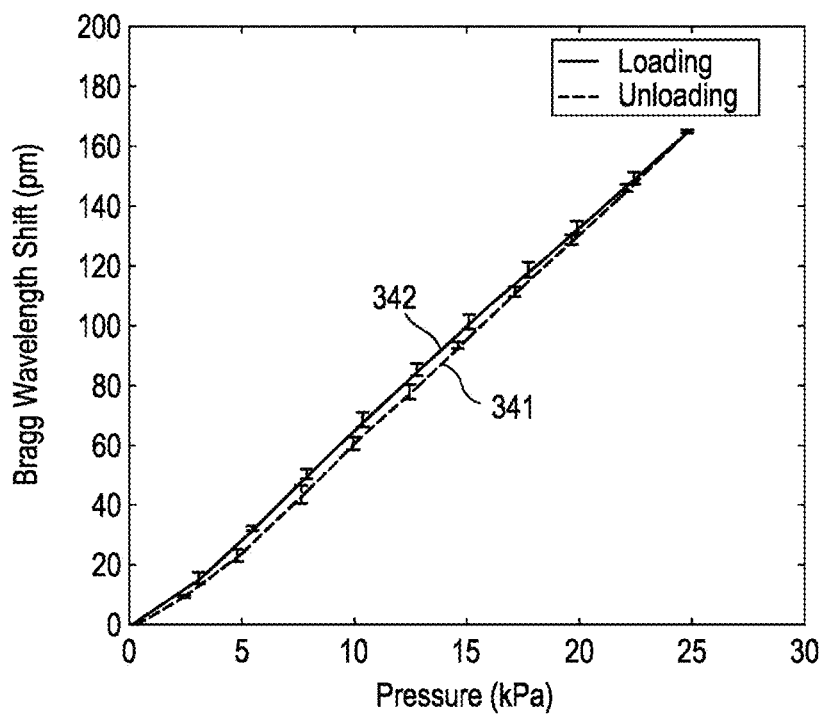

FIG. 16C shows the pressure response (curve 340) of the integrated sensor with temperature compensation, which follows that of applied pressure (curve 339). The applied pressure was increased/decreased by using the system shown in FIG. 13. The pressure was applied in steps up to 25 kPa, before unloading the pressure in steps back to 0 kPa. This loading and unloading cycle was repeated three times. FIG. 16D is a hysteresis diagram showing the dependence of the measured wavelengths shift (curve 342) upon applied pressure (curve 341) during loading and unloading. FIG. 16D shows a linear relationship, repeatable results and low hysteresis. It demonstrates that the integrated sensor is reliable for pressure monitoring. The sensitivity of the FBG sensor to pressure can be calculated as follows:

$$\text{Pressure (kPa)} = 0.1563 \times (\Delta\lambda\text{FBG1} - 2.4264 \times \Delta\lambda\text{FBG2} - 0.0111) - 0.0066$$

ΔλFBG1 is the Bragg wavelength shifts in pressure sensing FBG (FBG1) and ΔλFBG2 is the Bragg wavelength shifts in temperature compensation FBG (FBG2).

Figure 17A:
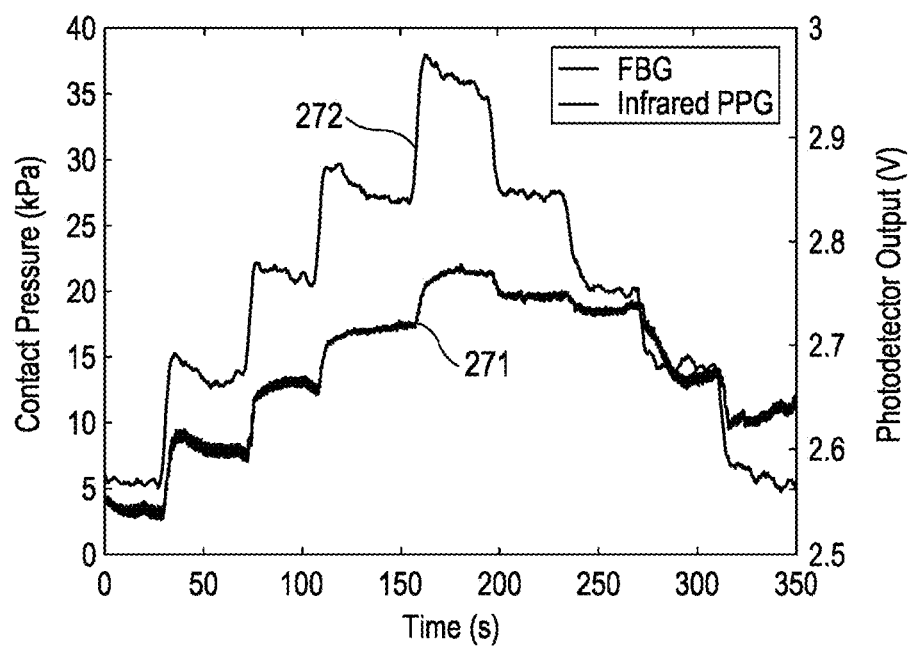
FIGS. 17A to 17D respectively show i) plots of infrared PPG signal measured by the patch sensor, and contact pressure measured by the patch sensor, ii) absolute error between $S_PO_2$ measurements obtained by the patch sensor and a commercial device, iii) Skewness Index of PPG signals and contact pressure measured by the patch sensor, and iv) Perfusion Index of PPG signals and contact pressure measured by the patch sensor.

Typical results for a single volunteer are shown in FIGS. 17A to 17D to demonstrate the response of the probe 200 to applied pressure. FIG. 17A shows the infrared PPG signal 271 as measured by the pulse oximeter patch 201 and the contact pressure curve 272 as measured by the pressure sensor patch 202. As contact pressure increases the AC component of the PPH signal decreases (i.e., a thinner line in curve 271) and the DC light level increases. This is to be expected as the blood flow is occluded and the tissue blanches.

Figure 17B:
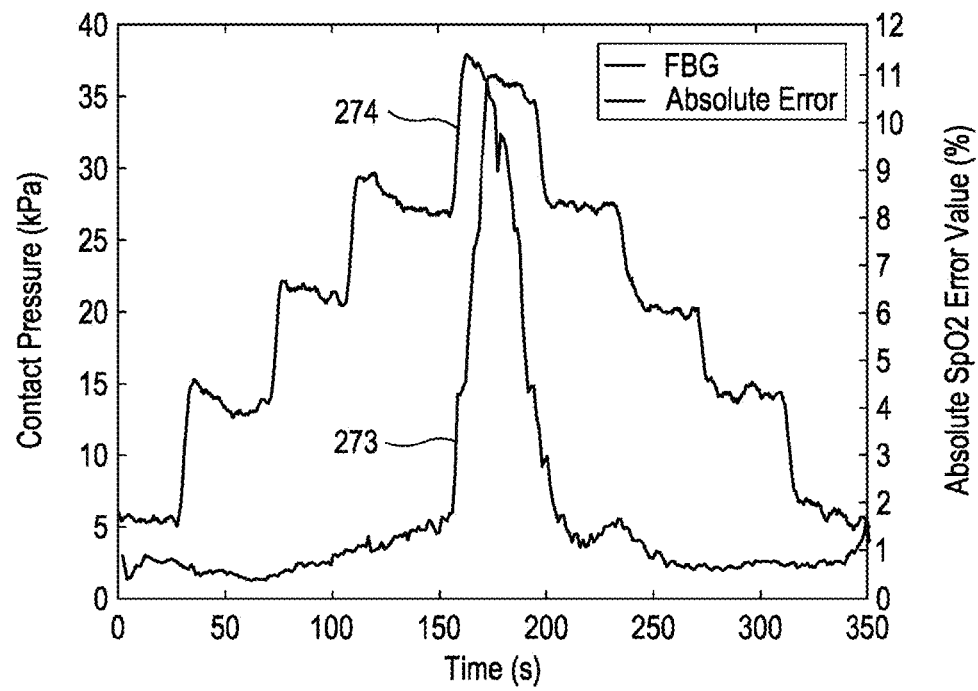

FIG. 17B shows the absolute $S_pO_2$ error between measurements obtained by the pulse oximeter patch 201 of the probe 200 and the commercial device (curve 273), and the contact pressure (curve 274). The initial pressure generated by weight of the index finger was between 4 to 6 kPa. For pressures higher than 15 kPa, the reliability and accuracy of the $S_pO_2$ determination by the pulse oximeter patch 201 are degraded relative to the commercial device.

Figure 17C:
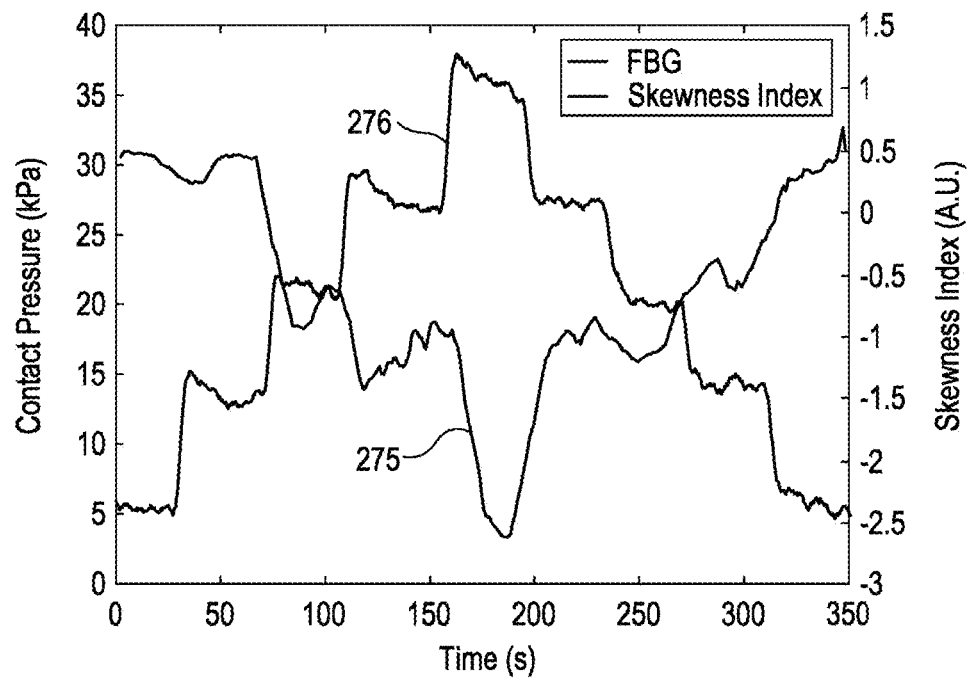
Figure 17D:
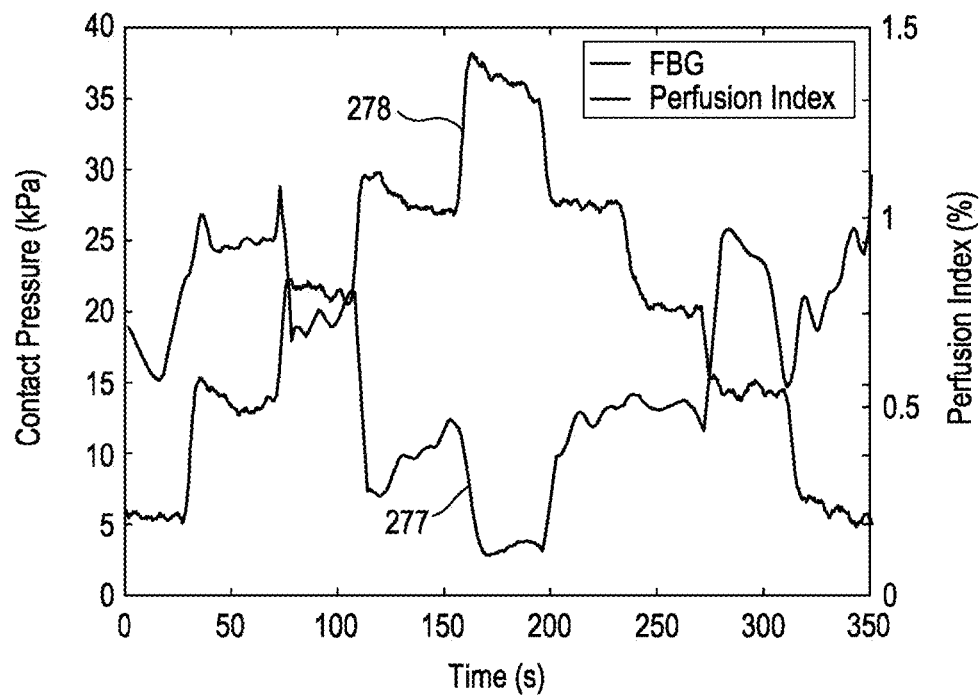

FIGS. 17C and 17D reinforce the observation that reliability and accuracy of the pulse oximeter patch 201 measurements are degraded under increasing pressure by illustrating the SI (curve 275) and SI (curve 277) of the infrared PPH signals falling. When the contact pressure (curves 276, 278) was increased higher than 15 kPa, both PI and SI sharply decreased but both recovered when the applied pressure returned below 15 kPa.

Figure 18:
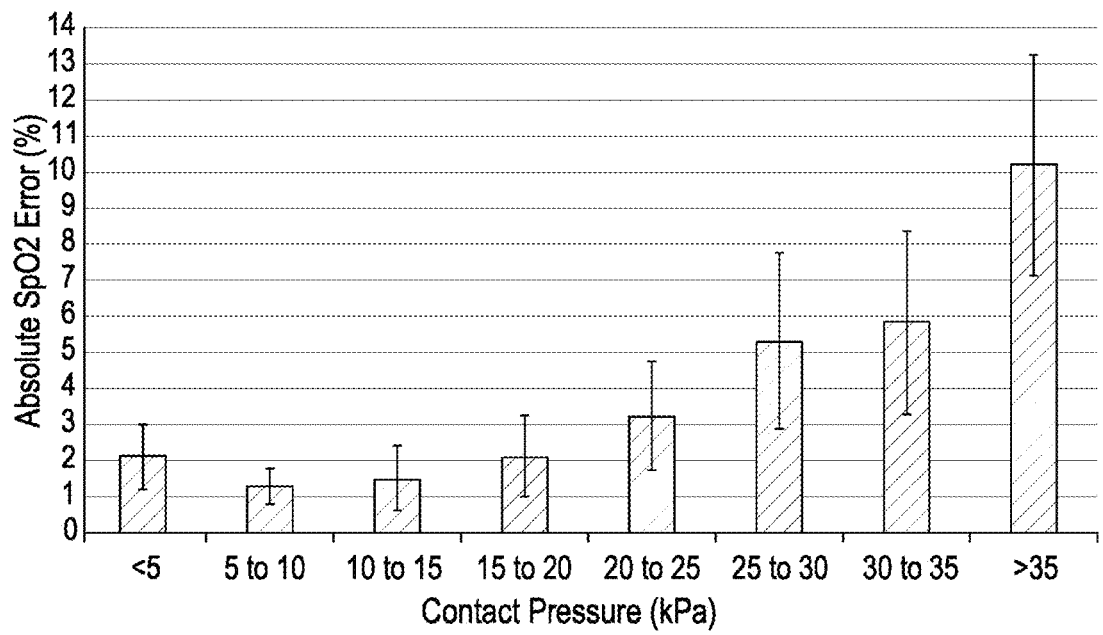
FIG. 18 shows a bar chart averaging data similar to that shown in FIGS. 17A to 17D collected for ten volunteers.

For each of the ten volunteers, the experimental processes described above were repeated three times to provide 30 data sets similar to those shown in FIGS. 17A to 17D. By averaging three measurements from each of the ten volunteers, a bar chart was established (shown in FIG. 18) which shows the effect of contact pressure on $S_pO_2$ detection. When the contact pressure is higher than 25 kPa, the $S_pO_2$ error between the pulse oximeter patch 201 and the commercial device is very high. When the contact pressure is lower than 15 kPa, the $S_pO_2$ error is less than 2%. The $S_pO_2$ error reached a minimum value while the contact pressure was between 5 kPa and 15 kPa. It is clear that the pressure range from 5 kPa to 15 kPa is optimal for $S_pO_2$ monitoring.

Figure 17E:
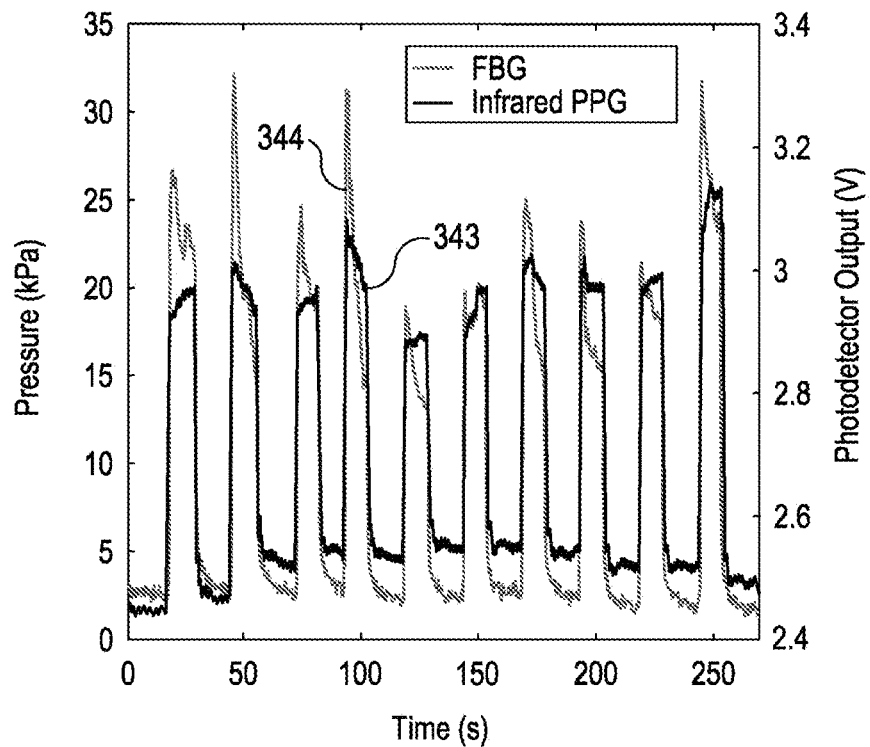
Figure 17F:
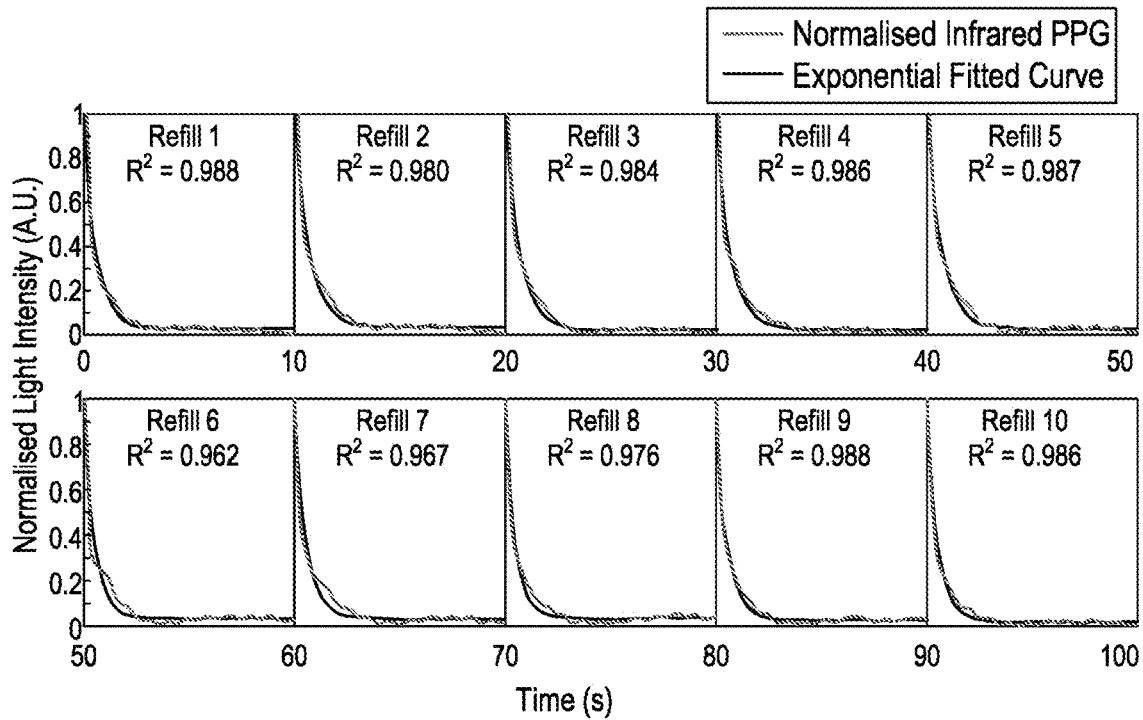
Figure 17G:
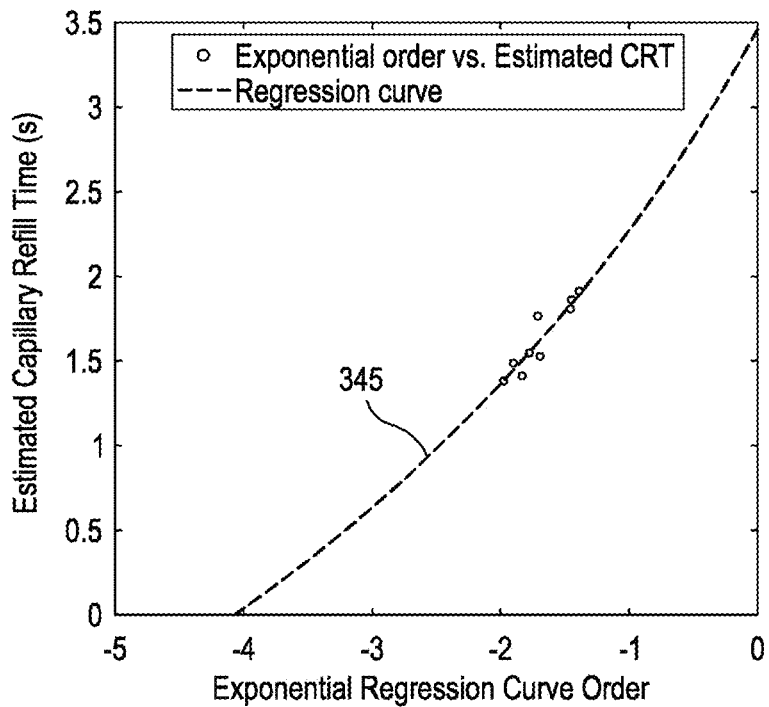

FIGS. 17E to 17G show results for a typical volunteer from a further test of ten volunteers using the setup of FIG. 14. FIG. 17E shows the reflected infrared PPG signals (curve 343) and the contact pressure (curve 344). FIG. 17F shows ten normalised capillary refills which were isolated from the reflected infrared light signal in FIG. 17E using the contact pressure record. Exponential regression curves were applied to the isolated and normalised refills. R square values of all exponential regression models are higher than 0.96. FIG. 17G shows the relationship between the estimated CRT (with a threshold level of 10%) versus the order of exponential model fit. The least squares regression line in FIG. 17G (curve 345) demonstrates that there is an exponential relationship between the order of exponential models and the estimated CRT.

Figure 17H:
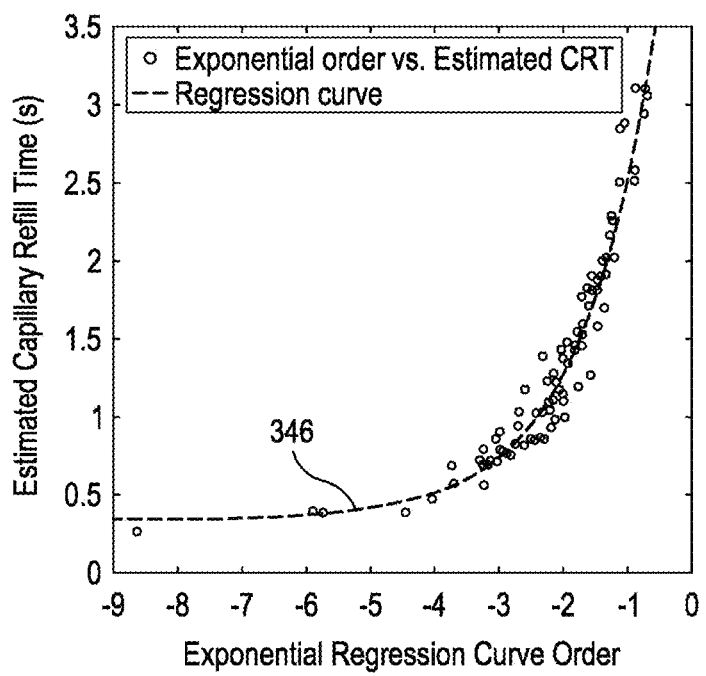

For each of ten volunteers the blanching process was repeated 10 times to provide 100 capillary refill datasets, all of which were similar to FIGS. 17E to 17G. FIG. 17H shows the diagram of estimated CRT (with a threshold level of 10%) versus the orders of exponential fitting curves for all 10 volunteers, which indicates an exponential relationship between the regression exponential order and estimated CRT:

$$y=5.163*e^{0.8508*x}+0.3478$$

The regression curve of FIG. 17H (curve 346) is a fit through the data which indicates an exponential relationship between regression orders and estimated CRT.

Figure 19A:
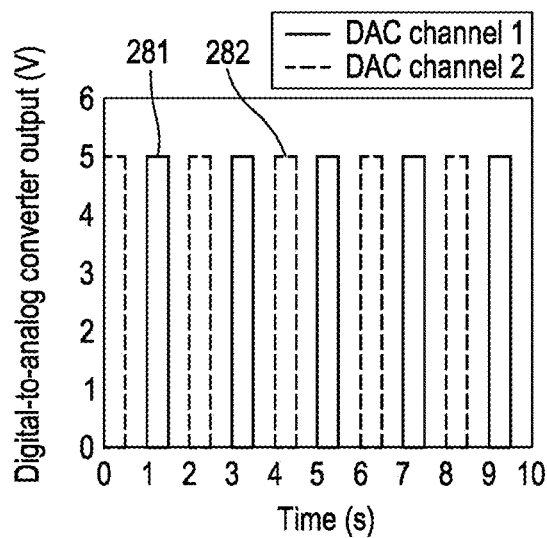
FIGS. 19A and 19B respectively show outputs of two DAC channels of a DAQ system, and outputs of two LEDS detected by a photo detector driven by the DAQ system.
Figure 19B:
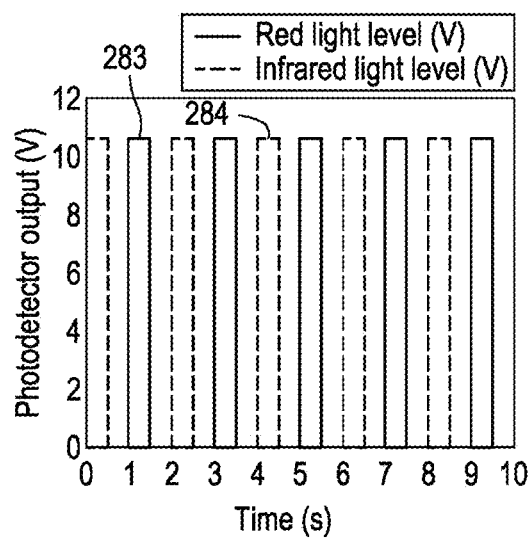
Figure 20:
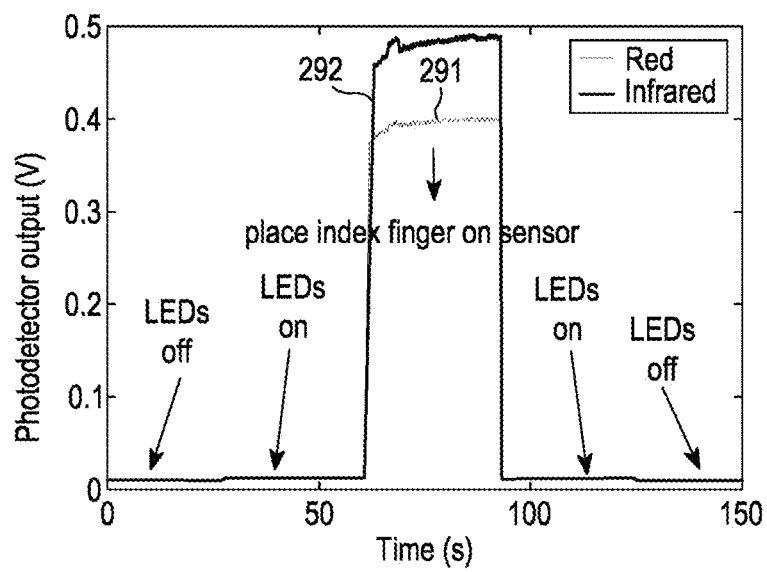
FIG. 20 shows immunity of the patch sensor of FIGS. 11A and 11B to stray light.
Figure 21:
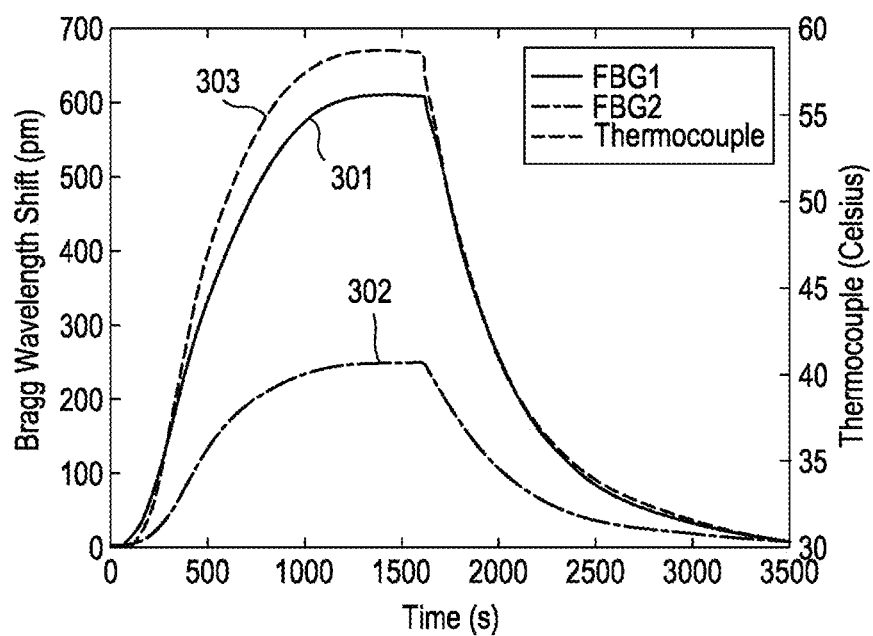
FIG. 21 shows temperature response of a FBG and a temperature compensation FBG of the patch sensor of FIGS. 11A and 11B and also of a thermocouple sensor.

Preliminary data showing the effectiveness and operational functionality of the system in i) correctly multiplexing the red and infrared channels, ii) reducing the effects of stray light and iii) the effect of temperature on the FBGs and the effectiveness of the temperature reference calibration is shown in FIGS. 19 to 21.

FIG. 19A shows outputs of two DAC channels of the DAQ system. The two square wave signals 281, 282 switch the red and infrared LEDs respectively on and off. FIG. 19B shows the output of the two LEDs as detected by the photodetector in curves 283 (red LED) and 284 (infrared LED). From FIG. 19B, it is clear that the two LED outputs do not overlap. Accordingly, the system is capable of using one photodetector to detect dual PPG signals.

FIG. 20 shows the immunity of the pulse oximeter patch 201 to stray light. Using the configuration shown in FIGS. 11 and 12, both LEDs were initially switched off and only ambient light from the room was present. After 30 s, both LEDs were switched on resulting in a 0.006 mV increase in light intensity level caused by light directly passing from the transmit POFs to the receive POF. Placing an index finger on the pulse oximeter patch results in a significant increase in detected light, as shown by the photodetector output signals in FIG. 20 for both red light (curve 291) and infrared light (curve 292). The black material placed between the transmit and receive POFs of the pulse oximeter patch 201 substantially absorbs the light interference caused by switching processes of the LEDs. In consideration of the relative photodetector output caused by the PPG signal in comparison to the photodetector output caused by light interference caused by switching processes of the LEDs, the light interference effect can be ignored.

FIG. 21 shows the temperature response of the FBG1 and the FBG2 of the pressure sensor patch 202. Curves 301 and 302 show the temperature performance of FBG1 and FBG2 respectively between 30° C. and 60° C., whilst curve 303 shows the output of the thermocouple. The peak wavelength shift curves of both the FBG1 and the FBG2 follow the same trend. Therefore, the Bragg wavelength shift of the FBG2 can directly subtracted from the Bragg wavelength shift of the FBG1 to compensate for temperature. The following empirical equation describes a simple temperature compensation calculation.

$$\lambda_{\Delta P\text{-}FBG1}=\lambda_{\Delta FBG1}-2.7577\times\lambda_{\Delta FBG2}+0.0147$$

$\lambda_{\Delta P\text{-}FBG1}$ is the Bragg wavelength shift in the FBG1 sensor with temperature compensation. $\lambda_{\Delta FBG1}$ and $\lambda_{\Delta FBG2}$ are Bragg wavelength shifts read from the FBG interrogator.

Capillary refill time may be measured by measuring an intensity of reflected light from a portion of skin the is illuminated. The illumination may be via an optical fibre, and the detection of the reflected light may be via an optical fibre (for example using an arrangement like that described above). When blood is pushed from the capillaries due to pressure, the colour of the pressed skin becomes pale, and more light will be reflected therefrom. As the skin returns to its normal colour after unloading, the intensity of the reflected light will return to a baseline. The time that it takes the skin to return to this baseline after loading may be measured as the capillary refill time. In addition to changes in the reflected light arising from pressure, there will a pulsatile component.

Figure 22:
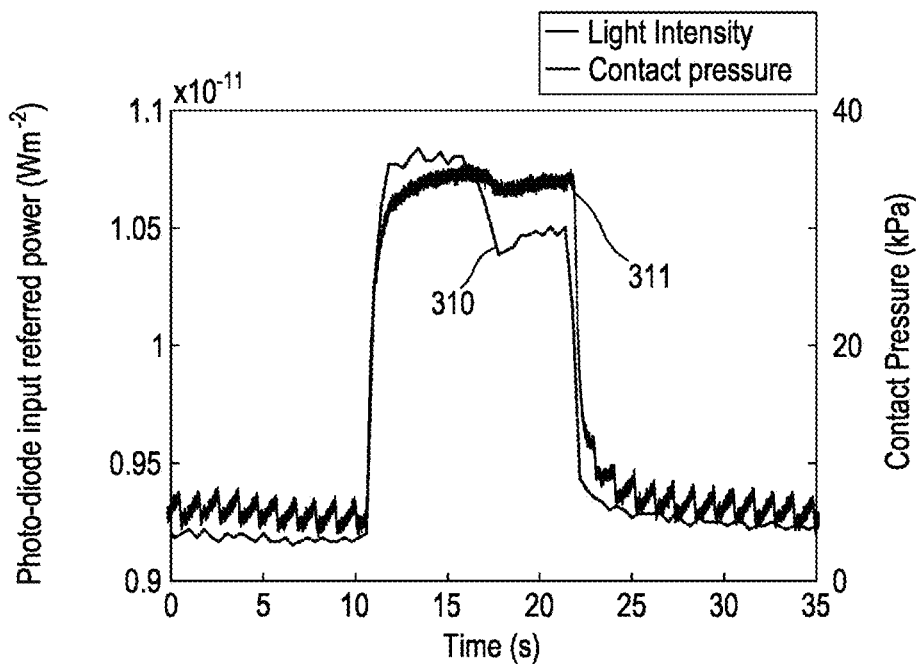
FIG. 22 shows example capillary refill measurement results using a sensor of the type shown in FIGS. 11A and 11B.

FIG. 22 shows example capillary refill measurement results using a sensor of the type shown in FIGS. 11A and 11B. The reflected light intensity 311 (measured via the receive POF) is plotted with the contact pressure 310 (measured using the FBG interrogator). The POF patch (the top layer of the designed sensor) is capable of detecting the reflected light intensity changes (e.g. at 660 nm and 850 nm), and can therefore monitor the changes in skin colour that arise from pressure. The FBG patch (the bottom layer of the example sensor) measures contact pressure. The pulsatile component of the intensity signal 311 disappears when the contact pressure is high enough to push the capillary blood out. The extinction of the pulsatile component of the reflected light intensity signal can thereby be used as an index for guiding pressure adjustment (with extinction of the pulsatile component corresponding with sufficient pressure to perform a CRT measurement). The applicants have found that one example of a pressure criteria for performing CRT measurements is to consider a refill interval on contact pressure reducing to 10 kPa or less, having previously been above 15 kPa for at least 5 seconds.

Figure 23:
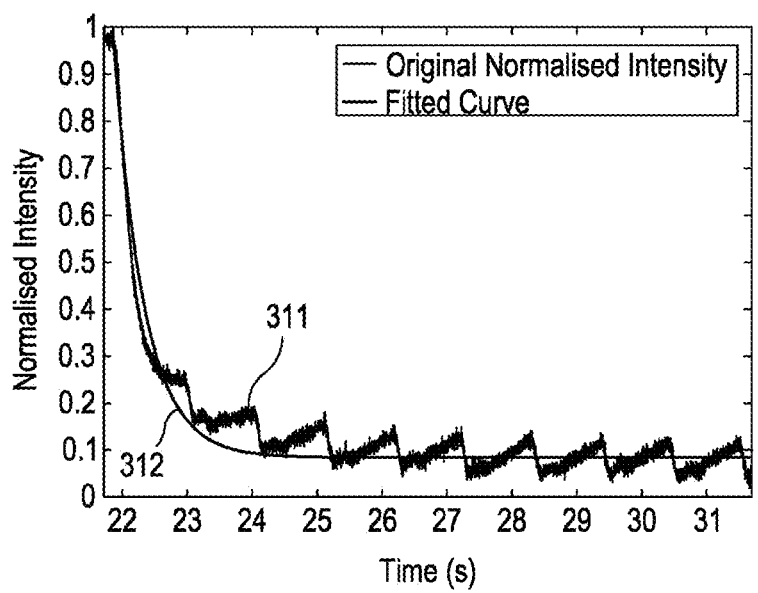
FIG. 23 shows an example of a refill interval, in which an exponential curve has been fitted to the reflected light intensity.

FIG. 23 shows an example of a refill interval, in which an exponential curve 312 has been fitted to the reflected light intensity 311. Such an exponential fit can be used to infer the capillary refill time in a way that is insensitive to the pulsatile component. The exponential may be of the form:

$$I_{FN} = e^{a \times x} + B_0$$

Where $I_{FN}$ is the fitted normalised intensity data, a is the exponential order and $B_0$ is the baseline of the intensity data (e.g. obtained from the unloaded average reflected light intensity, or obtained from a linear fit to the unloaded reflected light intensity).

A plurality of CRT measurements can be obtained from fitting exponential curves to refill intervals (that may be automatically identified based on the contact pressure). At least some of these fitted curves (or their parameters) may be combined in order to arrive at a CRT measurement. At least some of the fitted curves may be rejected as unlikely to be accurate based on criteria such as:
1. Refill had an excessive root mean squared fit error (RMSE). Excessive RMSE indicating that the shape of the reflected light intensity signal was not a good match with the exponential fitting curve.
2. Refill had a positive gradient for the blood refilling part. During the period of the blood refilling back, the reflected light intensity should be continuously dropping.
3. Refill had an excessive gradient for the baseline part. For the normal situation, the baseline of intensity data should be almost constant. Therefore, an excessive gradient indicates that deformation is present in the baseline region.

The CRT may be obtained from the average (e.g. median or mean) of the fitted curves that are not rejected.

Figure 24:
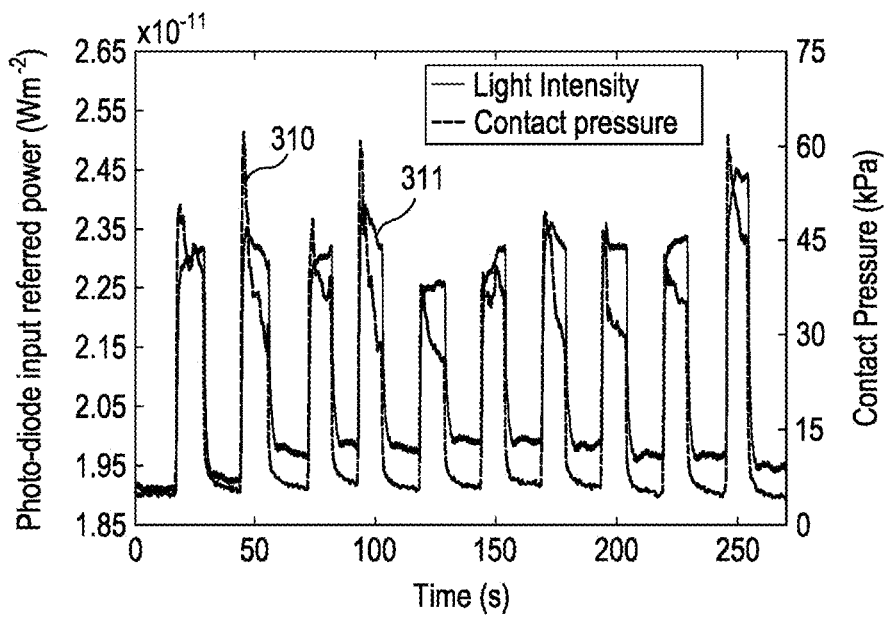
FIG. 24 shows the reflected light intensity and corresponding contact pressures for 10 capillary refills for one volunteer.
Figure 25:
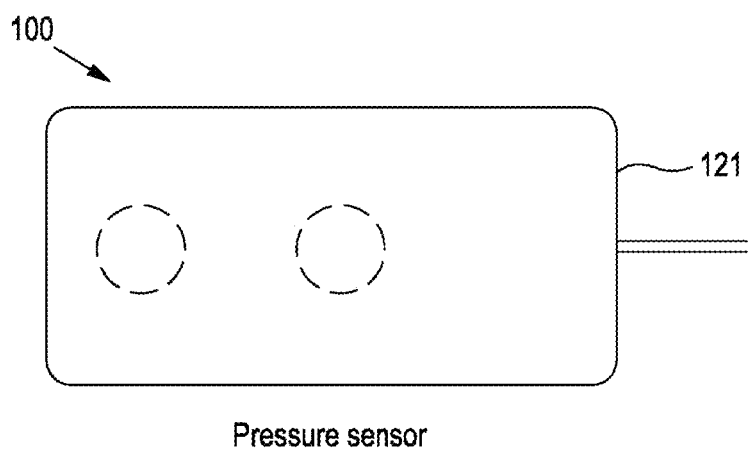
FIGS. 25, 26 and 27 show a system comprising an optical fibre assembly and an optical fibre pressure sensor according to an embodiment.
Figure 26:
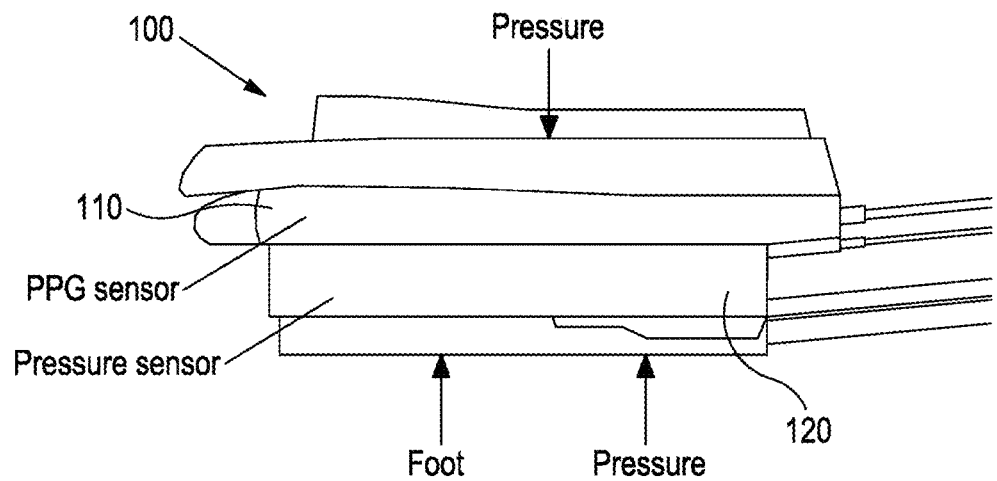

FIG. 24 shows the reflected light intensity 311 and corresponding contact pressures 310 for 10 capillary refills for one volunteer. The test results were obtained by the volunteer putting their index finger on top of the patch, and then pressing until extinction of pulsatile signals, maintaining this pressure for around 10 seconds, and then reducing the pressure to less than 10 kPa for around 10 seconds. The CRT of the volunteer can be inferred from fits made to these curves.

Figure 27:
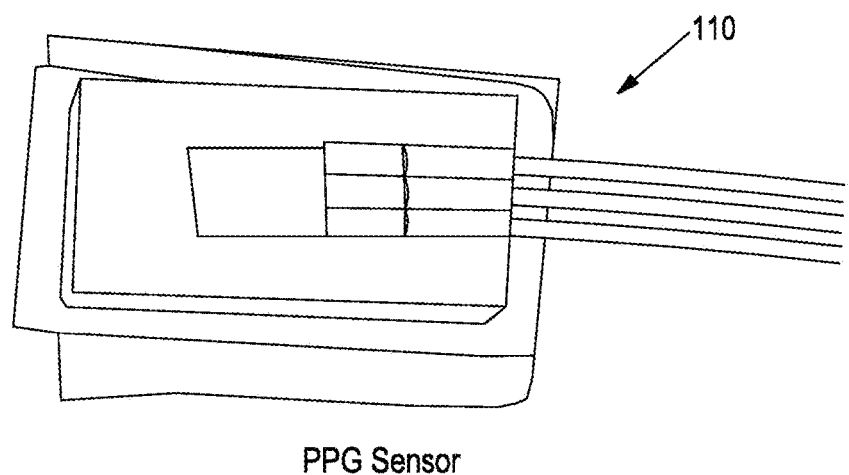
Figure 28:
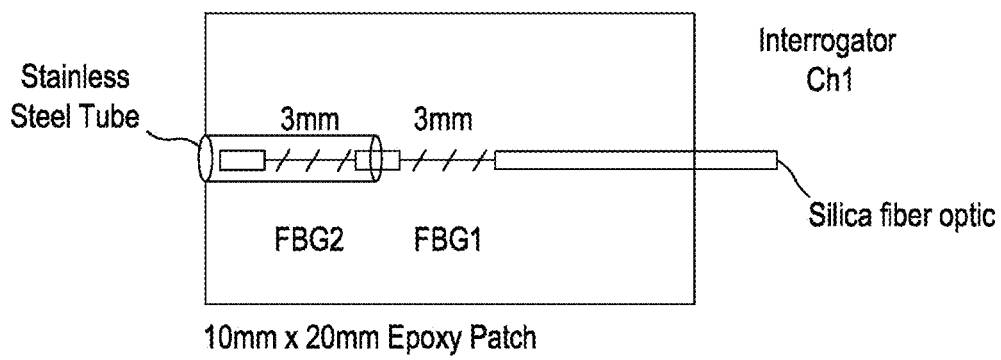
FIG. 28 shows a schematic of a sensor of the system of FIGS. 25, 26 and 27.

FIGS. 25 to 28 show a system 100 according to an embodiment of the invention. The system 100 comprises a patch 121 within which is embedded an optical fibre assembly 110 in the form of a PPG sensor 110. The system 100 further comprises a pressure sensor 120 in the form of an FBG sensor 120. FIG. 27 shows a detailed view of the PPG sensor 110. FIG. 28 shows a schematic of the PPG sensor 110. The dimensions of the patch 121 may be 10 mm×20 mm×2 mm and the dimensions of the PPG sensor 110 may be 10 mm×20 mm×2 mm. As shown in FIG. 28, the FBG sensor 120 comprises a silica fiber optic, a first FBG1, a second FBG2 and a stainless steel tube shielding the second FBG2. Each of the first FBG1 and the second FBG2 may be 3 mm long.

Figure 29:
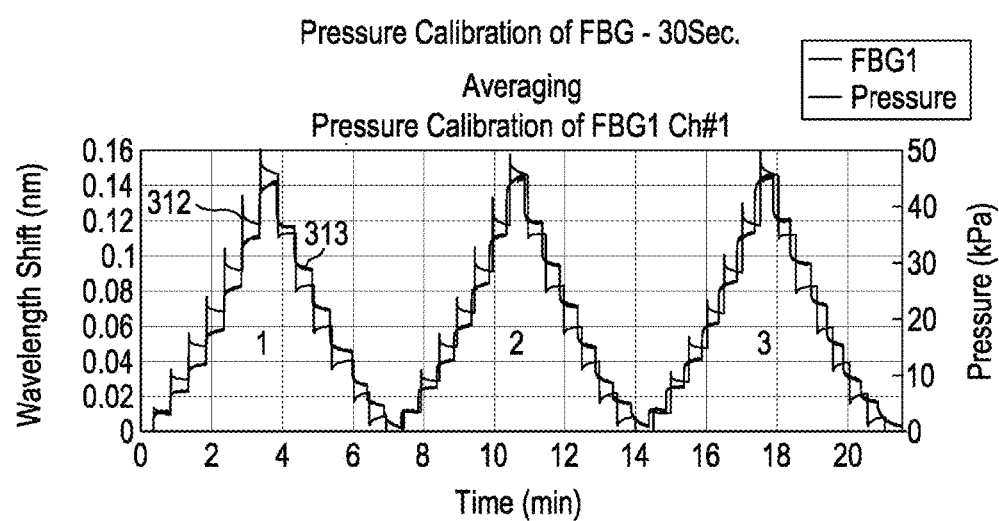
FIG. 29 shows the results of a pressure calibration of a sensor of the system of FIGS. 25, 26 and 27.

FIG. 29 shows the results of a pressure calibration of the first FBG1 of the FBG sensor 120 of FIGS. 25 to 28. The graph of FIG. 29 shows three repetitions of pressure calibration (labelled '1', '2' and '3' respectively). For each repetition, pressure was applied to the FBG sensor 120 in increments of 7 kPa from 0 kPa to approximately 50 kPa, before pressure was removed in increments of 7 kPa back to 0 kPa. The curve 312 shows the average variation of pressure over time during the calibration, and the curve 313 shows the average variation of Bragg wavelength shift over time during the calibration. Measurements recorded during the first 3 second of each pressure loading increment were not included in the averaging. The sensitivity of the average measurements was 3.1 pm/kPa.

Figure 30:
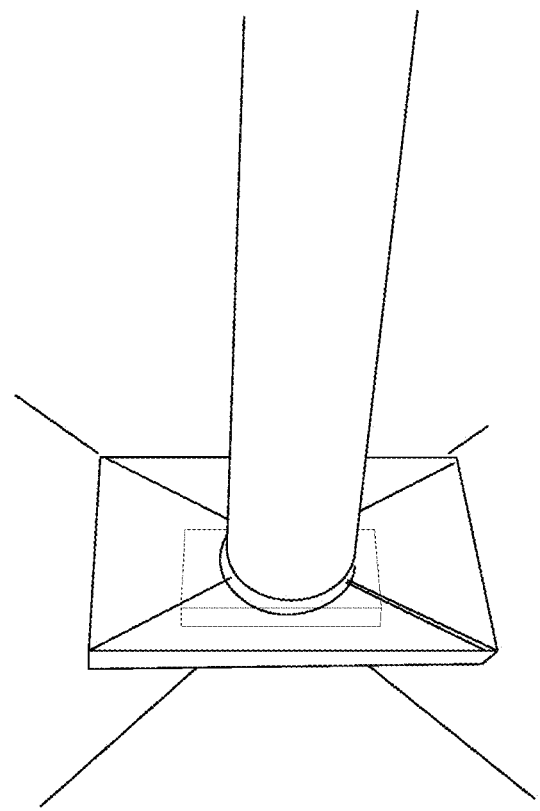
FIG. 30 shows the equipment used in the pressure calibration of FIG. 29.

FIG. 30 shows the equipment used to carry out the pressure calibration of FIG. 29.

Figure 31:
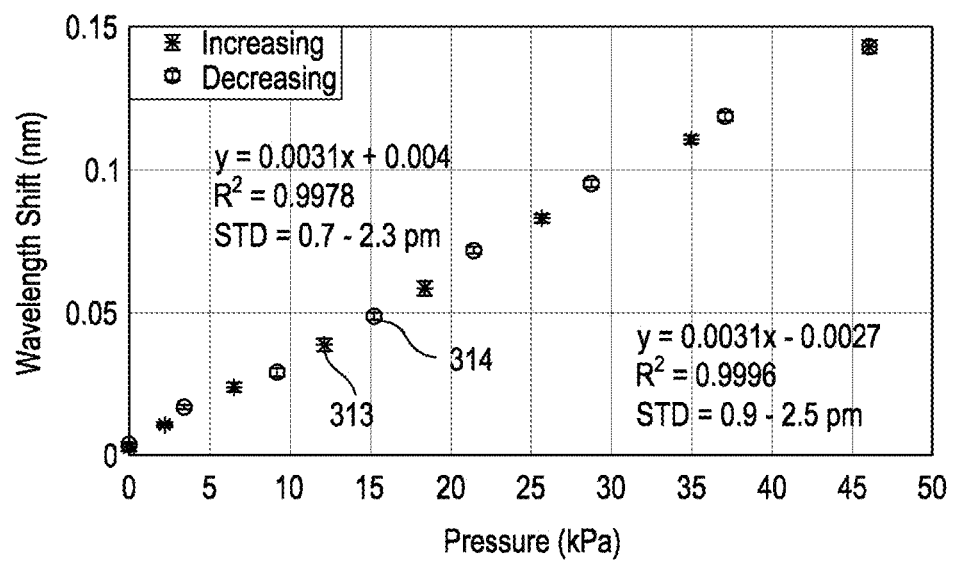
FIG. 31 shows a plot of the average variation of Bragg wavelength shift with pressure during the pressure calibration of FIG. 29.

FIG. 31 shows a plot of the average variation of Bragg wavelength shift with pressure during the pressure calibration of FIG. 29. A first set of points 313 show ? and a second set of points 314 show that there is no hysteresis. The $R^2$ value for the first set of points 313 is 0.9996 and the $R^2$ value for the second set of points 314 is 0.9978. The standard deviation of the first set of points 313 is 0.7-2.3 pm and the standard deviation of the second set of points 314 is 0.9-2.5 pm.

Figure 32:
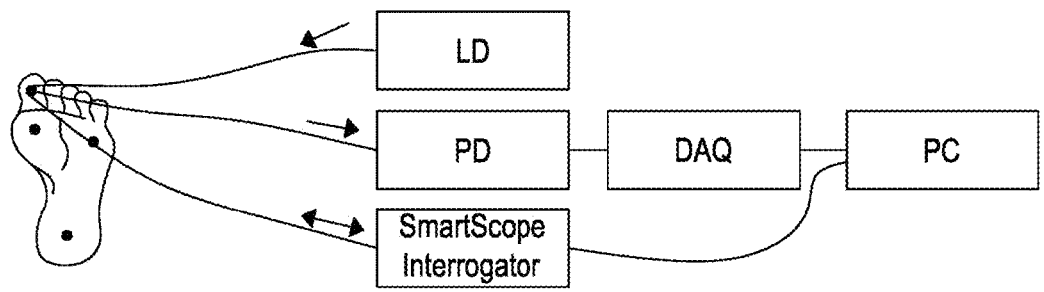
FIG. 32 shows an arrangement in which the system of FIGS. 25, 26 and 27 is in contact with a toe of an individual and is secured in place with a bandage.
Figure 33:
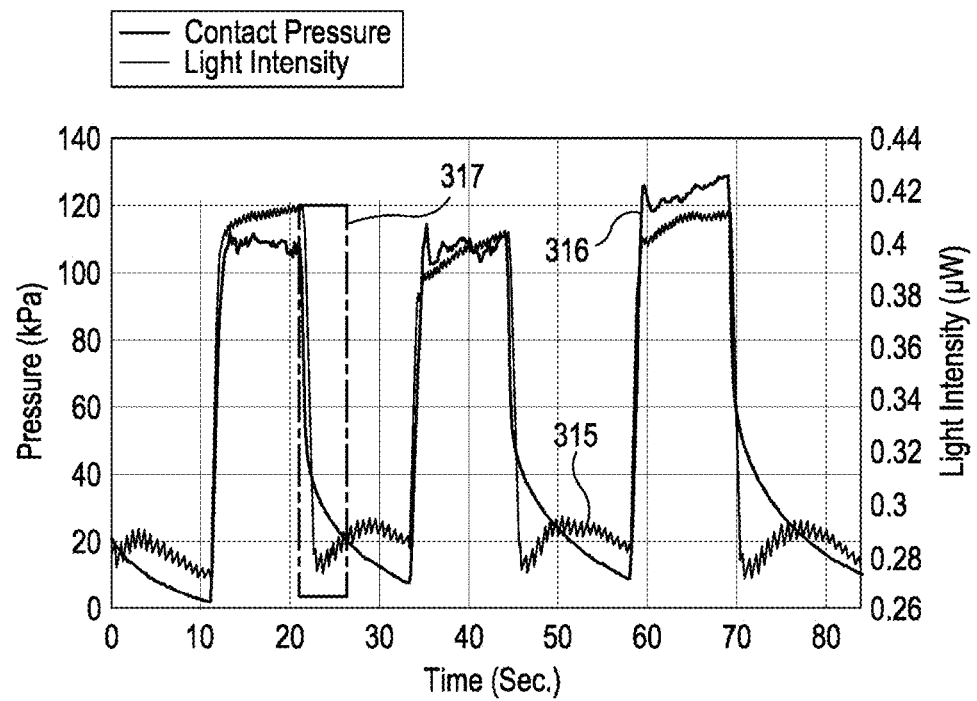
FIG. 33 shows the results of a test during which pressure was applied and released to the system of FIGS. 25, 26 and 27, in the arrangement of FIG. 32, in three cycles.
Figure 34:
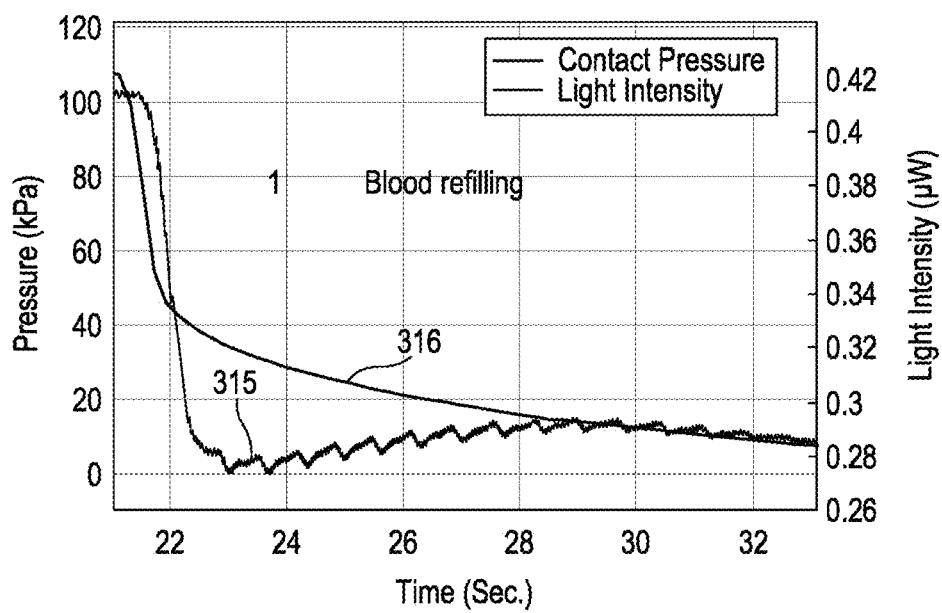
FIG. 34 shows a higher resolution plot of light intensity and pressure measured during a period of capillary refill of the test of FIG. 33.

FIG. 32 shows an arrangement in which the system 100 of FIGS. 25 to 28 is in contact with a toe of an individual and is secured in place with a bandage. FIG. 33 shows the results of a test during which pressure was applied and released to the system 100 in three cycles. Pressure was applied to the system 100 by an individual using their thumb. Each of the three cycles comprised a period of approximately ten seconds of approximately constant pressure being applied to the system 100, followed by a period of approximately ten seconds during which the pressure was released. FIG. 33 shows light intensity measured at the PPG sensor 110 and pressure measured at the FBG sensor 120 during the three cycles. Green light was utilised by the PPG sensor 110 during the test. Light intensity is shown by curve 315 and pressure is shown by curve 316. A period of capillary refill followed each ten second period of applied pressure. One such period 317 is indicated in FIG. 33. A higher resolution plot of the light intensity and pressure measurements during this period of capillary refill 317 is shown in FIG. 34.

Figure 35:
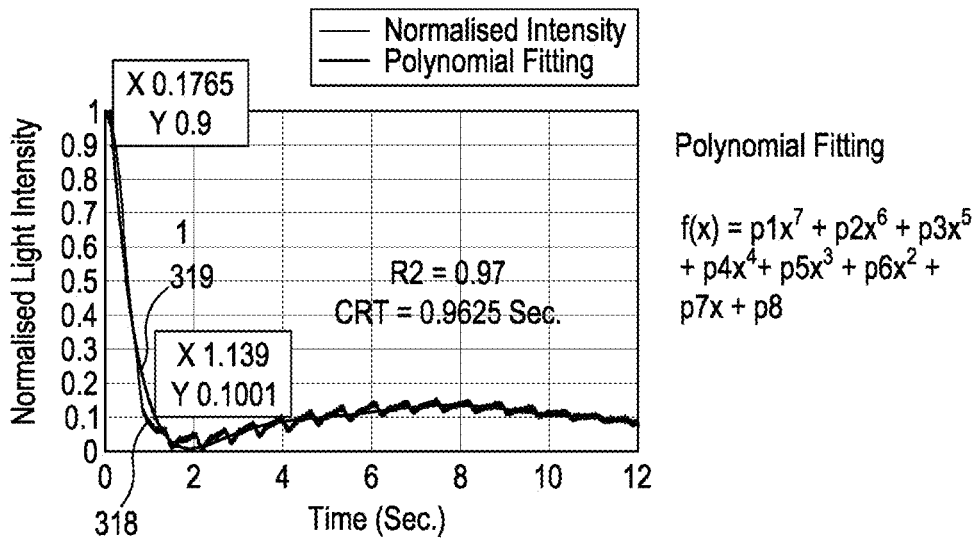
FIG. 35 shows a polynomial fitting applied to normalised results of light intensity as measured during a period of capillary refill of the test of FIG. 33.
Figure 36:
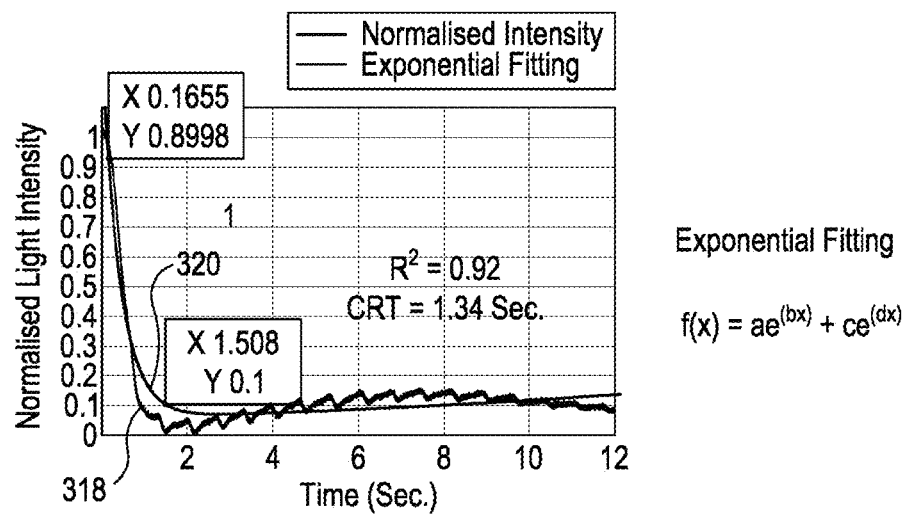
FIG. 36 shows an exponential fitting applied to normalised results of light intensity as measured during a period of capillary refill of the test of FIG. 33.

FIGS. 35 and 36 show normalised light intensity (curve 318) measured during a period of capillary refill. In FIG. 35 a polynomial fitting (curve 319) has been applied to the normalised light intensity results to give a polynomial fitting of:

$$f(x) = p1x^7 + p2x^6 + p3x^5 + p4x^4 + p5x^3 + p6x^2 + p7x + p8$$

In FIG. 36, an exponential fitting (curve 320) has been applied to the normalised light intensity results to give an exponential fitting of:

$$f(x) = ae^{(bx)} + ce^{(dx)}$$

The $R^2$ value of normalised light intensity obtained from the polynomial fitting of FIG. 35 was 0.97, and the $R^2$ value of normalised light intensity obtained from the exponential fitting of FIG. 36 was 0.92. A CRT value for normalised light intensity was obtained using each of the polynomial fitting and the exponential fitting. The CRT value was obtained from the difference between the time elapsed when the respective fitting indicated a normalised light intensity of 0.1 and the time elapsed when the respective fitting indicated a normalised light intensity of 0.9. Using this method, the polynomial fitting gave a CRT value of 0.9625 s and the exponential fitting gave a CRT value of 1.34 s. The plots of FIGS. 35 and 36 show that normalised light intensity measured during a capillary refill period fits well with a polynomial curve.

Figure 37:
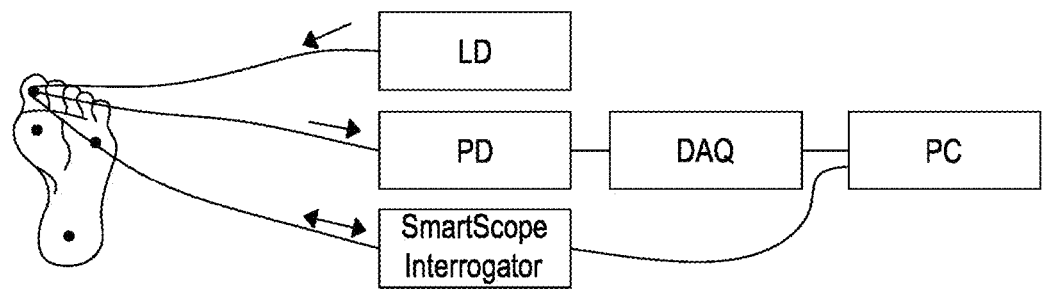
FIG. 37 shows an arrangement in which the system of FIGS. 25, 26 and 27 is in contact with the bottom of a foot of an individual and is secured in place with a bandage.
Figure 38:
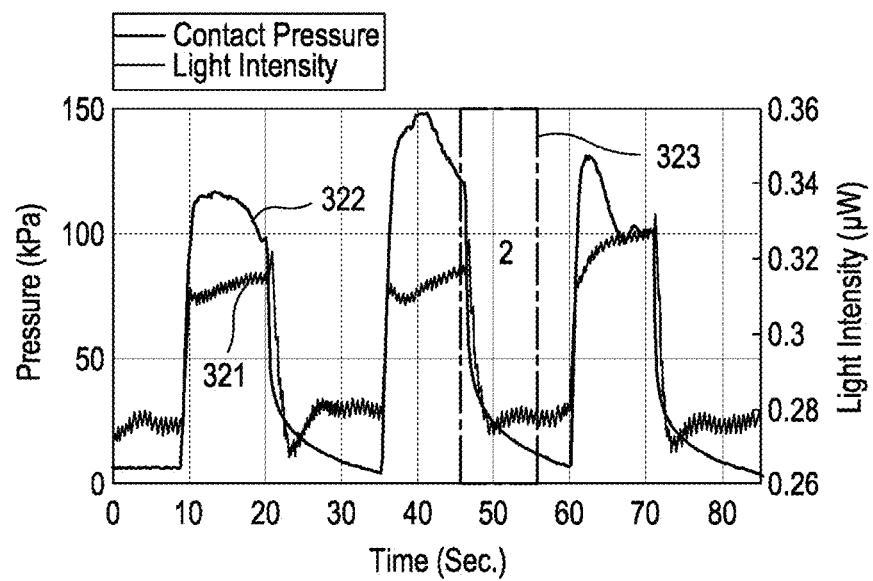
FIG. 38 shows the results of a test during which pressure was applied and released to the system of FIGS. 25, 26 and 27, in the arrangement of FIG. 37, in three cycles.
Figure 39:
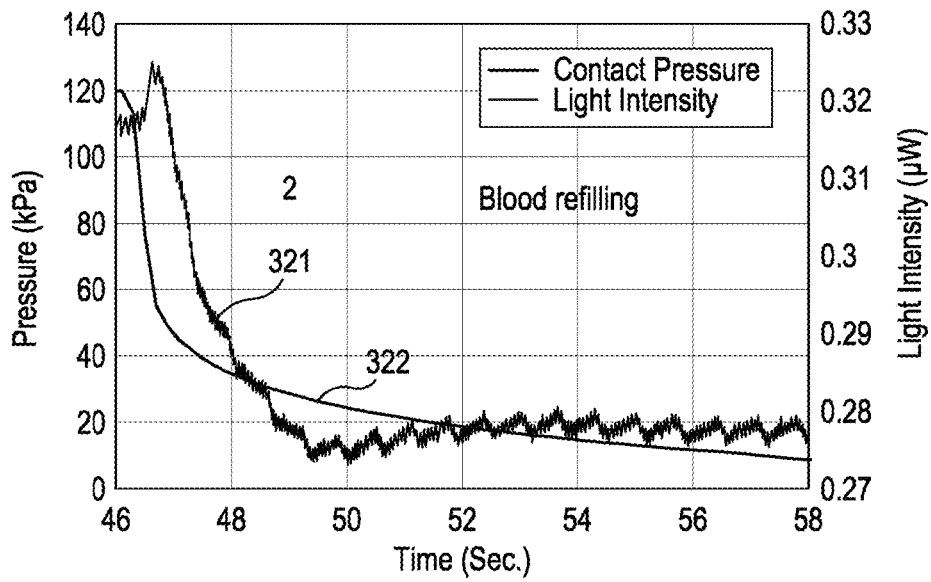
FIG. 39 shows a higher resolution plot of light intensity and pressure measured during a period of capillary refill of the test of FIG. 38.

FIG. 37 shows an arrangement in which the system 100 of FIGS. 25 to 28 is in contact with the bottom of a foot of an individual and is secured in place with a bandage. FIG. 38 shows the results of a test during which pressure was applied and released to the system 100 in three cycles. Pressure was applied to the system 100 by an individual using their thumb. Each of the three cycles comprised a period of approximately ten seconds of approximately constant pressure being applied to the system 100, followed by a period of approximately ten seconds during which the pressure was released. FIG. 38 shows light intensity measured at the PPG sensor 110 and pressure measured at the FBG sensor 120 during the application of pressure to the system 100 by an individual using their thumb. Green light was utilised by the PPG sensor 110 during the test. Light intensity is shown by curve 321 and pressure is shown by curve 322. A period of capillary refill followed each ten second period of applied pressure. One such period of capillary refill 323 is indicated in FIG. 38. A higher resolution plot of the light intensity and pressure measurements during this period of capillary refill 323 is shown in FIG. 39.

Figure 40:
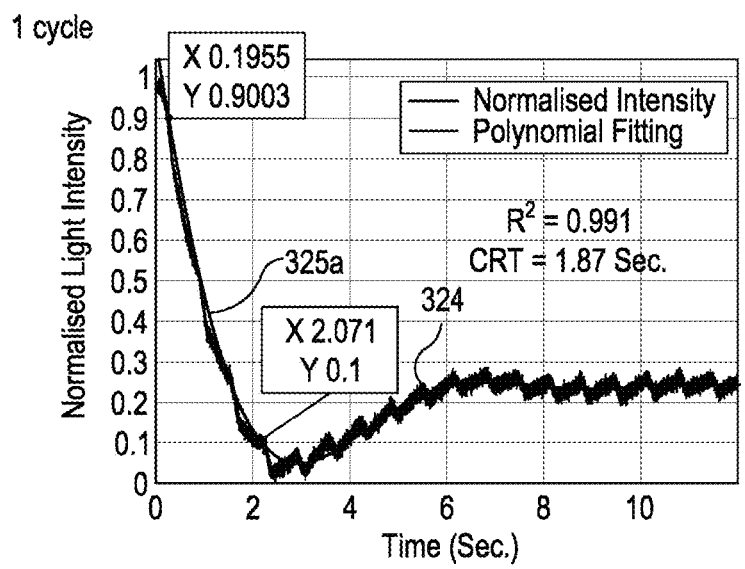
FIG. 40 shows a polynomial fitting applied to normalised results of light intensity as measured during a first period of capillary refill of the test of FIG. 38.
Figure 41:
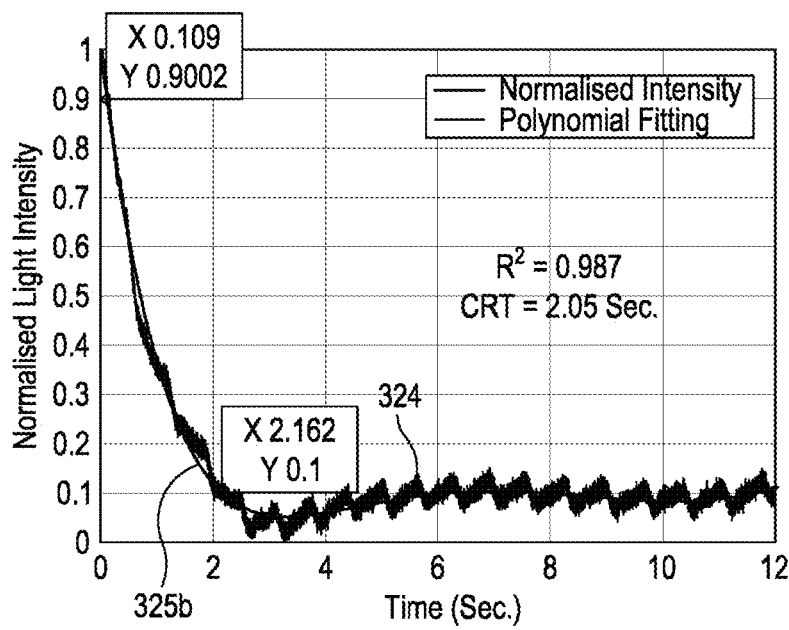
FIG. 41 shows a polynomial fitting applied to normalised results of light intensity as measured during a second period of capillary refill of the test of FIG. 38.
Figure 42:
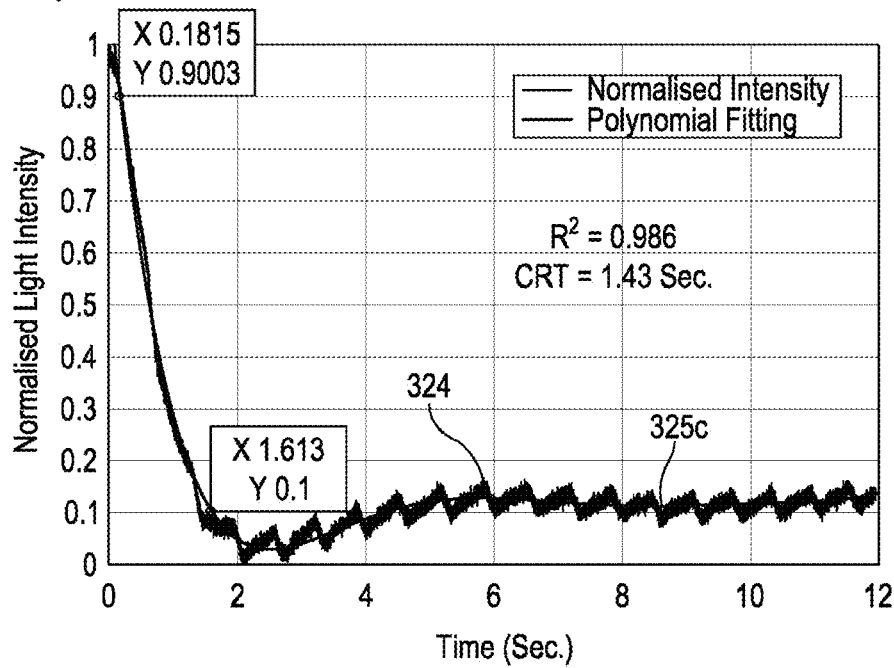
FIG. 42 shows a polynomial fitting applied to normalised results of light intensity as measured during a third period of capillary refill of the test of FIG. 38.

FIG. 40 shows normalised light intensity (curve 324) during the period of capillary refill following the first period of applied pressure of FIG. 38. FIGS. 41 and 42 show normalised light intensity during the periods of capillary refill following the second and third periods of applied pressure of FIG. 38 respectively. Polynomial fittings 325a, 325b and 325c were applied to the normalised light intensity data of FIGS. 40, 41 and 42 respectively. The $R^2$ values obtained from the polynomial fittings 325a, 325b and 325c were 0.991, 0.987 and 0.986 respectively. The CRT values obtained from the polynomial fittings 325a, 325b and 325c were 1.87 s, 2.05 s and 1.43 s respectively. This gives an average CRT value of 1.78 s and a standard deviation of the CRT values of 0.31 s.

Figure 43:
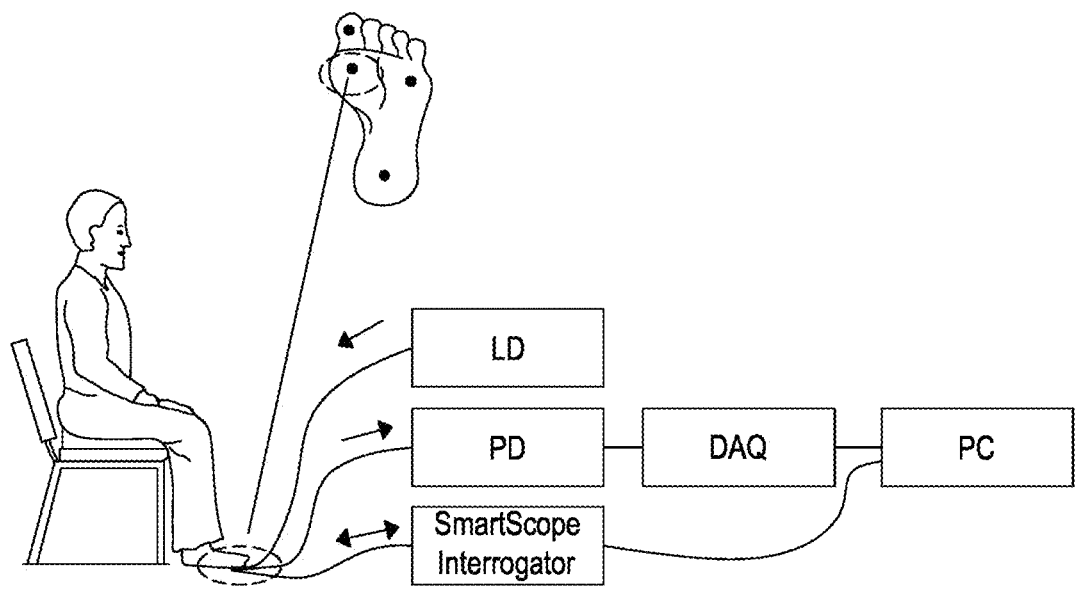
FIG. 43 shows an arrangement in which the system of FIGS. 25, 26 and 27 is fixed in position on a flat surface.
Figure 44:
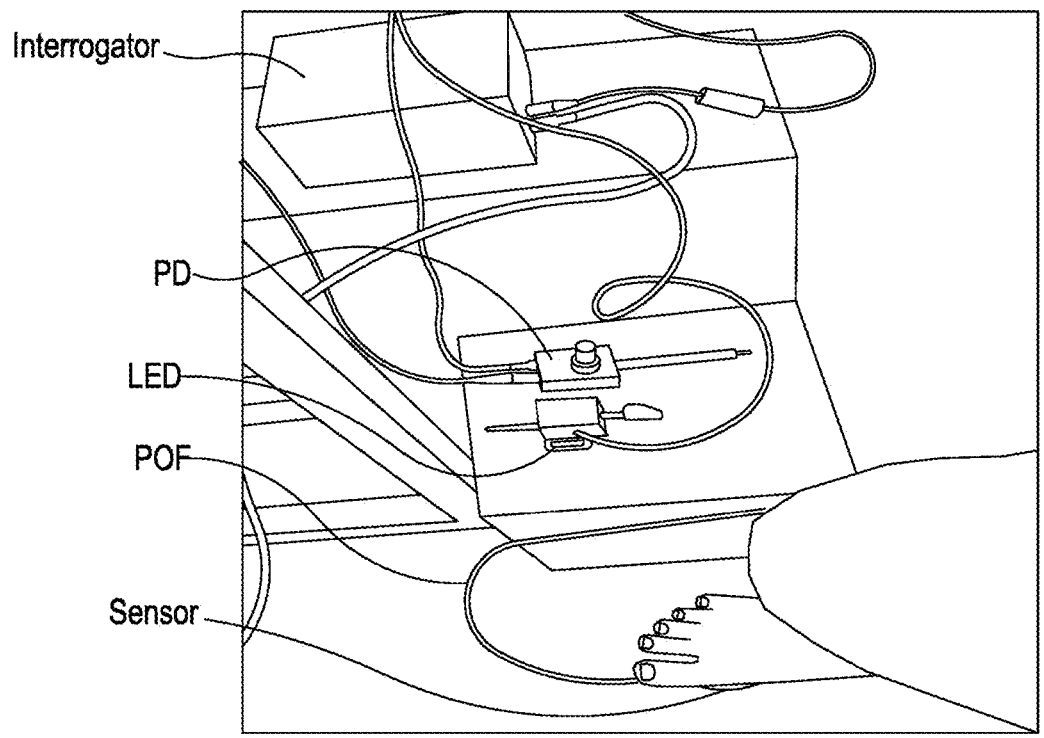
FIG. 44 shows a further view of the arrangement of FIG. 43.
Figure 45:
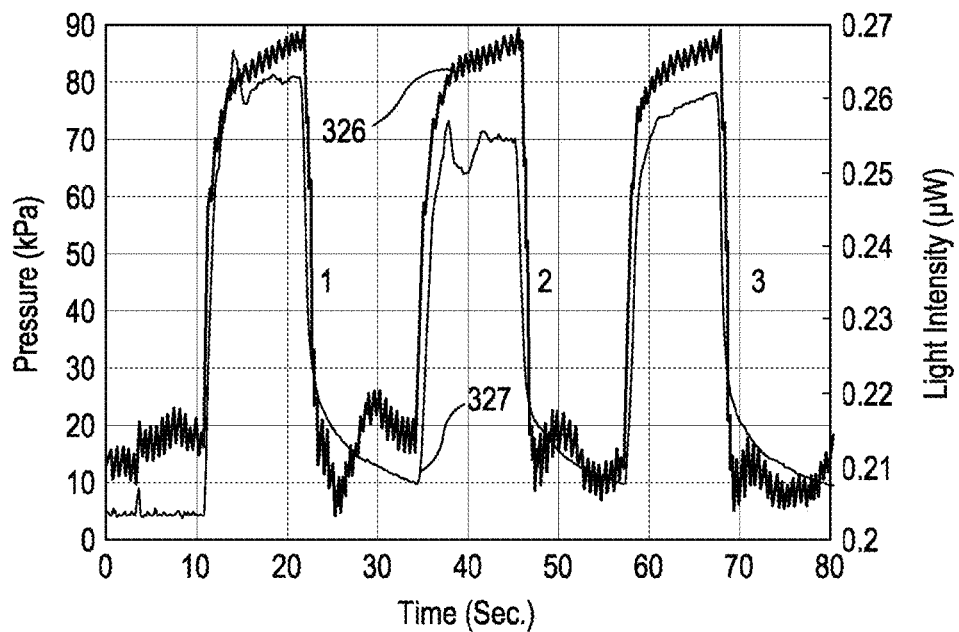
FIG. 45 shows the results of a test during which pressure was applied and released to the system of FIGS. 25, 26 and 27, in the arrangement of FIGS. 43 and 44, by an individual using their foot whilst in a seated position, in three cycles.
Figure 46:
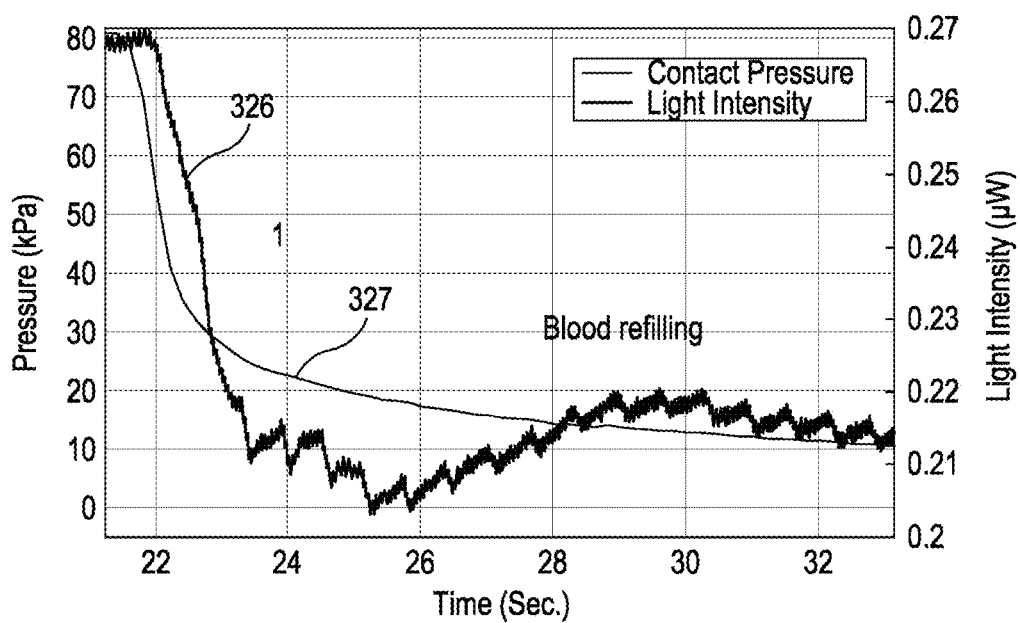
FIG. 46 shows a higher resolution plot of light intensity and pressure measured during a period of capillary refill of the test of FIG. 45.

FIG. 43 shows an arrangement in which the system 100 of FIGS. 25 to 28 is fixed in position on a flat surface. FIG. 44 shows a further view of the arrangement of FIG. 43. FIG. 45 shows the results of a test during which pressure was applied and released to the system 100 in three cycles. Pressure was applied to the system 100 by an individual using their foot whilst in a seated position. Each of the three cycles comprised a period of approximately ten seconds of approximately constant pressure being applied to the system 100, followed by a period of approximately ten seconds during which the pressure was released. FIG. 45 shows light intensity measured at the PPG sensor 110 and pressure measured at the FBG sensor 120 during the application of pressure to the system 100 by an individual using their thumb. Green light was utilised by the PPG sensor 110 during the test. Light intensity is shown by curve 326 and pressure is shown by curve 327. A period of capillary refill followed each ten second period of applied pressure. A higher resolution plot of the light intensity and pressure measurements during the period of capillary refill following the first period of applied pressure is shown in FIG. 46.

Figure 47:
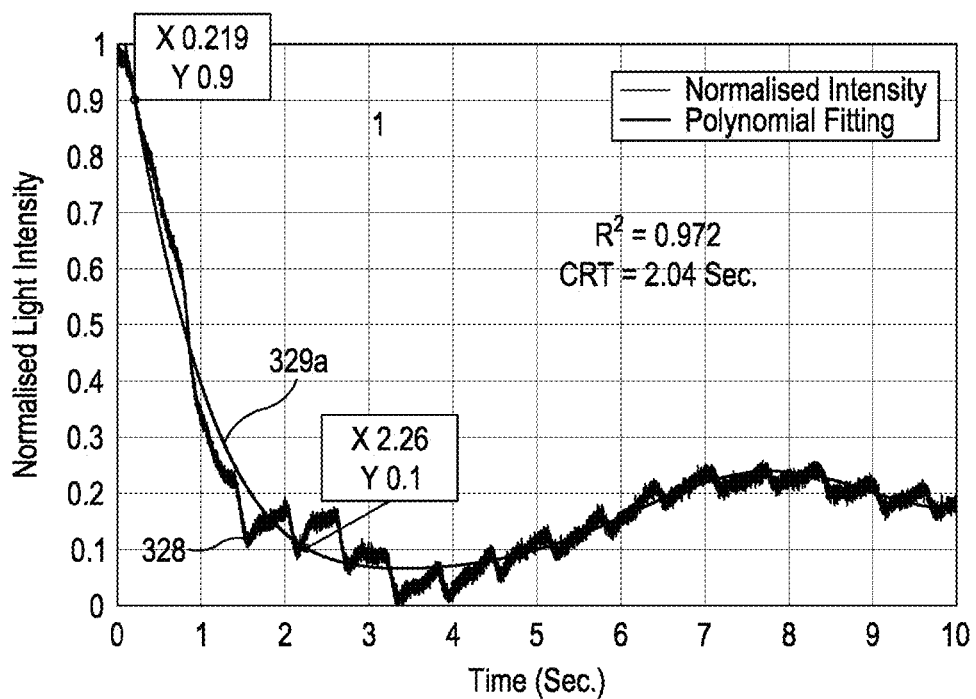
FIG. 47 shows a polynomial fitting applied to normalised results of light intensity as measured during a first period of capillary refill of the test of FIG. 45.
Figure 48:
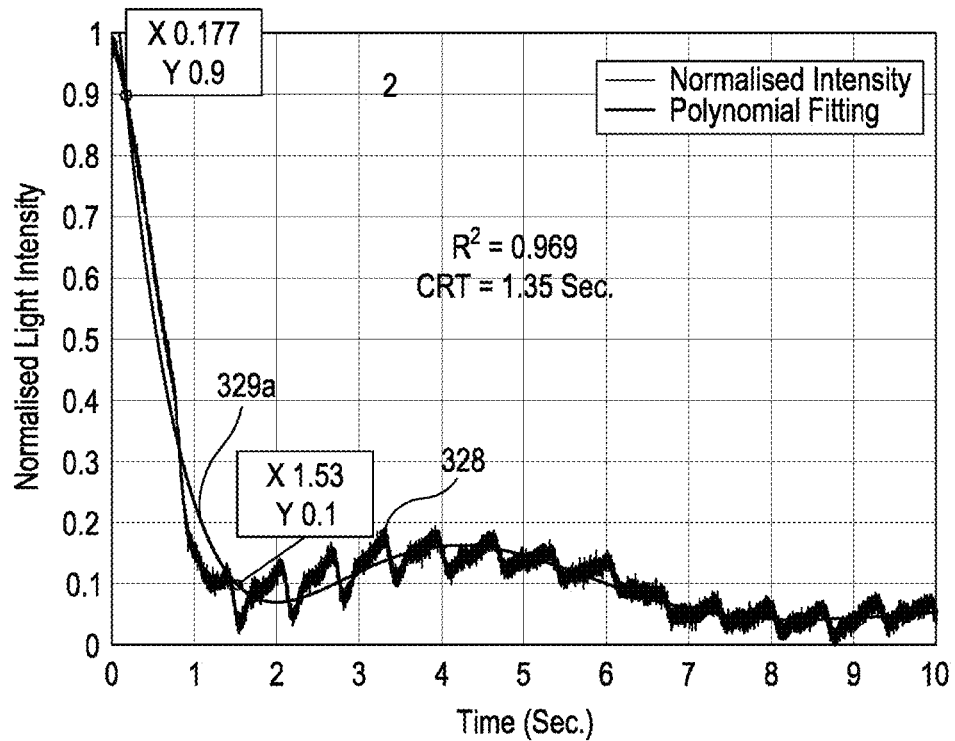
FIG. 48 shows a polynomial fitting applied to normalised results of light intensity as measured during a second period of capillary refill of the test of FIG. 45.
Figure 49:
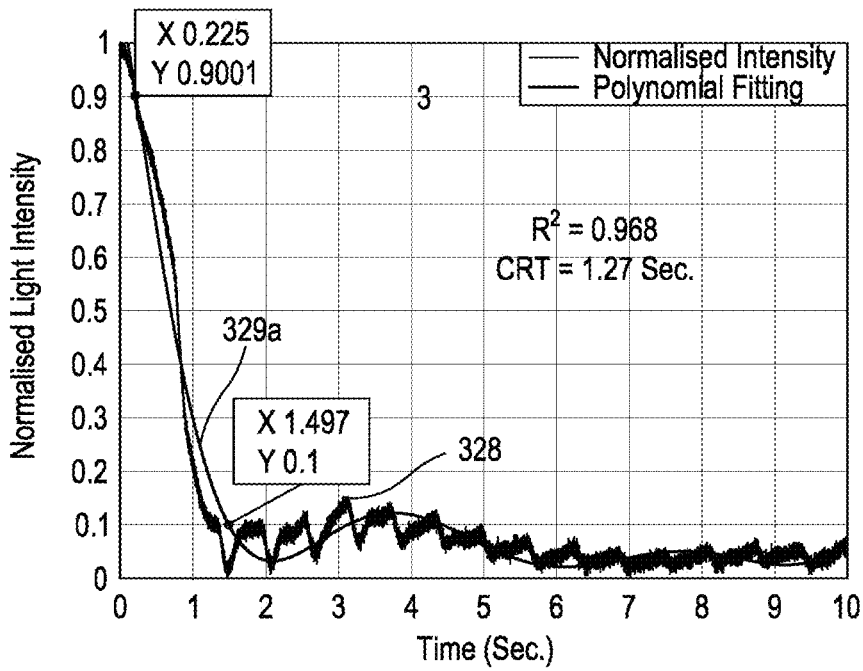
FIG. 49 shows a polynomial fitting applied to normalised results of light intensity as measured during a third period of capillary refill of the test of FIG. 45.

FIG. 47 shows normalised light intensity (curve 328) during the period of capillary refill following the first period of applied pressure of FIG. 45. FIGS. 48 and 49 show normalised light intensity during the periods of capillary refill following the second and third periods of applied pressure of FIG. 47 respectively. Polynomial fittings 329a, 329b and 329c were applied to the normalised light intensity data of FIGS. 47, 48 and 49 respectively. The $R^2$ values obtained from the polynomial fittings 329a, 329b and 329c were 0.972, 0.969 and 0.968 respectively. The CRT values obtained from the polynomial fittings 329a, 329b and 329c were 2.04 s, 1.35 s and 1.27 s respectively. This gives an average $R^2$ value of 0.969, and average CRT value of 1.55 s and a standard deviation of the CRT values of 0.42 s.

Figure 50:
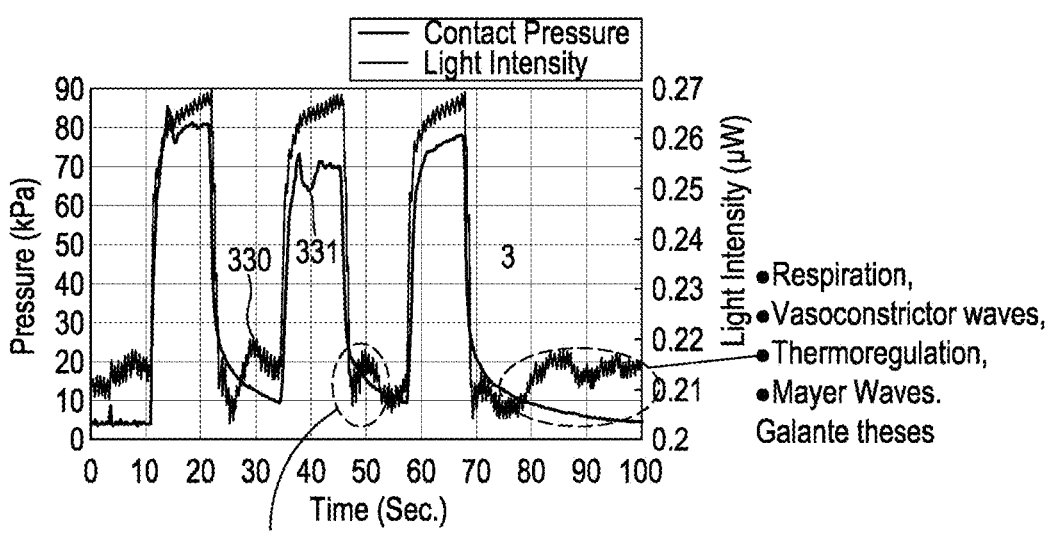
FIG. 50 shows the results of a test during which pressure was applied and released to the system of FIGS. 25, 26 and 27, in the arrangement of FIG. 37, by an individual using their foot whilst in a standing position, in three cycles.
Figure 51:
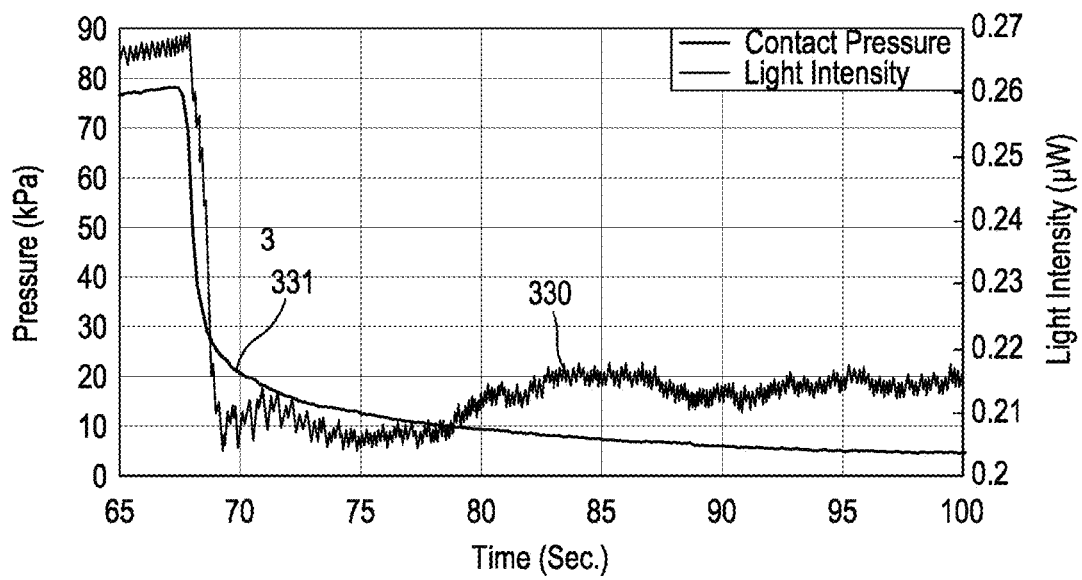
FIG. 51 shows a higher resolution plot of light intensity and pressure measured during a period of capillary refill of the test of FIG. 50.

FIG. 50 shows the results of a test during which pressure was applied and released to the system 100 of FIGS. 25 to 28 in three cycles. The arrangement of the system 100 is that shown in FIG. 37. In the test of FIG. 50, pressure was applied to the system 100 by an individual using their foot whilst in a standing position. Each of the three cycles comprised a period of approximately ten seconds of approximately constant pressure being applied to the system 100, followed by a period of approximately ten seconds during which the pressure was released. FIG. 50 shows light intensity measured at the PPG sensor 110 and pressure measured at the FBG sensor 120 during the test. Green light was utilised by the PPG sensor 110 during the test. Light intensity is shown by curve 330 and pressure is shown by curve 331. A period of capillary refill followed each ten second period of applied pressure. A higher resolution plot of the light intensity and pressure measurements during the period of capillary refill following the third period of applied pressure is shown in FIG. 51.

In the test of FIG. 50, light intensity and pressure was measured for a longer period of time (approximately 30 seconds) following the third period of applied pressure compared to the tests of FIGS. 33, 38, and 45. This was done in order to observe the baseline light intensity after blood had completely refilled. During the approximately 25 seconds following approximately 5 seconds after the third period of applied pressure, respiration, vasoconstrictor waves, thermoregulation, and Mayer waves were observed (Galante, N. J. (2009). "*Photoplethysmographic Waveform Analysis During Lower Body Negative Pressure Simulated Hypovolemia as a Tool to Distinguish Regional Differences in Microvascular Blood Flow Regulation*," Ph.D dissertation, School of medicine, Yale University, USA, 2009). During the approximately 5 seconds following the second period of applied pressure, post-occlusive reactive hyperaemia was observed (Lanting, S. M., Barwick, A. L., Twigg, S. M., Johnson, N.

A., Baker, M. K., Chiu, S. K., . . . & Chuter, V. H. (2017). *Post-occlusive reactive hyperaemia of skin microvasculature and foot complications in type 2 diabetes. Journal of Diabetes and its Complications,* 31(8), 1305-1310).

Figure 52:
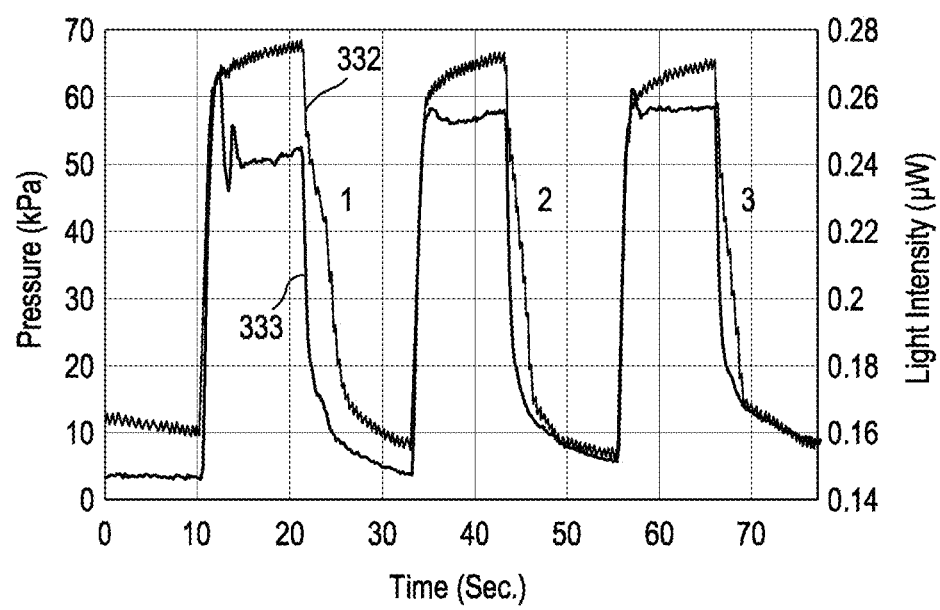
FIG. 52 shows the results of a test during which pressure was applied and released to the system of FIGS. 25, 26 and 27, in the arrangement of FIGS. 43 and 44, by an individual using their foot whilst in a seated position, after their foot had been cooled, in three cycles.
Figure 53:
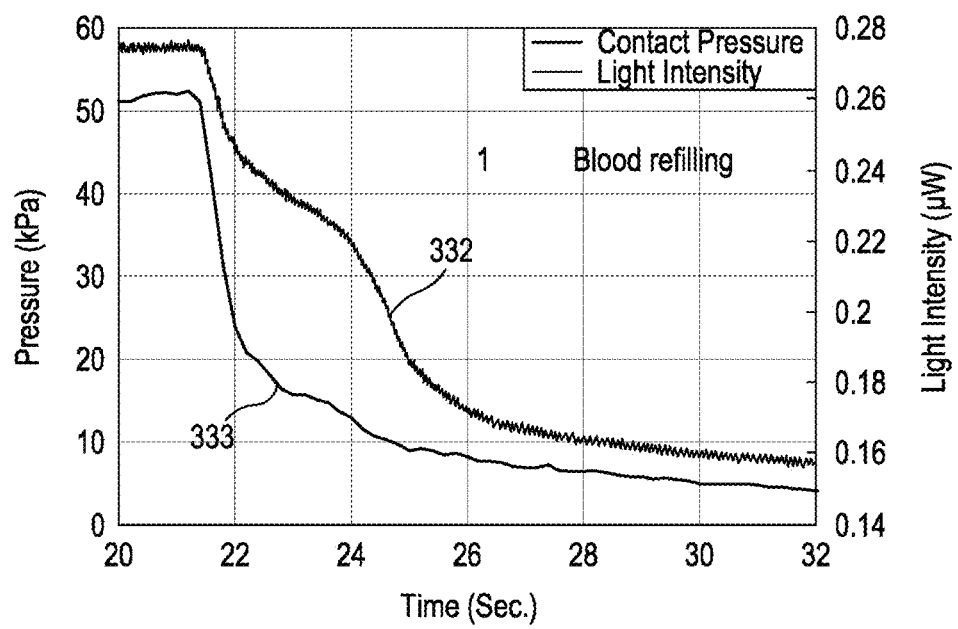
FIG. 53 shows a higher resolution plot of light intensity and pressure measured during a period of capillary refill of the test of FIG. 52.

FIG. 52 shows the results of a test during which pressure was applied and released to the system 100 of FIGS. 25 to 28 in three cycles. The arrangement of the system 100 is that shown in FIGS. 43 and 44. In the test of FIG. 52, pressure was applied to the system 100 by an individual using their foot whilst in a seated position. The foot of the individual was cooled by submerging the foot in icy water for approximately 2 minutes. Each of the three cycles comprised a period of approximately ten seconds of approximately constant pressure being applied to the system 100, followed by a period of approximately ten seconds during which the pressure was released. FIG. 52 shows light intensity measured at the PPG sensor 110 and pressure measured at the FBG sensor 120 during the application of pressure to the system 100 by an individual using their thumb. Green light was utilised by the PPG sensor 110 during the test. Light intensity is shown by curve 332 and pressure is shown by curve 333. A period of capillary refill followed each ten second period of applied pressure. A higher resolution plot of the light intensity and pressure measurements during the period of capillary refill following the first period of applied pressure is shown in FIG. 53.

Figure 54:
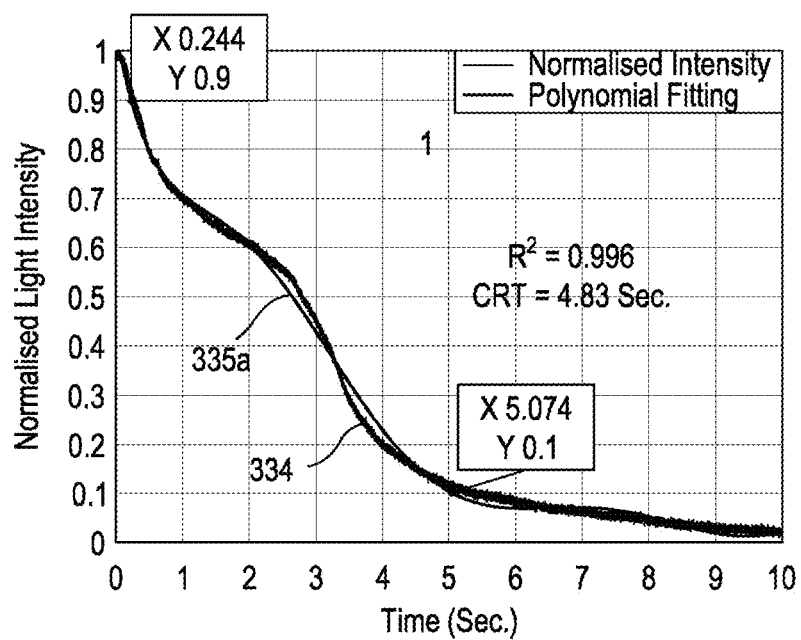
FIG. 54 shows a polynomial fitting applied to normalised results of light intensity as measured during a first period of capillary refill of the test of FIG. 52.
Figure 55:
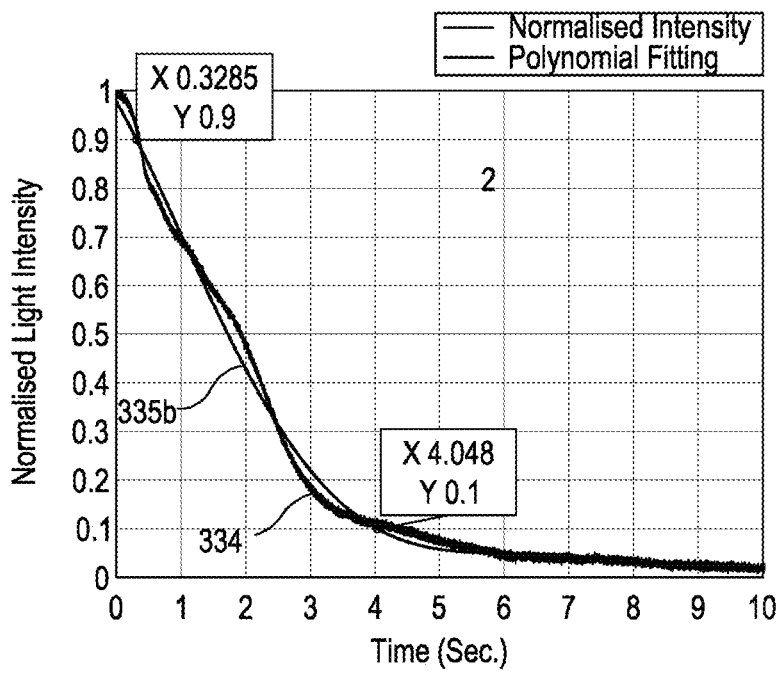
FIG. 55 shows a polynomial fitting applied to normalised results of light intensity as measured during a second period of capillary refill of the test of FIG. 52.
Figure 56:
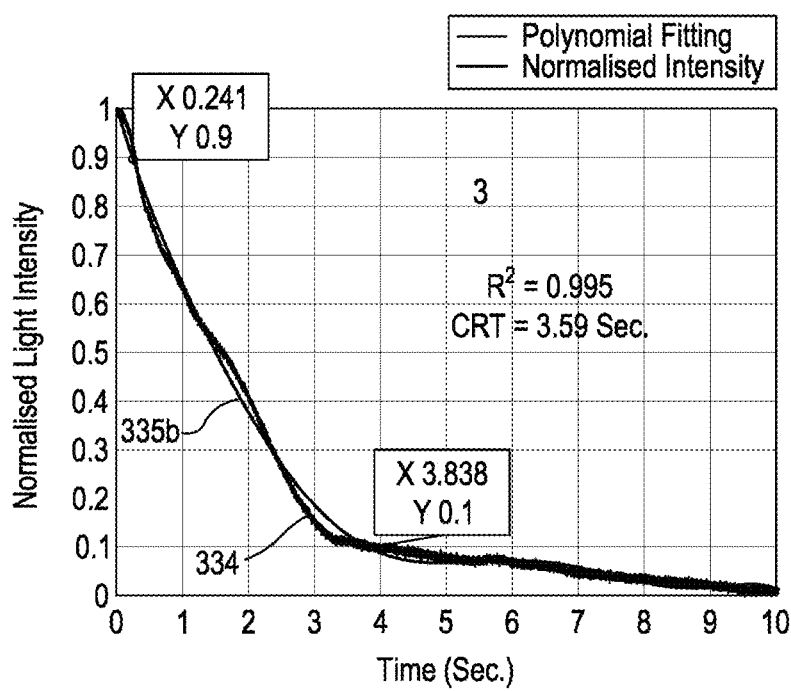
FIG. 56 shows a polynomial fitting applied to normalised results of light intensity as measured during a third period of capillary refill of the test of FIG. 52.

FIG. 54 shows normalised light intensity (curve 334) during the period of capillary refill following the first period of applied pressure of FIG. 52. FIGS. 55 and 56 show normalised light intensity during the periods of capillary refill following the second and third periods of applied pressure of FIG. 52 respectively. Polynomial fittings 335a, 335b and 335c were applied to the normalised light intensity data of FIGS. 47, 48 and 49 respectively. The $R^2$ values obtained from the polynomial fittings 335a, 335b and 335c were 0.996, 0.994 and 0.995 respectively. The CRT values obtained from the polynomial fittings 329a, 329b and 329c were 4.83 s, 3.72 s and 3.59 s respectively. This gives an average $R^2$ value of 0.995, and average CRT value of 4.05 s and a standard deviation of the CRT values of 0.68 s.

A comparison of the result of the tests of FIGS. 45 and 52 shows that average CRT for a cold foot is longer than average CRT for a foot at room temperature.

From reading the present disclosure, other variations and modifications will be apparent to the skilled person. Such variations and modifications may involve equivalent and other features which are already known in the art of physiological monitoring systems, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub-combination. The applicant hereby gives notice that new claims may be formulated to such features and/or combinations of such features during the prosecution of the present application or of any further application derived therefrom.

For the sake of completeness, it is also stated that the term "comprising" does not exclude other elements or steps, the term "a" or "an" does not exclude a plurality, a single processor or other unit may fulfil the functions of several means recited in the claims and any reference signs in the claims shall not be construed as limiting the scope of the claims.

What is claimed is:

1. A system comprising:
   an optical fibre assembly configured to measure one or more physiological parameters of an individual; and
   a pressure sensor configured to measure a contact pressure of the optical fibre assembly on the individual;
   wherein the pressure sensor comprises:
      an optical fibre comprising:
         a transducer fibre Bragg grating;
         a matrix, wherein the transducer fibre Bragg grating is embedded in the matrix and the matrix is configured to cause longitudinal strain in the transducer fibre Bragg grating in response to the matrix being subject to a transverse load; and
         a temperature compensation fibre Bragg grating received in a clearance fit in a cavity of a rigid support member isolating the temperature compensation fibre Bragg grating from a transverse load;
   wherein the optical fibre assembly is configured to measure the physiological parameter only when contact pressure of the optical fibre assembly measured by the pressure sensor is determined to be within a predefined range; and
   wherein the temperature compensation fibre Bragg grating is free to expand and contract independently of the rigid support member.

2. The system of claim 1, wherein the optical fibre of the pressure sensor further comprises a strain compensation fibre Bragg grating or wherein the matrix containing the transducer fibre Bragg grating comprises an elongated longitudinal section relative to a length of the transducer fibre Bragg grating.

3. The system of claim 1, wherein the optical fibre comprises a plurality of transducer fibre Bragg gratings, each of the plurality of fibre Bragg gratings embedded in a respective matrix.

4. The system of claim 3, wherein each of the plurality of transducer fibre Bragg gratings has a corresponding strain compensation fibre Bragg grating; or
   wherein the matrix of each of the plurality of transducer fibre Bragg gratings comprises an elongated longitudinal section relative to a length of the transducer fibre Bragg grating.

5. The system of claim 1, wherein one or more optical fibres of the optical fibre assembly is embedded in a second matrix such that the ends of the one or more optical fibres of the optical fibre assembly are able to transmit light to or receive light from the individual when an outer surface of the matrix is in contact with the individual, and/or
   wherein one or more optical fibres of the optical fibre assembly is embedded in a second matrix such that the ends of the one or more optical fibres of the optical fibre assembly are exposed to gas emitted from the individual;
   wherein the second matrix is the same as or different than matrix in which the transducer fibre Bragg grating is embedded.

6. The system of claim 5, wherein:
   i) the one or more optical fibres of the optical fibre assembly are embedded in the same matrix as the matrix in which a transducer fibre Bragg grating of the optical fibre of the pressure sensor is embedded; or
   ii) the matrix in which the one or more optical fibres of the optical fibre assembly are embedded is connected to a matrix in which a transducer fibre Bragg grating of the optical fibre of the pressure sensor is embedded; and/or
   wherein the matrix in which the one or more optical fibres of the optical fibre assembly are embedded comprises scattering elements configured to diffusely scatter light from the optical fibres, or wherein the system comprises a scattering layer configured to be disposed between the matrix in which the one or more optical fibres of the optical fibre assembly are embedded and the individual, wherein the scattering layer is configured to diffusely scatter light from the optical fibres.

7. The system of claim 1, wherein the optical fibre assembly is configured to measure blood oxygen saturation of an individual when in contact with the individual, the optical fibre assembly comprising:
- a first optical fibre configured to deliver light to the individual at a first wavelength;
- a second optical fibre configured to deliver light to the individual at a second wavelength; and
- a third optical fibre configured to receive light reflected from the individual at both the first and second wavelength; and/or wherein the optical fibre assembly is configured to measure $CO_2$ emitted from the skin of the individual when in contact with the individual, the optical fibre assembly comprising:
- a fourth optical fibre with a tip that is configured with reflectance properties that vary in response to $CO_2$ and which is exposed to gases emitted from the skin of the individual.

8. A handheld probe comprising the system of claim 1.

9. A textile comprising the system of claim 1, comprising a plurality of the optical fibres integrated with the textile by knitting, weaving, embroidering or threading the optical fibres into the textile.

10. The textile of claim 9, wherein the optical fibre of the pressure sensor is integrated with the textile by knitting, weaving, embroidering or threading the optical fibre into the textile.

11. A compression bandage or compression garment comprising the textile of claim 9.

12. A loose fitting garment comprising the textile of claim 9, wherein the optical fibre assembly is configured to measure the one or more physiological parameters only when an appropriate pressure is applied.

13. The loose fitting garment of claim 12, wherein the appropriate pressure is between from 5 kPa to 15 kPa.

14. The system of claim 1, wherein the predefined range of contact pressure of the optical fibre assembly is between from 5 kPa to 15 kPa.

15. A method of monitoring a physiological parameter of an individual, the method comprising:
- applying an optical fibre assembly to an individual;
- measuring the physiological parameter using the optical fibre assembly; and
- measuring a contact pressure of the optical fibre assembly on the individual using a pressure sensor;

wherein the pressure sensor comprises:
- an optical fibre comprising a transducer fibre Bragg grating;
- wherein the transducer fibre Bragg grating is embedded in a matrix, the matrix is configured to cause longitudinal strain in the transducer fibre Bragg grating in response to the matrix being subject to a transverse load; and
- a temperature compensation fibre Bragg grating received in a clearance fit in a cavity of a rigid support member isolating the temperature compensation fibre Bragg grating from a transverse load;

wherein the physiological parameter is measured using the optical fibre assembly only when contact pressure of the optical fibre assembly measured by the pressure sensor is determined to be within a predefined range; and wherein the temperature compensation fibre Bragg grating is free to expand and contract independently of the rigid support member.

16. The method of claim 15, wherein the predefined range of contact pressure of the optical fibre assembly is between from 5 kPa to 15 kPa.

17. The method of claim 15, wherein the optical fibre assembly and the pressure sensor are integrated with a textile, the method comprising applying the textile to the individual to measure the physiological parameter and the contact pressure.

18. The method of claim 17, wherein applying the textile to the individual comprises at least one of the individual i) wearing the textile, ii) lying on the textile, iii) sitting on the textile, iv) resting part of their body on the textile, and/or v) performing an activity whilst at least part of their body is in contact with the textile.

19. The method of claim 15, wherein the optical fibre assembly and the pressure sensor are incorporated into a handheld probe.

* * * * *